US005252571A

United States Patent [19]

[11] Patent Number: 5,252,571

[45] Date of Patent: Oct. 12, 1993

Aotsuka et al.

[54] 1,4-BENZOTHIAZINE-2-ACETIC ACID DERIVATIVES

[75] Inventors: Tomoji Aotsuka, Yaizu; Hiroshi Hosono, Shizuoka; Toshio Kurihara, Shizuoka; Yoshiyuki Nakamura, Shizuoka; Tetsuo Matsui, Shizuoka; Fujio Kobayashi, Shizuoka, all of Japan

[73] Assignee: Sapporo Breweries Limited, Tokyo, Japan

[21] Appl. No.: 813,182

[22] Filed: Dec. 24, 1991

[30] Foreign Application Priority Data

Dec. 27, 1990 [JP] Japan ..... 2-415316
Aug. 6, 1991 [JP] Japan ..... 3-219346

[51] Int. Cl.[5] ..... A61K 31/54; C07D 279/16
[52] U.S. Cl. ..... 514/224.2; 544/52
[58] Field of Search ..... 544/52; 514/224.2

[56] References Cited

U.S. PATENT DOCUMENTS 3,503,965 3/1990 Langis ..... 260/243
3,910,904 10/1975 Worley ..... 260/243

FOREIGN PATENT DOCUMENTS 0162776 11/1985 European Pat. Off. .
0243018 10/1987 European Pat. Off. .
1453465 8/1965 France .

OTHER PUBLICATIONS

Chemical And Pharmaceutical Bulletin, vol. 20, No. 4, Apr., 1972, pp. 832-834, Y. Maki,et al., "Further Studies on the Reaction of 2-Aminothiophenol with Dimethyl Acetylenedicarboxylate".

Chemical And Pharmaceutical Bulletin, vol. 24, No. 9, pp. 2250-2253, 1976, Y. Maki, et al., "Facile Thermal Dimerization of a Photochemically Isomerized Olefin".

*Primary Examiner*—John M. Ford
*Attorney, Agent, or Firm*—Oblon, Spivak, McClelland, Maier & Neustadt

[57] ABSTRACT 1,4-Benzothiazine-2-acetic acid derivatives having an excellent aldose reductase inhibitory activity which are useful for the prevention and treatment of diabetic complications, such as diabetic cataract, retinopathy, nephropathy and neuropathy.

11 Claims, No Drawings

1,4-BENZOTHIAZINE-2-ACETIC ACID DERIVATIVES

BACKGROUND OF THE INVENTION

1. Field of the Invention

The present invention relates to novel 1,4-benzothiazine-2-acetic acid derivatives having an excellent aldose reductase inhibitory activity and pharmaceutically suitable salts thereof, and processes for production thereof as well as a composition comprising the same. The compounds of the present invention are useful for the prevention and treatment of diabetic complications such as diabetic cataract, retinopathy, nephropathy, neuropathy, etc.

2. Description of the Prior Art

Heretofore blood sugar level regulators such as insulin and synthetic hypoglycemic agents have been widely used as drugs for the treatment of diabetes mellitus. However, diabetes mellitus is a disease which accompanies a variety of complications so that it is difficult to prevent development of these complications simply by controlling blood sugar level alone. It has thus been desired to develop a novel drug for the treatment of diabetic complications. In recent years, attention has been brought to accumulation and increase of sorbitol and galactitol in tissue, which is caused by chronic hyperglycemia, as a mechanism of causing diabetic complications.

It is suggested in publications that compounds which inhibit the activity of aldose reductase as an enzyme of reducing an aldose such as glucose and galactose to convert into sorbitol and galactitol. [cf., J. H. Kinoshita et al., Biohim.] Bophys. Acta, 158, 472 (1968), Richard Poulson et al., Biochem. Pharmacol., 32, 1495 (1983), D. Dvornik et al., Science, 182, 1145 (1973)].

Such aldose reductase inhibitors function by inhibiting the activity of enzyme aldose reductase, which is primarily responsible to regulating the reduction of aldoses, such as glucose and galactose, to the corresponding polyols, such as sorbitol and galactitol, in humans and other animals. In this way unwanted accumulation of galactitol in the lens of galactosemic subjects and of sorbitol in the lens, peripheral nervous cord and kidneys of various diabetic subjects are prevented or reduced.

Accordingly, such compounds are of therapeutic value as aldose reductase inhibitors for controlling certain chronic diabetic complications, including those of an ocular nature, since it is known in the art that the presence of polyols in the lens of the eye leads to cataract formation, with a concomitant loss of lens clarity.

Among the compounds synthesized along with such an example, Japanese Patent Application Laid-Open Nos. 61-40264 and 63-107970 disclose that a variety of 1,4-benzothiazine- 4-acetic acid derivatives possess an aldose reductase inhibitory activity. However, it has been desired to develop a drug for the treatment of diabetic complications having a more excellent aldose reductase inhibitory activity.

In a view of such actual situation, the present inventors have made extensive investigations to develop drugs for the treatment of diabetic complications having an aldose reductase inhibitory activity. As a result, it has been found that the object can be achieved by certain benzothiazine derivatives and the present invention has been accomplished.

SUMMARY OF THE INVENTION

That is, the present invention is directed to 1,4-benzothiazine-2-acetic acid derivatives represented by general formula (I) below:

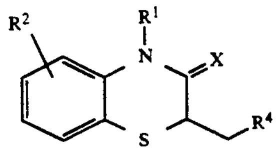

or

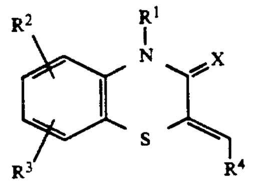

(I)

wherein $R^1$ represents a group shown by general formula (II) or (III):

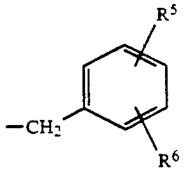

(II)

(wherein $R^5$ and $R^6$, which may be the same or different, each represents hydrogen, a halogen, a lower alkyl group, a lower alkoxyl group, trifluoromethyl or cyano);

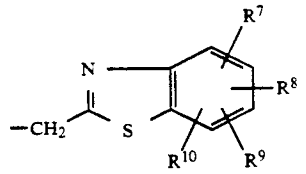

(III)

(wherein $R^7$, $R^8$, $R^9$ and $R^{10}$, which may be the same or different, each represents hydrogen, a halogen, a lower alkyl group, a lower alkoxyl group or trifluoromethyl); $R^2$ and $R^3$, which may be the same or different, each represents hydrogen, a halogen, a lower alkyl group, a lower alkoxyl, a lower alkylthio group, trifluoromethyl or trifluoromethoxy; $R^4$ represents carboxyl which may optionally be esterified; and X represents oxygen or sulfur.

The compounds of the present invention represented by general formula (I) described above are compounds containing a new structure which indispensably requires the 1,4-benzothiazine-2-acetic acid moiety as the basic structure.

In the definition of general formula (I), examples of the halogen include fluorine, chlorine, bromine and iodine. As the lower alkyl group, a straight or branched alkyl group having 1 to 6 carbon atoms are preferred and examples include methyl, ethyl, propyl, isopropyl, butyl, isobutyl, sec-butyl, tert-butyl, pentyl, isopentyl, hexyl, isohexyl, etc.

The lower alkoxyl group refers to a group formed by combining the lower alkyl group described above with an oxygen atom. The lower alkylthio group refers to a group formed by combining the lower alkyl group described above with a sulfur atom.

As the esterified carboxyl group, there are a lower alkoxycarbonyl such as methoxycarbonyl, ethoxycarbonyl, propoxycarbonyl, isopropoxycarbonyl, butoxycarbonyl, isobutoxycarbonyl, tert-butoxycarbonyl, etc., or an aryloxycarbonyl or benzyloxycarbonyl which may optionally have a substituent(s) on the benzene ring.

The compounds of the present invention contain asymmetric carbon and can thus be present in the form or optical isomers, which may be subjected to optical resolution, if necessary and desired, to give pure isomers.

Preferred examples of the salts of the compounds represented by general formula (I) include salts of alkali metals such as lithium, sodium, potassium, etc.; salts of alkaline earth metals such as calcium, magnesium, etc.; organic salts such as triethylamine or pyridine salts.

Preferred compounds represented by general formula (I) in the present invention are where $R^1$ represents a group shown by general formula (III) and further preferred compounds are $R^7$,$R^8$,$R^9$,$R^{10}$ which may be the same or different, each represent hydrogen, fluorion or chlorine.

Representative examples of the compounds (I) in accordance with the present invention are shown below.

2-[4-(Benzothiazol-2-yl)methyl-3, 4-dihydro-3-oxo-2H-1, 4-benzothiazin-2-yl]acetic acid 2-[4-(4-Bromobenzothiazol-2-yl)methyl-3, 4-dihydro-3-oxo-2H-1, 4-benzothiazin-2-yl]acetic acid 2-[4-(5-Bromobenzothiazol-2-yl)methyl-3, 4-dihydro-3-oxo-2H-1, 4-benzothiazin-2-yl]acetic acid 2-[4-(6-Bromobenzothiazol-2-yl)methyl-3, 4-dihydro-3-oxo-2H-1, 4-benzothiazin-2-yl]acetic acid 2-[4-(7-Bromobenzothiazol-2-yl)methyl-3, 4-dihydro-3-oxo-2H-1, 4-benzothiazin-2-yl]acetic acid 2-[4-(4-Chlorobenzothiazol-2-yl)methyl-3, 4-dihydro-3-oxo-2H-1, 4-benzothiazin-2-yl]acetic acid 2-[4-(5-Chlorobenzothiazol-2-yl)methyl-3, 4-dihydro-3-oxo-2H-1, 4-benzothiazin-2-yl]acetic acid 2-[4-(6-Chlorobenzothiazol-2-yl)methyl-3, 4-dihydro-3-oxo-2H-1, 4-benzothiazin-2-yl]acetic acid 2-[4-(7-Chlorobenzothiazol-2-yl)methyl-3, 4-dihydro-3-oxo-2H-1, 4-benzothiazin-2-yl]acetic acid Ethyl 2-[4-(4-fluorobenzothiazol-2-yl)methyl-3, 4-dihydro-3-oxo-2H-1, 4-benzothiazin-2-yl]acetate 2-[4-(4-Fluorobenzothiazol-2-yl)methyl-3, 4-dihydro-3-oxo-2H-1, 4-benzothiazin-2-yl]acetic acid Ethyl 2-[4-(5-fluorobenzothiazol-2-yl)methyl-3, 4-dihydro-3-oxo-2H-1, 4-benzothiazin-2-yl]acetate 2-[4-(5-Fluorobenzothiazol-2-yl)methyl-3, 4-dihydro-3-oxo-2H-1, 4-benzothiazin-2-yl]acetic acid Ethyl 2-[4-(6-fluorobenzothiazol-2-yl)methyl-3, 4-dihydro-3-oxo-2H-1, 4-benzothiazin-2-yl]acetate 2-[4-(6-Fluorobenzothiazol-2-yl)methyl-3, 4-dihydro-3-oxo-2H-1, 4-benzothiazin-2-yl]acetic acid Ethyl 2-[4-(7-fluorobenzothiazol-2-yl)methyl-3, 4-dihydro-3-oxo-2H-1, 4-benzothiazin-2-yl]acetate 2-[4-(7-Fluorobenzothiazol-2-yl)methyl-3, 4-dihydro-3-oxo-2H-1, 4-benzothiazin-2-yl]acetic acid 2-[4-(4-Trifluoromethylbenzothiazol-2-yl)methyl-3, 4-dihydro-3-oxo-2H-1, 4-benzothiazin-2-yl]acetic acid 2-[4-(5-Trifluoromethylbenzothiazol-2-yl)methyl-3, 4-dihydro-3-oxo-2H-1, 4-benzothiazin-2-yl]acetic acid 2-[4-(6-Trifluoromethylbenzothiazol-2-yl)methyl-3, 4-dihydro-3-oxo-2H-1, 4-benzothiazin-2-yl]acetic acid 2-[4-(7-Trifluoromethylbenzothiazol-2-yl)methyl-3, 4-dihydro-3-oxo-2H-1, 4-benzothiazin-2-yl]acetic acid 2-[4-(4-Methylbenzothiazol-2-yl)methyl-3, 4-dihydro-3-oxo-2H-1, 4-benzothiazin-2-yl]acetic acid 2-[4-(5-Methylbenzothiazol-2-yl)methyl-3, 4-dihydro-3-oxo-2H-1, 4-benzothiazin-2-yl]acetic acid 2-[4-(6-Methylbenzothiazol-2-yl)methyl-3, 4-dihydro-3-oxo-2H-1, 4-benzothiazin-2-yl]acetic acid 2-[4-(7-Methylbenzothiazol-2-yl)methyl-3, 4-dihydro-3-oxo-2H-1, 4-benzothiazin-2-yl]acetic acid 2-[4-(4-Methoxybenzothiazol-2-yl)methyl-3, 4-dihydro-3-oxo-2H-1, 4-benzothiazin-2-yl]acetic acid 2-[4-(5-Methoxybenzothiazol-2-yl)methyl-3, 4-dihydro-3-oxo-2H-1, 4-benzothiazin-2-yl]acetic acid 2-[4-(6-Methoxybenzothiazol-2-yl)methyl-3, 4-dihydro-3-oxo-2H-1, 4-benzothiazin-2-yl]acetic acid 2-[4-(7-Methoxybenzothiazol-2-yl)methyl-3, 4-dihydro-3-oxo-2H-1, 4-benzothiazin-2-yl]acetic acid Ethyl 2-[4-(4, 5-dichlorobenzothiazol-2-yl)methyl-3, 4-dihydro-3-oxo-2H-1, 4-benzothiazin-2-yl]acetate 2-[4-(4, 5-Dichlorobenzothiazol-2-yl)methyl-3, 4-dihydro-3-oxo-2H-1, 4-benzothiazin-2-yl]acetic acid 2-[4-(4, 6-Dichlorobenzothiazol-2-yl)methyl-3, 4-dihydro-3-oxo-2H-1, 4-benzothiazin-2-yl]acetic acid 2-[4-(4, 7-Dichlorobenzothiazol-2-yl)methyl-3, 4-dihydro-3-oxo-2H-1, 4-benzothiazin-2-yl]acetic acid 2-[4-(5, 6-Dichlorobenzothiazol-2-yl)methyl-3, 4-dihydro-3-oxo-2H-1, 4-benzothiazin-2-yl]acetic acid 2-[4-(5, 7-Dichlorobenzothiazol-2-yl)methyl-3, 4-dihydro-3-oxo-2H-1, 4-benzothiazin-2-yl]acetic acid 2-[4-(6, 7-Dichlorobenzothiazol-2-.yl)methyl-3, 4-dihydro-3-oxo-2H-1, 4-benzothiazin-2-yl]acetic acid Ethyl 2-[4-(4, 5-difluorobenzothiazol-2-yl)methyl-3, 4-dihydro-3-oxo-2H-1, 4-benzothiazin-2-yl]acetate 2-[4-(4, 5-Difluorobenzothiazol-2-yl)methyl-3, 4-dihydro-3-oxo-2H-1, 4-benzothiazin-2-yl]acetic acid Ethyl 2-[4-(4, 6-difluorobenzothiazol-2-yl)methyl-3, 4-dihydro-3-oxo-2H-1, 4-benzothiazin-2-yl]acetate 2-[4-(4, 6-Difluorobenzothiazol-2-yl)methyl-3, 4-dihydro-3-oxo-2H-1, 4-benzothiazin-2-yl]acetic acid Ethyl 2-[4-(4, 7-difluorobenzothiazol-2-yl)methyl-3, 4-dihydro-3-oxo-2H-1, 4-benzothiazin-2-yl]acetate 2-[4-(4, 7-Difluorobenzothiazol-2-yl)methyl-3, 4-dihydro-3-oxo-2H-1, 4-benzothiazin-2-yl]acetic acid Ethyl 2-[4-(5, 6-difluorobenzothiazol-2-yl)methyl-3, 4-dihydro-3-oxo-2H-1, 4-benzothiazin-2-yl]acetate 2-[4-(5, 6-Difluorobenzothiazol-2-yl)methyl-3, 4-dihydro-3-oxo-2H-1, 4-benzothiazin-2-yl]acetic acid Ethyl 2-[4-(5, 7-difluorobenzothiazol-2-yl)methyl-3, 4-dihydro-3-oxo-2H-1, 4-benzothiazin-2-yl]acetate 2-[4-(5, 7-Difluorobenzothiazol-2-yl)methyl-3, 4-dihydro-3-oxo-2H-1, 4-benzothiazin-2-yl]acetic acid Ethyl 2-[4-(6, 7-difluorobenzothiazol-2-y )methyl-3, 4 -dihydro-3-oxo-2H-1, 4-benzothiazin-2-yl]acetate 2 -[4-(6, 7-Difluorobenzothiazol-2-yl)methyl-3, 4-dihydro-3-oxo-2H-1, 4-benzothiazin-2-yl]acetic acid 2-[4-(4, 5-Bistrifluoromethylbenzothiazol-2-yl)methyl-3, 4-dihydro-3-oxo-2H-1, 4-benzothiazin-2-yl]acetic acid 2-[4-(4, 6-Bistrifluoromethylbenzothiazol-2-yl)methyl-3, 4-dihydro-3-oxo-2H-1, 4-benzothiazin-2-yl]acetic acid 2-[4-(4, 7-Bistrifluoromethylbenzothiazol-2-yl)methyl-3, 4-dihydro-3-oxo-2H-1, 4-benzothiazin-2-yl]acetic acid 2-[4-(5, 6-Bistrifluoromethylbenzothiazol-2-yl)methyl-3, 4-dihydro-3-oxo-2H-1, 4-benzothiazin-2-yl]acetic acid 2-[4-(5, 7-Bistrifluoromethylbenzothiazol-2-yl)methyl-3, 4-dihydro-3-oxo-2H-1, 4-benzothiazin-2-yl]acetic acid 2-[4-(6, 7-Bistrifluoromethylbenzothiazol-2-yl)methyl-3, 4-dihydro-3-oxo-2H-1, 4-benzothiazin-2-yl]acetic acid 2-[4-(4-Chloro-5-fluorobenzothiazol-2-yl)methyl-3, 4-dihydro-3-oxo-2H-1, 4-benzothiazin-2-yl]acetic acid 2-[4-(4-Chloro-7-fluorobenzothiazol-2-yl)methyl-3, 4-dihydro-3-oxo-2H-1, 4-benzothiazin-2-yl]acetic acid 2-[4-(5-Chloro-4-fluorobenzothiazol-2-yl)methyl-3, 4-dihydro-3-oxo-2H-1, 4-benzothiazin-2-yl]acetic acid 2-[4-(5-Chloro-7-fluorobenzothiazol-2-yl)methyl-3, 4-dihydro-3-oxo-2H-1, 4-benzothiazin-2-yl]acetic acid 2-[4-(6-Chloro-7-fluorobenzothiazol-2-yl)methyl-3, 4-dihydro-3-oxo-2H-1, 4-benzothiazin-2-yl]acetic acid 2-[4-(7-Chloro-4-fluorobenzothiazol-2-yl)methyl-3, 4-dihydro-3-oxo-2H-1, 4-benzothiazin-2-yl]acetic acid 2-[4-(7-Chloro-5-fluorobenzothiazol-2-yl)methyl-3, 4-dihydro-3-oxo-2H-1, 4-benzothiazin-2-yl]acetic acid 2-[4-(7-Chloro-6-fluorobenzothiazol-2-yl)methyl-3, 4-dihydro-3-oxo-2H-1, 4-benzothiazin-2-yl]acetic acid 2-[4-(5-Chloro-7-trifluoromethylbenzothiazol-2-yl)methyl-3, 4-dihydro-3-oxo-2H-1, 4-benzothiazin-2-yl]acetic acid 2-[4-(7-Chloro-5-trifluoromethylbenzothiazol-2-yl)methyl-3, 4-dihydro-3-oxo-2H-1, 4-benzothiazin-2-yl]acetic acid 2-[4-(5-Fluoro-7-trifluoromethylbenzothiazol-2-yl)methyl-3, 4-dihydro-3-oxo-2H-1, 4-benzothiazin-2-yl]acetic acid 2-[4-(7-Fluoro-5-trifluoromethylbenzothiazol-2-yl)methyl-3, 4-dihydro-3-oxo-2H-1, 4-benzothiazin-2-yl]acetic acid 2-[4-(4, 5-Dimethylbenzothiazol-2-yl)methyl-3, 4-dihydro-3-oxo-2H-1, 4-benzothiazin-2-yl]acetic acid 2-[4-(4, 7-Dimethylbenzothiazol-2-yl)methyl-3, 4-dihydro-3-oxo-2H-1, 4-benzothiazin-2-yl]acetic acid 2-[4-(5, 7-Dimethylbenzothiazol-2-yl)methyl-3, 4-dihydro-3-oxo-2H-1, 4-benzothiazin-2-yl]acetic acid 2-[4-(4-Fluorobenzothiazol-2-yl)methyl-6-methyl-3, 4-dihydro-3-oxo-2H-1, 4-benzothiazin-2-yl]acetic acid 2-[4-(5-Fluorobenzothiazol-2-yl)methyl-6-methyl-3, 4-dihydro-3-oxo-2H -1, 4-benzothiazin-2-yl]acetic acid 2-[4-(5-Fluorobenzothiazol-2-yl)methyl-6-ethyl-3, 4-dihydro-3-oxo-2H-1, 4-benzothiazin-2-yl]acetic acid 2-[4-(5-Fluorobenzothiazol-2-yl)methyl-6-propyl-3, 4-dihydro-3-oxo-2H-1, 4-benzothiazin-2-yl]acetic acid 2-[4-(5-Fluorobenzothiazol-2-yl)methyl-6-isopropyl-3, 4-dihydro-3-oxo-2H-1, 4-benzothiazin-2-yl]acetic acid 2-[4-(6-Fluorobenzothiazol-2-yl)methyl-6-methyl-3, 4-dihydro-3-oxo-2H-1, 4-benzothiazin-2-yl]acetic acid 2-[4-(7-Fluorobenzothizol-2-yl)methyl-6-methyl-3, 4-dihydro-3-oxo-2H-1, 4-benzothiazin-2-yl]acetic acid 2-[4-(4, 5-Dichlorobenzothiazol-2-yl)methyl-6-methyl-3, 4-dihydro-3-oxo-2H-1, 4-benzothiazin-2-yl]acetic acid 2-[4-(4, 6-Dichlorobenzothiazol-2-yl)methyl-6-methyl-3, 4-dihydro-3-oxo-2H-1, 4-benzothiazin-2-yl]acetic acid 2-[4-(4, 7-Dichlorobenzothiazol-2-yl)methyl-6-methyl-3, 4-dihydro-3-oxo-2H-1, 4-benzothiazin-2-yl]acetic acid 2-[4-(5, 6-Dichlorobenzothiazol-2-yl)methyl-6-methyl-3, 4-dihydro-3-oxo-2H-1, 4-benzothiazin-2-yl]acetic acid 2-[4-(5, 7-Dichlorobenzothiazol-2-yl)methyl-6-methyl-3, 4-dihydro-3-oxo-2H-1, 4-benzothiazin-2-yl]acetic acid 2-[4-(6, 7-Dichlorobenzothiazol-2-yl)methyl-6-methyl-3, 4-dihydro-3-oxo-2H-1, 4-benzothiazin-2-yl]acetic acid 2-[4-(4, 5-Difluorobenzothiazol-2-yl)methyl-6-methyl-3, 4-dihydro-3-oxo-2H-1, 4-benzothiazin-2-yl]acetic acid 2-[4-(4, 6-Difluorobenzothiazol-2-yl)methyl-6-methyl-3, 4-dihydro-3-oxo-2H-1, 4-benzothiazin-2-yl]acetic acid 2-[4-(4, 7-Difluorobenzothiazol-2-yl)methyl-6-methyl-3, 4-dihydro-3-oxo-2H-1, 4-benzothiazin-2-yl]acetic acid 2-[4-(5, 6-Difluorobenzothiazol-2-yl)methyl-6-methyl-3, 4-dihydro-3-oxo-2H-1, 4-benzothiazin-2-yl]acetic acid 2-[4-(5, 7-Difluorobenzothiazol-2-yl)methyl-6-methyl-3, 4-dihydro-3-oxo-2H-1, 4-benzothiazin-2-yl]acetic acid 2-[4-(6, 7-Difluorobenzothiazol-2-yl)methyl-6-methyl-3, 4-dihydro-3-oxo-2H-1, 4-benzothiazin-2-yl]acetic acid 2-[7-Ethoxy-4-(4-fluorobenzothiazol-2-yl)methyl-3, 4-dihydro-3-oxo-2H-1, 4-benzothiazin-2-yl]acetic acid 2-[4-(5-Fluorobenzothiazol-2-yl)methyl-7-methoxy-3, 4-dihydro-3-oxo-2H-1, 4-benzothiazin-2-yl]acetic acid 2-[7-Ethoxy-4-(5-fluorobenzothiazol-2-yl)methyl-3, 4-dihydro-3-oxo-2H-1, 4-benzothiazin-2-yl]acetic acid 2-[4-(5-Fluorobenzothiazol-2-yl)methyl-7-propoxy-3, 4-dihydro-3-oxo-2H-1, 4-benzothiazin-2-yl]acetic acid 2-[7-Ethoxy-4-(6-fluorobenzothiazol-2-yl)methyl-3, 4-dihydro-3-oxo-2H-1, 4-benzothiazin-2-yl]acetic acid 2-[7-Ethoxy-4-(7-fluorobenzothiazol-2-yl)methyl-3, 4-dihydro-3-oxo-2H-1, 4-benzothiazin-2-yl]acetic acid 2-[7-Ethoxy-4-(4, 5-difluorobenzothiazol-2-yl)methyl-3, 4-dihydro-3-oxo-2H-1, 4-benzothiazin-2-yl]acetic acid 2-[7-Ethoxy-4-(4, 6-difluorobenzothiazol-2-yl)methyl-3, 4-dihydro-3-oxo-2H-1, 4-benzothiazin-2-yl]acetic acid 2-[7-Ethoxy-4-(4, 7-difluorobenzothiazol-2-yl)methyl-3, 4-dihydro-3-oxo-2d-l, 4-benzothiazin-2-yl]acetic acid 2-[7-Ethoxy-4-(5, 6-difluorobenzothiazol-2-yl)methyl-3, 4-dihydro-3-oxo-2H-1, 4-benzothiazin-2-yl]acetic acid 2-[7-Ethoxy-4-(5, 7-difluorobenzothiazol-2-yl)methyl-3, 4-dihydro-3-oxo-2H-1, 4-benzothiazin-2-yl]acetic acid 2-[7-Ethoxy-4-(6, 7-difluorobenzothiazol-2-yl)methyl-3, 4-dihydro-3-oxo-2H-1, 4-benzothiazin-2-yl]acetic acid Methyl 2-[5-fluoro-4-(5-fluorobenzothiazol-2-yl)methyl-3, 4-dihydro-3-oxo-2H-1, 4-benzothiazin-2-yl]acetate 2-[5-Fluoro-4-(5-fluorobenzothiazol-2-yl)methyl-3, 4-dihydro-3-oxo-2H-1, 4-benzothiazin-2-yl]acetic acid Methyl 2-(6-fluoro-4-(5-fluorobenzothiazol-2-yl)methyl-3, 4-dihydro-3-oxo-2H-1, 4-benzothiazin-2-yl]acetate 2-[6-Fluoro-4-(5-fluorobenzothiazol-2-yl)methyl-3, 4-dihydro-3-oxo-2H-1, 4-benzothiazin-2-yl]acetic acid 2-[7-Fluoro-4-(5-fluorobenzothiazol-2-yl)methyl-3, 4-dihydro-3-oxo-2H-1, 4-benzothiazin-2-yl]acetic acid 2-[4-(5, 7-Difluorobenzothiazol-2-yl)methyl-7-fluoro-3, 4-dihydro-3-oxo-2H-1, 4-benzothiazin-2-yl]acetic acid 2-[8-Fluoro-4-(5-fluorobenzothiazol-2-yl)methyl-3, 4-dihydro-3-oxo-2H-1, 4-benzothiazin-2-yl]acetic acid Methyl 2-[5-chloro-4-(5-fluorobenzothiazol-2-yl)methyl-3, 4-dihydro-3-oxo-2H-1, 4-benzothiazin-2-yl]acetate 2-[5-Chloro-4-(5-fluorobenzothiazol-2-yl)methyl-3, 4-dihydro-3-oxo-2H-1, 4-benzothiazin-2-yl]acetic acid Methyl 2-[6-chloro-4-(5-fluorobenzothiazol-2-yl)methyl-3, 4-dihydro-3-oxo-2H-1, 4-benzothiazin-2-yl]acetate 2-[6-Chloro-4-(5-fluorobenzothiazol-2-yl)methyl-3, 4-dihydro-3-oxo-2H-1, 4-benzothiazin-2-yl]acetic acid 2-[7-Chloro-4-(5-fluorobenzothiazol-2-yl)methyl-3, 4-dihydro-3-oxo-2H-1, 4-benzothiazin-2-yl]acetic acid 2-[8-Chloro-4-(5-fluorobenzothiazol-2-yl)methyl-3, 4-dihydro-3-oxo-2H-1, 4-benzothiazin-2-yl]acetic acid 2-[6, 7-Dimethyl-4-(5-fluorobenzothiazol-2-yl)methyl-3, 4-dihydro-3-oxo-2H-1, 4-benzothiazin-2-yl]acetic acid 2-[6, 8-Dimethyl-4-(5-fluorobenzothiazol-2-yl)methyl-3, 4-dihydro-3-oxo-2H-1, 4-benzothiazin-2-yl]acetic acid 2-[6, 7-Dimethoxy-4-(5-fluorobenzothiazol-2-yl)methyl-3, 4-dihydro-3-oxo-2H-1, 4-benzothiazin-2-yl]acetic acid 2-[6, 8-Dimethoxy-4-(5-fluorobenzothiazol-2-yl)methyl-3, 4-dihydro-3-oxo-2H-1, 4-benzothiazin-2-yl]acetic acid 2-(6, 7-Dichloro-4-(5-fluorobenzothiazol-2-yl)methyl-3, 4-dihydro-3-oxo-2H-1, 4-benzothiazin-2-yl]acetic acid 2-[6, 8-Dichloro-4-(5-fluorobenzothiazol-2-yl)methyl-3, 4-dihydro-3-oxo-2H-1, 4-benzothiazin-2-yl]acetic acid 2-[7, 8-Dichloro-4-(5-fluorobenzothiazol-2-yl)methyl-3, 4-dihydro-3-oxo-2H-1, 4-benzothiazin-2-yl]acetic acid 2-[6, 7-Difluoro-4-(5-fluorobenzothiazol-2-yl)methyl-3, 4-dihydro-3-oxo-2H-1, 4-benzothiazin-2-yl]acetic acid 2-[6, 8-Difluoro-4-(5-fluorobenzothiazol-2-yl)methyl-3, 4-dihydro-3-oxo-2H-1, 4-benzothiazin-2-yl]acetic acid 2-[7, 8-Difluoro-4-(5-fluorobenzothiazol-2-yl)methyl-3, 4-dihydro-3-oxo-2H-1, 4-benzothiazin-2-yl]acetic acid 2-[4-(4, 5-Dichlorobenzothiazol-2-yl)methyl-7-methyl-3, 4-dihydro-3-oxo-2H-1, 4-benzothiazin-2-yl]acetic acid 2-[4-(4, 5-Dichlorobenzothiazol-2-yl)methyl-6-methoxy-3, 4-dihydro-3-oxo-2H-1, 4-benzothiazin-2-yl]acetic acid 2-[4-(4, 5-Dichlorobenzothiazol-2-yl)methyl-7-methoxy-3, 4-dihydro-3-oxo-2H-1, 4-benzothiazin-2-yl]acetic acid 2-[4-(4, 5-Dichlorobenzothiazol-2-yl)methyl-7-fluoro-3, 4-dihydro-3-oxo-2H-1, 4-benzothiazin-2-yl]acetic acid 2-[4-(4, 5-Dichlorobenzothiazol-2-yl)methyl-6-fluoro-3, 4-dihydro-3-oxo-2H-1, 4-benzothiazin-2-yl]acetic acid 2-[4-(4, 5-Dichlorobenzothiazol-2-yl)methyl -8-fluoro-3, 4-dihydro-3-oxo-2H-1, 4-benzothiazin-2-yl]acetic acid 2-[4-(4, 5-Dichlorobenzothiazol-2-yl)methyl-6-trifluoromethyl-3, 4-dihydro-3-oxo-2H-1, 4-benzothiazin-2-yl]acetic acid 2-[4-(4, 5-Dichlorobenzothiazol-2-yl)methyl-7-trifluoromethyl-3, 4-dihydro-3-oxo-2H-1, 4-benzothiazin-2-yl]acetic acid 2-[4-(4, 5-Dichlorobenzothiazol-2-yl)methyl-7-trifluoromethoxy-3, 4-dihydro-3-oxo-2H-1, 4-benzothiazin-2-yl]acetic acid 2-[4-(4, 5-Dichlorobenzothiazol-2-yl)methyl-6-chloro-3, 4-dihydro-3-oxo-2H-1, 4-benzothiazin-2-yl]acetic acid 2-[4-(4, 5-Dichlorobenzothiazol-2-yl)methyl-7-chloro-3, 4-dihydro-3-oxo-2H-1, 4-benzothiazin-2-yl]acetic acid 2-[4-(4, 5-Dichlorobenzothiazol-2-yl)methyl-8-chloro-3, 4-dihydro-3-oxo-2H-1, 4-benzothiazin-2-yl]acetic acid 2-[4-(4, 5-Dichlorobenzothiazol-2-yl)methyl-6-bromo-3, 4-dihydro-3-oxo-2H-1, 4-benzothiazin-2-yl]acetic acid 2-[4-(4, 5-Dichlorobenzothiazol-2-yl)methyl-7-bromo-3, 4-dihydro-3-oxo-2H-1, 4-benzothiazin-2-yl]acetic acid 2-[4-(4, 5-Dichlorobenzothiazol-2-yl)methyl-8-bromo-3, 4-dihydro-3-oxo-2H-1, 4-benzothiazin-2-yl]acetic acid 2-[4-(4, 5-Dichlorobenzothiazol-2-yl)methyl-6, 8-difluoro-3, 4-dihydro-3-oxo-2H-1, 4-benzothiazin-2-yl]acetic acid 2-[4-(4, 5-Dichlorobenzothiazol-2-yl)methyl-6, 8-dimethyl-3, 4-dihydro-3-oxo-2H-1, 4-benzothiazin-2-yl]acetic acid 2-[4-(4, 5-Dichlorobenzothiazol-2-yl)methyl-6, 7-dimethyl-3, 4-dihydro-3-oxo-2H-1, 4-benzothiazin-2-yl]acetic acid 2-[4-(4, 5-Difluorobenzothiazol-2-yl)methyl-7-methyl-3, 4-dihydro-3-oxo-2d-l, 4-benzothiazin-2-yl]acetic acid 2-[4-(4, 5-Difluorobenzothiazol-2-yl)methyl-6-methoxy-3, 4-dihydro-3-oxo-2H-1, 4-benzothiazin-2-yl]acetic acid 2-[4-(4, 5-Difluorobenzothiazol-2-yl)methyl-7-methoxy-3, 4-dihydro-3-oxo-2H-1, 4-benzothiazin-2-yl]acetic acid 2-[4-(4, 5-Difluorobenzothiazol-2-yl)methyl-7-fluoro-3, 4-dihydro-3-oxo-2H-1, 4-benzothiazin-2-yl]acetic acid 2-[4-(4, 5-Difluorobenzothiazol-2-yl)methyl-6-fluoro-3, 4-dihydro-3-oxo-2H-1, 4-benzothiazin-2-yl]acetic acid 2-[4-(4, 5-Difluorobenzothiazol-2-yl)methyl-8-fluoro-3, 4-dihydro-3-oxo-2H-1, 4-benzothiazin-2-yl]acetic acid 2-[4-(4, 5-Difluorobenzothiazol-2-yl)methyl-6-trifluoromethyl-3, 4-dihydro-3-oxo-2H-1, 4-benzothiazin-2-yl]acetic acid 2-[4-(4, 5-Difluorobenzothiazol-2-yl)methyl-7-trifluoromethyl-3, 4-dihydro-3-oxo-2H-1, 4-benzothiazin-2-yl]acetic acid 2-[4-(4, 5-Difluorobenzothiazol-2-yl)methyl-7-trifluoromethoxy-3, 4-dihydro-3-oxo-2H-1, 4-benzothiazin-2-yl]acetic acid 2-[4-(4, 5-Difluorobenzothiazol-2-yl)methyl-6-chloro-3, 4-dihydro-3-oxo-2H-1, 4-benzothiazin-2-yl]acetic acid 2-[4-(4, 5-Difluorobenzothiazol-2-yl)methyl-7-chloro-3, 4-dihydro-3-oxo-2H-1, 4-benzothiazin-2-yl]acetic acid 2-[4-(4, 5-Difluorobenzothiazol-2-yl)methyl-8-chloro-3, 4-dihydro-3-oxo-2H-1, 4-benzothiazin-2-yl]acetic acid 2-[4-(4, 5-Difluorobenzothiazol-2-yl)methyl-6-bromo-3, 4-dihydro-3-oxo-2H-1, 4-benzothiazin-2-yl]acetic acid 2-[4-(4, 5-Difluorobenzothiazol-2-yl)methyl-7-bromo-3, 4-dihydro-3-oxo-2H-1, 4-benzothiazin-2-yl]acetic acid 2-[4-(4, 5-Difluorobenzothiazol-2-yl)methyl-8-bromo-3, 4-dihydro-3-oxo-2H-1, 4-benzothiazin-2-yl]acetic acid 2-[4-(4, 5-Difluorobenzothiazol-2-yl)methyl-6, 8-difluoro-3, 4-dihydro-3-oxo-2H-1, 4-benzothiazin-2-yl]acetic acid 2-[4-(4, 5-Difluorobenzothiazol-2-yl)methyl-6, 8-dimethyl-3, 4-dihydro-3-oxo-2H-1, 4-benzothiazin-2-yl]acetic acid 2-[4-(4, 5-Difluorobenzothiazol-2-yl)methyl-6, 7-dimethyl-3, 4-dihydro-3-oxo-2H-1, 4-benzothiazin-2-yl]acetic acid 2-[4-(4, 7-Difluorobenzothiazol-2-yl)methyl-7-methyl-3, 4-dihydro-3-oxo-2H-1, 4-benzothiazin-2-yl]acetic acid 2-[4-(4, 7-Difluorobenzothiazol-2-yl)methyl-6-methoxy-3, 4-dihydro-3-oxo-2H-1, 4-benzothiazin-2-yl]acetic acid 2-[4-(4, 7-Difluorobenzothiazol-2-yl)methyl-7-methoxy-3, 4-dihydro-3-oxo-2H-1, 4-benzothiazin-2-yl]acetic acid 2-[4-(4, 7-Difluorobenzothiazol-2-yl)methyl-7-fluoro-3, 4-dihydro-3-oxo-2H-1, 4-benzothiazin-2-yl]acetic acid 2-[4-(4, 7-Difluorobenzothiazol-2-yl)methyl-6-fluoro-3, 4-dihydro-3-oxo-2H-1, 4-benzothiazin-2-yl]acetic acid 2-[4-(4, 7-Difluorobenzothiazol-2-yl)methyl-8-fluoro-3, 4-dihydro-3-oxo-2H-1, 4-benzothiazin-2-yl]acetic acid 2-[4-(4, 7-Difluorobenzothiazol-2-yl)methyl-6-trifluoromethyl-3, 4-dihydro-3-oxo-2H-1, 4-benzothiazin-2-yl]acetic acid 2-[4-(4, 7-Difluorobenzothiazol-2-yl)methyl-7-trifluoromethyl-3, 4-dihydro-3-oxo-2H-1, 4-benzothiazin-2-yl]acetic acid 2-[4-(4, 7-Difluorobenzothiazol-2-yl)methyl-7-trifluoromethoxy-3, 4-dihydro-3-oxo-2H-1, 4-benzothiazin-2-yl]acetic acid 2-[4-(4, 7-Difluorobenzothiazol-2-yl)methyl-6-chloro-3, 4-dihydro-3-oxo-2H-1, 4-benzothiazin-2-yl]acetic acid 2-[4-(4, 7-Difluorobenzothiazol-2-yl)methyl-7-chloro-3, 4-dihydro-3-oxo-2H-1, 4-benzothiazin-2-yl]acetic acid 2-[4-(4, 7-Difluorobenzothiazol-2-yl)methyl-8-chloro-3, 4-dihydro-3-oxo-2H-1, 4-benzothiazin-2-yl]acetic acid 2-[4-(4, 7-Difluorobenzothiazol-2-yl)methyl-6-bromo-3, 4-dihydro-3-oxo-2H-1, 4-benzothiazin-2-yl]acetic acid 2-[4-(4, 7-Difluorobenzothiazol-2-yl)methyl-7-bromo-3, 4-dihydro-3-oxo-2H-1, 4-benzothiazin-2-yl]acetic acid 2-[4-(4, 7-Difluorobenzothiazol-2-yl)methyl-8-bromo-3, 4-dihydro-3-oxo-2H-1, 4-benzothiazin-2-yl]acetic acid 2-[4-(4, 7-Difluorobenzothiazol-2-yl)methyl-6, 8-difluoro-3,4-dihydro-3-oxo-2H-1, 4-benzothiazin-2-yl]acetic acid 2-[4-(4, 7-Difluorobenzothiazol-2-yl)methyl-6, 8-dimethyl-3, 4-dihydro-3-oxo-2H-1, 4-benzothiazin-2-yl]acetic acid 2-[4-(4, 7-Difluorobenzothiazol-2-yl)methyl-6, 7-dimethyl-3, 4-dihydro-3-oxo-2H-1, 4-benzothiazin-2-yl]acetic acid 2-[4-(5, 7-Difluorobenzothiazol-2-yl)methyl-7-methyl-3, 4-dihydro-3-oxo-22-i, 4-benzothiazin-2-yl]acetic acid 2-[4-(5, 7-Difluorobenzothiazol-2-yl)methyl-6-methoxy-3, 4-dihydro-3-oxo-2H-1, 4-benzothiazin-2-yl]acetic acid 2-[4-(5, 7-Difluorobenzothiazol-2-yl)methyl-7-methoxy-3, 4-dihydro-3-oxo-2H-1, 4-benzothiazin-2-yl]acetic acid 2-[4-(5, 7-Difluorobenzothiazol-2-yl)methyl-7-fluoro-3, 4-dihydro-3-oxo-2H-1, 4-benzothiazin-2-yl]acetic acid 2-[4-(5, 7-Difluorobenzothiazol-2-yl)methyl-6-fluoro-3, 4-dihydro-3-oxo-2H-1, 4-benzothiazin-2-yl]acetic acid 2-[4-(5, 7-Difluorobenzothiazol-2-yl)methyl-8-fluoro-3, 4-dihydro-3-oxo-2H-1, 4-benzothiazin-2-yl]acetic acid 2-[4-(5, 7-Difluorobenzothiazol-2-yl)methyl-6-trifluoromethyl-3, 4-dihydro-3-oxo-2H-1, 4-benzothiazin-2-yl]acetic acid 2-[4-(5, 7-Difluorobenzothiazol-2-yl)methyl-7-trifluoromethyl-3, 4-dihydro-3-oxo-2H-1, 4-benzothiazin-2-yl]acetic acid 2-[4-(5, 7-Difluorobenzothiazol-2-yl)methyl-7-trifluoromethoxy-3, 4-dihydro-3-oxo-2H-1, 4-benzothiazin-2-yl]acetic acid 2-[4-(5, 7-Difluorobenzothiazol-2-yl)methyl-6-chloro-3, 4-dihydro-3-oxo-2H-1, 4-benzothiazin-2-yl]acetic acid 2-[4-(5, 7-Difluorobenzothiazol-2-yl)methyl-7-chloro-3, 4-dihydro-3-oxo-2H-1, 4-benzothiazin-2-yl]acetic acid 2-[4-(5, 7-Difluorobenzothiazol-2-yl)methyl-8-chloro-3, 4-dihydro-3-oxo-2H-1, 4-benzothiazin-2-yl]acetic acid 2-[4-(5, 7-Difluorobenzothiazol-2-yl)methyl-6-bromo-3, 4-dihydro-3-oxo-2H-1, 4-benzothiazin-2-yl]acetic acid 2-[4-(5, 7-Difluorobenzothiazol-2-yl)methyl-7-bromo-3, 4-dihydro-3-oxo-2H-1, 4-benzothiazin-2-yl]acetic acid 2-[4-(5, 7-Difluorobenzothiazol-2-yl)methyl-8-bromo-3, 4-dihydro-3-oxo-2H-1, 4-benzothiazin-2-yl]acetic acid 2-[4-(5, 7-Difluorobenzothiazol-2-yl)methyl-6, 8-difluoro-3, 4-dihydro-3-oxo-2H-1, 4-benzothiazin-2-yl]acetic acid 2-[4-(5, 7-Difluorobenzothiazol-2-yl)methyl-6, 8-dimethyl-3, 4-dihydro-3-oxo-2H-1, 4-benzothiazin-2-yl]acetic acid 2-[4-(5, 7-Difluorobenzothiazol-2-yl)methyl-6, 7-dimethyl-3, 4-dihydro-3-oxo-2H-1, 4-benzothiazin-2-yl]acetic acid 2-[4-(6, 7-Difluorobenzothiazol-2-yl)methyl-7-methyl-3, 4-dihydro-3-oxo-2H-1, 4-benzothiazin-2-yl]acetic acid 2-[4-(6, 7-Difluorobenzothiazol-2-yl)methyl-6-methoxy-3, 4-dihydro-3-oxo-2H-1, 4-benzothiazin-2-yl]acetic acid 2-[4-(6, 7-Difluorobenzothiazol-2-yl)methyl-7-methoxy-3, 4-dihydro-3-oxo-2H-1, 4-benzothiazin-2-yl]acetic acid 2-[4-(6, 7-Difluorobenzothiazol-2-yl)methyl-7-fluoro-3, 4-dihydro-3-oxo-2H-1, 4-benzothiazin-2-yl]acetic acid 2-[4-(6, 7-Difluorobenzothiazol-2-yl)methyl-6-fluoro-3, 4-dihydro-3-oxo-2H-1, 4-benzothiazin-2-yl]acetic acid 2-[4-(6, 7-Difluorobenzothiazol-2-yl)methyl-8-fluoro-3, 4-dihydro-3-oxo-2H-1, 4-benzothiazin-2-yl]acetic acid 2-[4-(6, 7-Difluorobenzothiazol-2-yl)methyl-6-trifluoromethyl-3, 4-dihydro-3-oxo-2H-1, 4-benzothiazin-2-yl]acetic acid 2-[4-(6, 7-Difluorobenzothiazol-2-yl)methyl-7-trifluoromethyl-3, 4-dihydro-3-oxo-2H-1, 4-benzothiazin-2-yl]acetic acid 2-[4-(6, 7-Difluorobenzothiazol-2-yl)methyl-7-trifluoromethoxy-3, 4-dihydro-3-oxo-2H-1, 4-benzothiazin-2-yl]acetic acid 2-[4-(6, 7-Difluorobenzothiazol-2-yl)methyl-6-chloro-3, 4-dihydro-3-oxo-2H-1, 4-benzothiazin-2-yl]acetic acid 2-[4-(6, 7-Difluorobenzothiazol-2-yl)methyl-7-chloro-3, 4-dihydro-3-oxo-2H-1, 4-benzothiazin-2-yl]acetic 2-[4-(6, 7-Difluorobenzothiazol-2-yl)methyl-8-chloro-3, 4-dihydro-3-oxo-2H-1, 4-benzothiazin-2-yl]acetic acid 2-[4-(6, 7-Difluorobenzothiazol-2-yl)methyl-6-bromo-3, 4-dihydro-3-oxo-2H-1, 4-benzothiazin-2-yl]acetic acid 2-[4-(6, 7-Difluorobenzothiazol-2-yl)methyl-7-bromo-3, 4-dihydro-3-oxo-2H-1, 4-benzothiazin-2-yl]acetic acid 2-[4-(6, 7-Difluorobenzothiazol-2-yl)methyl-8-bromo-3, 4-dihydro-3-oxo-2H-1, 4-benzothiazin-2-yl]acetic acid 2-[4-(6, 7-Difluorobenzothiazol-2-yl)methyl-6, 8-difluoro-3, 4-dihydro-3-oxo-2H-1, 4-benzothiazin-2-yl]acetic acid 2-[4-(6, 7-Difluorobenzothiazol-2-yl)methyl-6, 8-dimethyl-3, 4-dihydro-3-oxo-2H-1, 4-benzothiazin-2-yl]acetic acid 2-[4-(6, 7-Difluorobenzothiazol-2-yl)methyl-6, 7-dimethyl-3, 4-dihydro-3-oxo-2H-1, 4-benzothiazin-2-yl]acetic acid 2-[4-(4, 5, 7-Trichlorobenzothiazol-2-yl)methyl-3, 4-dihydro-3-oxo-2H-1, 4-benzothiazin-2-yl]acetic acid 2-[4-(4, 5, 7-Trichlorobenzothiazol-2-yl)methyl-6-methyl-3, 4-dihydro-3-oxo-2H-1, 4-benzothiazin-2-yl]acetic acid 2-[4-(4, 5, 7-Trichlorobenzothiazol-2-yl)methyl-7-methyl-3, 4-dihydro-3-oxo-2H-1, 4-benzothiazin-2-yl]acetic acid 2-[4-(4, 5, 7-Trichlorobenzothiazol-2-yl)methyl-6-methoxy-3, 4-dihydro-3-oxo-2H-1, 4-benzothiazin-2-yl]acetic acid 2-[4-(4, 5, 7-Trichlorobenzothiazol-2-yl)methyl-7-methoxy-3, 4-dihydro-3-oxo-2H-1, 4-benzothiazin-2-yl]acetic acid 2-[4-(4, 5, 7-Trichlorobenzothiazol-2-yl)methyl-7-fluoro-3, 4-dihydro-3-oxo-2H-1, 4-benzothiazin-2-yl]acetic acid 2-[4-(4, 5, 7-Trichlorobenzothiazol-2-yl)methyl-6-fluoro-3, 4-dihydro-3-oxo-2H-1, 4-benzothiazin-2-yl]acetic acid 2-[4-(4, 5, 7-Trichlorobenzothiazol-2-yl)methyl-8-fluoro-3, 4-dihydro-3-oxo-2H-1, 4-benzothiazin-2-yl]acetic acid 2-[4-(4, 5, 7-Trichlorobenzothiazol-2-yl)methyl-6-trifluoromethyl-3, 4-dihydro-3-oxo-2H-1, 4-benzothiazin-2-yl]acetic acid 2-[4-(4, 5, 7-Trichlorobenzothiazol-2-yl)methyl-7-trifluoromethyl-3, 4-dihydro-3-oxo-2H-1, 4-benzothiazin-2-yl]acetic acid 2-[4-(4, 5, 7-Trichlorobenzothiazol-2-yl)methyl-7-trifluoromethoxy-3, 4-dihydro-3-oxo-2H-1, 4-benzothiazin-2-yl]acetic acid 2-[4-(4, 5, 7-Trichlorobenzothiazol-2-yl)methyl-6-chloro-3, 4-dihydro-3-oxo-2H-1, 4-benzothiazin-2-yl]acetic acid 2-[4-(4, 5, 7-Trichlorobenzothiazol-2-yl)methyl-7-chloro-3, 4-dihydro-3-oxo-2H-1, 4-benzothiazin-2-yl]acetic acid 2-[4-(4, 5, 7-Trichlorobenzothiazol-2-yl)methyl-8-chloro-3, 4-dihydro-3-oxo-2H-1, 4-benzothiazin-2-yl]acetic acid 2-[4-(4, 5, 7-Trichlorobenzothiazol-2-yl)methyl-6-bromo-3, 4-dihydro-3-oxo-2H-1, 4-benzothiazin-2-yl]acetic acid 2-[4-(4, 5, 7-Trichlorobenzothiazol-2-yl)methyl-7-bromo-3, 4-dihydro-3-oxo-2H-1, 4-benzothiazin-2-yl]acetic acid 2-[4-(4, 5, 7-Trichlorobenzothiazol-2-yl)methyl-8-bromo-3, 4-dihydro-3-oxo-2H-1, 4-benzothiazin-2-yl]acetic acid 2-[4-(4, 5, 7-Trichlorobenzothiazol-2-yl)methyl-6, 8-difluoro-3, 4-dihydro-3-oxo-2H-1, 4-benzothiazin-2-yl]acetic acid 2-[4-(4, 5, 7-Trichloro -2-yl)methyl-6, 8-dimethyl-3, 4-dihydro-3-oxo-2H-1, 4-benzothiazin-2-yl]acetic acid 2-[4-(4, 5, 7-Trichlorobenzothiazol-2-yl)methyl-6, 7-dimethyl-3, 4-dihydro-3-oxo-2H-1, 4-benzothiazin-2-yl]acetic acid 2-[4-(4, 5, 7-Trifluorobenzothiazol-2-yl)methyl-3, 4-dihydro-3-oxo-2H-1, 4-benzothiazin-2-yl]acetic acid 2-[4-(4, 5, 7-Trifluorobenzothiazol-2-yl)methyl-6-methyl-3, 4-dihydro-3-oxo-2H-1, 4-benzothiazin-2-yl]acetic acid 2-[4-(4, 5, 7-Trifluorobenzothiazol-2-yl)methyl-7-methyl-3, 4-dihydro-3-oxo-2H-1, 4-benzothiazin-2-yl]acetic acid 2-[4-(4, 5, 7-Trifluorobenzothiazol-2-yl)methyl-6-methoxy-3, 4-dihydro-3-oxo-2H-1, 4-benzothiazin-2-yl]acetic acid 2-[4-(4, 5, 7-Trifluorobenzothiazol-2-yl)methyl-7-methoxy-3, 4-dihydro-3-oxo-2H-1, 4-benzothiazin-2-yl]acetic acid 2-[4-(4, 5, 7-Trifluorobenzothiazol-2-yl)methyl-7-fluoro-3, 4-dihydro-3-oxo-2H-1, 4-benzothiazin-2-yl]acetic acid 2-[4-(4, 5, 7-Trifluorobenzothiazol-2-yl)methyl-6-fluoro-3, 4-dihydro-3-oxo-2H-1, 4-benzothiazin-2-yl]acetic acid 2-[4-(4, 5, 7-Trifluorobenzothiazol-2-yl)methyl-8-fluoro-3, 4-dihydro-3-oxo-2H-1, 4-benzothiazin-2-yl]acetic acid 2-[4-(4, 5, 7-Trifluorobenzothiazol-2-yl)methyl-6-trifluoromethyl-3, 4-dihydro-3-oxo-2H-1, 4-benzothiazin-2-yl]acetic acid 2-[4-(4, 5, 7-Trifluorobenzothiazol-2-yl)methyl-7-trifluoromethyl-3, 4-dihydro-3-oxo-2H-1, 4-benzothiazin-2-yl]acetic acid 2-[4-(4, 5, 7-Trifluorobenzothiazol-2-yl)methyl-7-trifluoromethoxy-3, 4-dihydro-3-oxo-2H-1, 4-benzothiazin-2-yl]acetic acid 2-[4-(4, 5, 7-Trifluorobenzothiazol-2-yl)methyl-6-chloro-3, 4-dihydro-3-oxo-2H-1, 4-benzothiazin-2-yl]acetic acid 2-[4-(4, 5, 7-Trifluorobenzothiazol-2-yl)methyl-7-chloro-3, 4-dihydro-3-oxo-2H-1, 4-benzothiazin-2-yl]acetic acid 2-[4-(4, 5, 7-Trifluorobenzothiazol-2-yl)methyl-8-chloro-3, 4-dihydro-3-oxo-2H-1, 4-benzothiazin-2-yl]acetic acid 2-[4-(4, 5, 7-Trifluorobenzothiazol-2-yl)methyl-6-bromo-3, 4-dihydro-3-oxo-2H-1, 4-benzothiazin-2-yl]acetic acid 2-[4-(4, 5, 7-Trifluorobenzothiazol-2-yl)methyl-7-bromo-3, 4-dihydro-3-oxo-2H-1, 4-benzothiazin-2-yl]acetic acid 2-[4-(4, 5, 7-Trifluorobenzothiazol-2-yl)methyl-8-bromo-3, 4-dihydro-3-oxo-2H-1, 4-benzothiazin-2-yl]acetic acid 2-[4-(4, 5, 7-Trifluorobenzothiazol-2-yl)methyl-6, 8-difluoro-3, 4-dihydro-3-oxo-2H-1, 4-benzothiazin-2-yl]acetic acid 2-[4-(4, 5, 7-Trifluorobenzothiazol-2-yl)methyl-6, 8-dimethyl-3, 4-dihydro-3-oxo-2H-1, 4-benzothiazin-2-yl]acetic acid 2-[4-(4, 5, 7-Trifluorobenzothiazol-2-yl)methyl-6, 7-dimethyl-3, 4-dihydro-3-oxo-2H-1, 4-benzothiazin-2-yl]acetic acid 2-[4-(4, 5, 6, 7-Tetrafluorobenzothiazol-2-yl)methyl-3, 4-dihydro-3-oxo-2H-1, 4-benzothiazin-2-yl]acetic acid 2-[4-(4, 5, 6, 7-Tetrafluorobenzothiazol-2-yl)methyl-6-methyl-3, 4-dihydro-3-oxo-2H-1, 4-benzothiazin-2-yl]acetic acid 2-[4-(4, 5, 6, 7-Tetrafluorobenzothiazol-2-yl)methyl-7-methyl-3, 4-dihydro-3-oxo-2H-1, 4-benzothiazin-2-yl]acetic acid 2-[4-(4, 5, 6, 7-Tetrafluorobenzothiazol-2-yl)methyl-6-methoxy-3, 4-dihydro-3-oxo-2H-1, 4-benzothiazin-2-yl]acetic acid 2-[4 -(4, 5 , 6 , 7-Tetrafluorobenzothiazol-2-yl)methyl-7-methoxy-3, 4-dihydro-3-oxo-2H-1, 4-benzothiazin-2-yl]acetic acid 2-[4 -(4, 5 , 6 , 7-Tetrafluorobenzothiazol-2-yl)methyl-7-fluoro-3, 4-dihydro-3-oxo-2H-1, 4-benzothiazin-2-yl]acetic acid 2-[4 -(4, 5 , 6 , 7-Tetrafluorobenzothiazol-2-yl)methyl-6-fluoro-3, 4-dihydro-3-oxo-2H-1, 4-benzothiazin-2-yl]acetic acid 2-[4-(4, 5, 6, 7-Tetrafluorobenzothiazol-2-yl)methyl-8-fluoro-3, 4-dihydro-3-oxo-2H-1, 4-benzothiazin-2-yl]acetic acid 2-[4-(4, 5, 6, 7-Tetrafluorobenzothiazol-2-yl)methyl-6-trifluoromethyl-3, 4-dihydro-3-oxo-2H-1, 4-benzothiazin-2-yl]acetic acid 2-[4 -(4, 5 , 6 , 7-Tetrafluorobenzothiazol-2-yl)methyl-7-trifluoromethyl-3, 4-dihydro-3-oxo-2H-1, 4-benzothiazin-2-yl]acetic acid 2-[4-(4-Fluorobenzothiazol-2-yl)methyl-3, 4-dihydro-3-thioxo-2H-1, 4-benzothiazin-2-yl]acetic acid Ethyl 2-[4-(5-fluorobenzothiazol-2-yl)methyl-3, 4-dihydro-3-thioxo-2H-1, 4-benzothiazin-2-yl]acetate 2-[4-(5-Fluorobenzothiazol-2-yl)methyl-3, 4-dihydro-3-thioxo-2H-1, 4-benzothiazin-2-yl]acetic acid 2-[4-(5-Fluorobenzothiazol-2-yl)methyl-6-methyl-3, 4-dihydro-3-thioxo-2H-1, 4-benzothiazin-2-yl]acetic acid 2-[7-Ethoxy-4-(5-fluorobenzothiazol-2-yl)methyl-3, 4-dihydro-3-thioxo-2H-1, 4-benzothiazin-2-yl]acetic acid 2-[4-(6-Fluorobenzothiazol-2-yl)methyl-3, -dihydro-3-thioxo-2H-1, 4-benzothiazin-2-yl]acetic acid 2-[4-(7-Fluorobenzothiazol-2-yl)methyl-3, 4-dihydro-3-thioxo-2H-1, 4-benzothiazin-2-yl]acetic acid 2-[4-(4, 5-Difluorobenzothiazol-2-Yl)methyl-3, 4-dihydro-3-thioxo-2H-1, 4-benzothiazin-2-yl]acetic acid 2-[4 -(4, 5-Difluorobenzothiazol-2-yl)methyl-6-methyl-3, 4 -dihydro-3-thioxo-2H-J, 4-benzothiazin-2-yl]acetic acid 2-[4-(4,6-Difluorobenzothiazol-2-yl)methyl-3, 4-dihydro-3-thioxo-2H-1, 4-benzothiazin-2-yl]acetic acid 2-[4-(4, 7-Difluorobenzothiazol-2-yl)methyl-3, 4-dihydro-3-thioxo-2d-l, 4-benzothiazin-2-yl]acetic acid 2-[4-(5, 6-Difluorobenzothiazol-2-yl)methyl-3, 4-dihydro-3-thioxo-2H-1, 4-benzothiazin-2-yl]acetic acid Ethyl 2-[4-(5, 7-difluorobenzothiazol-2-yl)methyl-3, 4-dihydro-3-thioxo-2H-1, 4-benzothiazin-2-yl]acetate 2-[4-(5, 7-Difluorobenzothiazol-2-yl)methyl-3, 4-dihydro-3-thioxo-2H-1, 4-benzothiazin-2-yl]acetic acid 2-[4-(5, 7-Difluorobenzothiazol-2-yl)methyl-6-methyl-3, 4-dihydro-3-thioxo-2H-1, 4-benzothiazin-2-yl]acetic acid Ethyl 2-[4-(6, 7-difluorobenzothiazol-2-yl)methyl-3, 4-dihydro-3-thioxo-2H-J, 4-benzothiazin-2-yl]acetate 2-[4-(6, 7-Difluorobenzothiazol-2-yl)methyl-3, 4-dihydro-3-thioxo-2H-1, 4-benzothiazin-2-yl]acetic acid 2-[4-(6, 7-Difluorobenzothiazol-2-yl)methyl-6-methyl-3, 4-dihydro-3-thioxo-2H-1, 4-benzothiazin-2-yl]acetic acid 2-[4-(4, 5-Dichlorobenzothiazol-2-yl)methyl-3, 4-dihydro-3-thioxo-2H-1, 4-benzothiazin-2-yl]acetic acid 2-[4-(4, 5-Dichlorobenzothiazol-2-yl)methyl-6-methyl-3, 4-dihydro-3-thioxo-2H-J, 4-benzothiazin-2-yl]acetic acid Methyl 2-[4-benzyl-3, 4-dihydro-3-oxo-2H-1, 4-benzothiazin-2-yl]acetate, 2-[4-Benzyl-3, 4-dihydro-3-oxo-2H-1, 4-benzothiazin-2-yl]acetic acid, Methyl 2-[4-(4-methylphenylmethyl)-3, 4-dihydro-3-oxo-2H-1, 4-benzothiazin-2-yl]acetate, 2-[4-(4-Methylphenylmethyl)-3, 4-dihydro-3-oxo-2H-1, 4-benzothiazin-2-yl]acetic acid 2-[4-(4-Ethylphenylmethyl)-3, 4-dihydro-3-oxo-2H-1, 4-benzothiazin-2-yl]acetic acid 2-[4-(4-Propylphenylmethyl)-3, 4-dihydro-3-oxo-2H-1, 4-benzothiazin-2-yl]acetic acid 2-[4-(4-Isopropylphenylmethyl)-3, 4-dihydro-3-oxo-2H-1, 4-benzothiazin-2-yl]acetic acid 2-[4-(4-Butylphenylmethyl)-3, 4-dihydro-3-oxo-2H-1, 4-benzothiazin-2-yl]acetic acid 2-[4-(4-Isobutylphenylmethyl)-3, 4-dihydro-3-oxo-2H-1, 4-benzothiazin-2-yl]acetic acid 2-[4-(4-sec-Butylphenylmethyl)-3, 4-dihydro-3-oxo-2H-1, 4-benzothiazin-2-yl]acetic acid 2-[4-(4-tert-Butylphenylmethyl)-3, 4-dihydro-3-oxo-2H-1, 4-benzothiazin-2-yl]acetic acid 2-[4-(4-Pentylphenylmethyl)-3, 4-dihydro-3-oxo-2H-1, 4-benzothiazin-2-yl]acetic acid 2-[4-(4-Hexylphenylmethyl)-3, 4-dihydro-3-oxo-2H-1, 4-benzothiazin-2-yl]acetic acid 2-[4-(4-Methoxyphenylmethyl)-3, 4-dihydro-3-oxo-2H-1, 4-benzothiazin-2-yl]acetic acid Methyl 2-[4-(4-methoxyphenylmethyl)-3, 4-dihydro-3-oxo-2H-1, 4-benzothiazin-2-yl]acetate, 2-[4-(4-Ethoxyphenylmethyl)-3, 4-dihydro-3-oxo-2H-1, 4-benzothiazin-2-yl]acetic acid 2-[4-(4 -Propoxyphenylmethyl)-3, 4-dihydro-3-oxo-2H-1, 4-benzothiazin-2-yl]acetic acid 2-[4-(4-Isopropoxyphenylmethyl)-3, 4-dihydro-3-oxo-2H-1, 4-benzothiazin-2-yl]acetic acid 2-[4-(4-Butoxyphenylmethyl)-3, 4-dihydro-3-oxo-2H-1, 4-benzothiazin-2-yl]acetic acid 2-[4-(4-Isobutoxyphenylmethyl)-3, 4-dihydro-3-oxo-2H-1, 4-benzothiazin-2-yl]acetic acid 2-[4-(4-sec-Butoxyphenylmethyl)-3, 4-dihydro-3-oxo-2H-1, 4-benzothiazin-2-yl]acetic acid 2-[4-(4-tert-Butoxyphenylmethyl)-3, 4-dihydro-3-oxo-2H-1, 4-benzothiazin-2-yl]acetic acid 2-[4-(4-Pentyloxyphenylmethyl)-3, 4-dihydro-3-oxo-2H-1, 4-benzothiazin-2-yl]acetic acid 2-[4-(4-Hexyloxyphenylmethyl)-3, 4-dihydro-3-oxo-2H-1, 4-benzothiazin-2-yl]acetic acid 2-[4-(3-Cyanophenylmethyl)-3, 4-dihydro-3-oxo-2H-1, 4-benzothiazin-2-yl]acetic acid 2-[4-(4-Bromophenylmethyl)-3, 4-dihydro-3-oxo-2H-1, 4-benzothiazin-2-yl]acetic acid 2-[4-(4-Bromo-3-chlorophenylmethyl)-3, 4-dihydro-3-oxo-2H-1, 4-benzothiazin-2-yl]acetic acid 2-[4-(4-Bromo-2-fluorophenylmethyl)-3, 4-dihydro-3-oxo-2H-1, 4-benzothiazin-2-yl]acetic acid 2-[4-(5-Bromo-2-fluorophenylmethyl)-3, 4-dihydro-3-oxo-2H-1, 4-benzothiazin-2-yl]acetic acid 2-[4-(4-Chlorophenylmethyl)-3, 4-dihydro-3-oxo-2H-1, 4-benzothiazin-2-yl]acetic acid 2-[4-(2, 3-Dichlorophenylmethyl)-3, 4-dihydro-3-oxo-2H-1, 4-benzothiazin-2-yl]acetic acid 2-[4-(2, 4-Dichlorophenylmethyl)-3, 4-dihydro-3-oxo-2H-1, 4-benzothiazin-2-yl]acetic acid 2-[4-(2, 5-Dichlorophenylmethyl)-3, 4-dihydro-3-oxo-2H-1, 4-benzothiazin-2-yl]acetic acid 2-[4-(2, 6-Dichlorophenylmethyl)-3, 4-dihydro-3-oxo-2H-1, 4-benzothiazin-2-yl]acetic acid 2-[4-(3, 4-Dichlorophenylmethyl)-3, 4-dihydro-3-oxo-2H-1, 4-benzothiazin-2-yl]acetic acid 2-[4-(3, 5-Dichlorophenylmethyl)-3, 4-dihydro-3-oxo-2H-1, 4-benzothiazin-2-yl]acetic acid 2-[4-(3-Chloro-4-methoxyphenylmethyl)-3, 4-dihydro-3-oxo-2H-1, 4-benzothiazin-2-yl]acetic acid 2-[4-(3-Chloro-4-iodophenylmethyl)-3, 4-dihydro-3-oxo-2H-1, 4-benzothiazin-2-yl]acetic acid 2-[4-(4-Chloro-2-fluorophenylmethyl)-3, 4-dihydro-3-oxo-2H-1, 4-benzothiazin-2-yl]acetic acid 2-[4-(4-Chloro-3-trifluoromethylphenylmethyl)-3, 4-dihydro-3-oxo-2H-1, 4-benzothiazin-2-yl]acetic acid 2-[4-(4-Chloro-3-methoxyphenylmethyl)-3, 4-dihydro-3-oxo-2H-1, 4-benzothiazin-2-yl]acetic acid 2-[4-(2-Fluorophenylmethyl)-3, 4-dihydro-3-oxo-2H-1, 4-benzothiazin-2-yl]acetic acid 2-[4-(2-Fluoro-3-iodophenylmethyl)-3, 4-dihydro-3-oxo-2H-1, 4-benzothiazin-2-yl]acetic acid 2-[4-(2-Fluoro-4-iodophenylmethyl)-3, 4-dihydro-3-oxo-2H-1, 4-benzothiazin-2-yl]acetic acid 2-[4-(3-Trifluoromethylphenylmethyl)-3, 4-dihydro-3-oxo-2H-1, 4-benzothiazin-2-yl]acetic acid 2-[4-(3, 5-Bistrifluoromethylphenylmethyl)-3, 4-dihydro-3-oxo-2H-1, 4-benzothiazin-2-yl]acetic acid 2-[4-(4-Bromo-2-fluorophenylmethyl)-5-chloro-3, 4-dihydro-3-oxo-2H-1, 4-benzothiazin-2-yl]acetic acid 2-[4-(4-Bromo-2-fluorophenylmethyl)-6-chloro-3, 4-dihydro-3-oxo-2H-1, 4-benzothiazin-2-yl]acetic acid 2-[4-(4-Bromo-2-fluorophenylmethyl)-7-chloro-3, 4-dihydro-3-oxo-2H-1, 4-benzothiazin-2-yl]acetic acid 2-[4-(4-Bromo-2-fluorophenylmethyl)-8-chloro-3, 4-dihydro-3-oxo-2H-1, 4-benzothiazin-2-yl]acetic acid 2-[4-(4-Bromo-2-fluorophenylmethyl)-5-fluoro-3, 4-dihydro-3-oxo-2H-1, 4-benzothiazin-2-yl]acetic acid 2-[4-(4-Bromo-2-fluorophenylmethyl)-6-fluoro-3, 4-dihydro-3-oxo-2H-1, 4-benzothiazin-2-yl]acetic acid 2-[4-(4-Bromo-2-fluorophenylmethyl)-7-fluoro-3, 4-dihydro-3-oxo-2H-1, 4-benzothiazin-2-yl]acetic acid 2-[4-(4-Bromo-2-fluorophenylmethyl)-8-fluoro-3, 4-dihydro-3-oxo-2H-1, 4-benzothiazin-2-yl]acetic acid Ethyl 2-[4-(4-bromo-2-fluorophenylmethyl)-5-methyl-3, 4-dihydro-3-oxo-2H-1, 4-benzothiazin-2-yl]acetate, Ethyl 2-[4-(4-bromo-2-fluorophenylmethyl)-6-methyl-3, 4-dihydro-3-oxo-2H-1, 4-benzothiazin-2-yl]acetate, Ethyl 2-[4-(4-bromo-2-fluorophenylmethyl)-7-methyl-3, 4-dihydro-3-oxo-2H-1, 4-benzothiazin-2-yl]acetate, Ethyl 2-[4-(4-bromo-2-fluorophenylmethyl)-8-methyl-3, 4-dihydro-3-oxo-2H-1, 4-benzothiazin-2-yl]acetate, 2-[4-(4-Bromo-2-fluorophenylmethyl)-5-methyl-3, 4-dihydro-3-oxo-2H-1, 4-benzothiazin-2-yl]acetic acid 2-[4-(4-Bromo-2-fluorophenylmethyl)-6-methyl-3, 4-dihydro-3-oxo-2H-1, 4-benzothiazin-2-yl]acetic acid 2-[4-(4-Bromo-2-fluorophenylmethyl)-7-methyl-3, 4-dihydro-3-oxo-2H-1, 4-benzothiazin-2-yl]acetic acid 2-[4-(4-Bromo-2-fluorophenylmethyl)-8-methyl-3, 4-dihydro-3-oxo-2H-1, 4-benzothiazin-2-yl]acetic acid 2-[4-(4-Bromo-2-fluorophenylmethyl)-5-ethyl-3, 4-dihydro-3-oxo-2H-1, 4-benzothiazin-2-yl]acetic acid Propyl-2-[4-(4-bromo-2-fluorophenylmethyl)-6-ethyl-3, 4-dihydro-3-oxo-2H-1, 4-benzothiazin-2-yl]acetate, 2-[4-(4-Bromo-2-fluorophenylmethyl)-6-ethyl-3, 4-dihydro-3-oxo-2H-1, 4-benzothiazin-2-yl]acetic acid 2-[4-(4-Bromo-2-fluorophenylmethyl)-7-ethyl-3, 4-dihydro-3-oxo-2H-1, 4-benzothiazin-2-yl]acetic acid 2-[4-(4-Bromo-2-fluorophenylmethyl)-8-ethyl-3, 4-dihydro-3-oxo-2H-1, 4-benzothiazin-2-yl]acetic acid 2-[4-(4-Bromo-2-fluorophenylmethyl)-6-propyl-3, 4-dihydro-3-oxo-2H-1, 4-benzothiazin-2-yl]acetic acid 2-[4-(4-Bromo-2-fluorophenylmethyl)-6-isopropyl-3, 4-dihydro-3-oxo-2H-1, 4-benzothiazin-2-yl]acetic acid 2-[4-(4-Bromo-2-fluorophenylmethyl)-7-isopropyl-3, 4-dihydro-3-oxo-2H-1, 4-benzothiazin-2-yl]acetic acid 2-[4-(4-Bromo-2-fluorophenylmethyl)-8-isopropyl-3, 4-dihydro-3-oxo-2H-1, 4-benzothiazin-2-yl]acetic acid 2-[4-(4-Bromo-2-fluorophenylmethyl)-6-butyl-3, 4-dihydro-3-oxo-2H-1, 4-benzothiazin-2-yl]acetic acid 2-[4-(4-Bromo-2-fluorophenylmethyl)-6-isobutyl-3, 4-dihydro-3-oxo-2H-1, 4-benzothiazin-2-yl]acetic acid 2-[4-(4-Bromo-2-fluorophenylmethyl)-6-sec-butyl-3, 4-dihydro-3-oxo-2H-1, 4-benzothiazin-2-yl]acetic acid Isopropyl 2-[4-(4-bromo-2-fluorophenylmethyl)-6-tert-butyl-3, 4-dihydro-3-oxo-2H-1, 4-benzothiazin-2-yl]acetate, 2-[4-(4-Bromo-2-fluorophenylmethyl)-6-tert-butyl-3, 4-dihydro-3-oxo-2H-1, 4-benzothiazin-2-yl]acetic acid 2-[4-(4-Bromo-2-fluorophenylmethyl)-7-tert-butyl-3, 4-dihydro-3-oxo-2H-1, 4-benzothiazin-2-yl]acetic acid 2-[4-(4-Bromo-2-fluorophenylmethyl)-8-tert-butyl-3, 4-dihydro-3-oxo-2H-1, 4-benzothiazin-2-yl]acetic acid 2-[4-(4-Bromo-2-fluorophenylmethyl)-6-pentyl-3, 4-dihydro-3-oxo-2H-1, 4-benzothiazin-2-yl]acetic acid 2-[4-(4-Bromo-2-fluorophenylmethyl)-6-hexyl-3, 4-dihydro-3-oxo-2H-1, 4-benzothiazin-2-yl]acetic acid 2-[4-(4-Bromo-2-fluorophenylmethyl)-5-methoxy-3, 4-dihydro-3-oxo-2H-1, 4-benzothiazin-2-yl]acetic acid 2-[4-(4-Bromo-2-fluorophenylmethyl)-6-methoxy-3, 4-dihydro-3-oxo-2H-1, 4-benzothiazin-2-yl]acetic acid 2-[4-(4-Bromo-2-fluorophenylmethyl)-7-methoxy-3, 4-dihydro-3-oxo-2H-1, 4-benzothiazin-2-yl]acetic acid 2-[4-(4-Bromo-2-fluorophenylmethyl)-8-methoxy-3, 4-dihydro-3-oxo-2H-1, 4-benzothiazin-2-yl]acetic acid 2-[4-(4-Bromo-2-fluorophenylmethyl)-5-ethoxy-3, 4-dihydro-3-oxo-2H-1, 4-benzothiazin-2-yl]acetic acid Butyl 2-[4-(4-bromo-2-fluorophenylmethyl)-6-ethoxy-3, 4-dihydro-3-oxo-2H-1, 4-benzothiazin-2-yl]acetate, 2-[4-(4-Bromo-2-fluorophenylmethyl)-6-ethoxy-3, 4-dihydro-3-oxo-2H-1, 4-benzothiazin-2-yl]acetic acid 2-[4-(4-Bromo-2-fluorophenylmethyl)-7-ethoxy-3, 4-dihydro-3-oxo-2d-l, 4-benzothiazin-2-yl]acetic acid 2-[4-(4-Bromo-2-fluorophenylmethyl)-8-ethoxy-3, 4-dihydro-3-oxo-2H-1, 4-benzothiazin-2-yl]acetic acid 2-[4-(4-Bromo-2-fluorophenylmethyl)-6-propoxy-3, 4-dihydro-3-oxo-2H-1, 4-benzothiazin-2-yl]acetic acid Isobutyl 2-[4-(4-bromo-2-fluorophenylmethyl)-6-isopropoxy-3, 4-dihydro-3-oxo-2H-1, 4-benzothiazin-2-yl]acetate, 2-[4-(4-Bromo-2-fluorophenylmethyl)-6-isopropoxy-3, 4-dihydro-3-oxo-2H-1, 4-benzothiazin-2-yl]acetic acid 2-[4-(4-Bromo-2-fluorophenylmethyl)-7-isopropoxy-3, 4-dihydro-3-oxo-2H-1, 4-benzothiazin-2-yl]acetic acid 2-[4-(4-Bromo-2-fluorophenylmethyl)-8-isopropoxy-3, 4-dihydro-3-oxo-2H-1, 4-benzothiazin-2-yl]acetic acid 2-[4-(4-Bromo-2-fluorophenylmethyl)-6-butoxy-3, 4-dihydro-3-oxo-2H-1, 4-benzothiazin-2-yl]acetic acid 2-[4-(4-Bromo-2-fluorophenylmethyl)-6-isobutoxy-3, 4-dihydro-3-oxo-2H-1, 4-benzothiazin-2-yl]acetic acid 2-[4-(4-Bromo-2-fluorophenylmethyl)-6-sec-butoxy-3, 4-dihydro-3-oxo-2H-1, 4-benzothiazin-2-yl]acetic acid 2-[4-(4-Bromo-2-fluorophenylmethyl)-6-tert-butoxy-3, 4-dihydro-3-oxo-2H-1, 4-benzothiazin-2-yl]acetic acid 2-[4-(4-Bromo-2-fluorophenylmethyl)-7-tert-butoxy-3, 4-dihydro-3-oxo-2H-1, 4-benzothiazin-2-yl]acetic acid 2-[4-(4-Bromo-2-fluorophenylmethyl)-8-tert-butoxy-3, 4-dihydro-3-oxo-2H-1, 4-benzothiazin-2-yl]acetic acid 2-[4-(4-Bromo-2-fluorophenylmethyl)-6-pentyloxy-3, 4-dihydro-3-oxo-2H-1, 4-benzothiazin-2-yl]acetic acid 2-[4-(4-Bromo-2-fluorophenylmethyl)-6-hexyloxy-3, 4-dihydro-3-oxo-2H-1, 4-benzothiazin-2-yl]acetic acid 2-[5-Chloro-4-(3, 4-dichlorophenylmethyl)-3, 4-dihydro-3-oxo-2H-1, 4-benzothiazin-2-yl]acetic acid 2-[6-Chloro-4-(3, 4-dichlorophenylmethyl)-3, 4-dihydro-3-oxo-2H-1, 4-benzothiazin-2-yl]acetic acid 2-[7-Chloro-4-(3, 4-dichlorophenylmethyl)-3, 4-dihydro-3-oxo-2H-1, 4-benzothiazin-2-yl]acetic acid 2-[8-Chloro-4-(3, 4-dichlorophenylmethyl)-3, 4-dihydro-3-oxo-2H-1, 4-benzothiazin-2-yl]acetic acid 2-[4-(3, 4-Dichlorophenylmethyl)-5-fluoro-3, 4-dihydro-3-oxo-2H-1, 4-benzothiazin-2-yl]acetic acid 2-[4-(3, 4-Dichlorophenylmethyl)-6-fluoro-3, 4-3-oxo-2H-1, 4-benzothiazin-2-yl]acetic acid 2-[4-(3, 4-Dichlorophenylmethyl)-7-fluoro-3, 4-dihydro-3-oxo-2H-1, 4-benzothiazin-2-yl]acetic acid 2-[4-(3, 4-Dichlorophenylmethyl)-8-fluoro-3, 4-dihydro-3-oxo-2H-1, 4-benzothiazin-2-yl]acetic acid 2-[4-(3, 4-Dichlorophenylmethyl)-5-methyl-3, 4-dihydro-3-oxo-2H-1, 4-benzothiazin-2-yl]acetic acid 2-[4-(3, 4-Dichlorophenylmethyl)-6-methyl-3, 4-dihydro-3-oxo-2H-1, 4-benzothiazin-2-yl]acetic acid 2-[4-(3, 4-Dichlorophenylmethyl)-7-methyl-3, 4-dihydro-3-oxo-2H-1, 4-benzothiazin-2-yl]acetic acid 2-[4-(3, 4-Dichlorophenylmethyl)-8-methyl-3, 4-dihydro-3-oxo-2H-1, 4-benzothiazin-2-yl]acetic acid 2-[4-(3, 4-Dichlorophenylmethyl)-5-ethyl-3, 4-dihydro-3-oxo-2H-1, 4-benzothiazin-2-yl]acetic acid 2-[4-(3, 4-Dichlorophenylmethyl)-6-ethyl-3, 4-dihydro-3-oxo-2H-1, 4-benzothiazin-2-yl]acetic acid Propyl 2-[4-(3, 4-dichlorophenylmethyl)-7-ethyl-3, 4-dihydro-3-oxo-2H-1, 4-benzothiazin-2-yl]acetate, 2-[4-(3, 4-.Dichlorophenylmethyl)-7-ethyl-3, 4-dihydro-3-oxo-2H-1, 4-benzothiazin-2-yl]acetic acid Isopropyl 2-[4-(3, 4-dichlorophenylmethyl)-8-ethyl-3, 4-dihydro-3-oxo-2H-1, 4-benzothiazin-2-yl]acetate 2-[4-(3, 4-Dichlorophenylmethyl)-8-ethyl-3, 4-dihydro-3-oxo-2H-1, 4-benzothiazin-2-yl]acetic acid 2-[4-(3, 4-Dichlorophenylmethyl)-6-propyl-3, 4-dihydro-3-oxo-2H-1, 4-benzothiazin-2-yl]acetic acid 2-[4-(3, 4-Dichlorophenylmethyl)-6-isopropyl-3, 4-dihydro-3-oxo-2H-1, 4-benzothiazin-2-yl]acetic acid 2-[4-(3, 4-Dichlorophenylmethyl)-7-isopropyl-3, -dihydro-3-oxo-2H-1, 4-benzothiazin-2-yl]acetic acid 2-[4-(3, 4--Dichlorophenylmethyl)-8-isopropyl-3, 4-dihydro-3-oxo-2H-1, 4-benzothiazin-2-yl]acetic acid 2-[4-(3, 4-Dichlorophenylmethyl)-6-butyl-3, 4-dihydro-3-oxo-2H-1, 4-benzothiazin-2-yl]acetic acid 2-[4-(3, 4-Dichlorophenylmethyl)-6-isobutyl-3, 4-dihydro-3-oxo-2H-1, 4-benzothiazin-2-yl]acetic acid 2-[4-(3, 4-Dichlorophenylmethyl)-6-see-butyl-3, 4-dihydro-3-oxo-2H-1, 4-benzothiazin-2-yl]acetic acid 2-[4-(3, 4-Dichlorophenylmethyl)-6-tert-butyl-3, 4-dihydro-3-oxo-2H-1, 4-benzothiazin-2-yl]acetic acid 2-[4-(3, 4-Dichlorophenylmethyl)-7-tert-butyl-3, 4-dihydro-3-oxo-2H-1, 4-benzothiazin-2-yl]acetic acid 2-[4-(3, 4-Dichlorophenylmethyl)-8-tert-butyl-3, 4-dihydro-3-oxo-2H-1, 4-benzothiazin-2-yl]acetic acid 2-[4-(3, 4-Dichlorophenylmethyl)-6-pentyl-3, 4-dihydro-3-oxo-2H-1, 4-benzothiazin-2-yl]acetic acid 2-[4-(3, 4-Dichlorophenylmethyl)-6-hexyl-3, 4-dihydro-3-oxo-2H-1, 4-benzothiazin-2-yl]acetic acid Ethyl 2-[4-(3, 4-dichlorophenylmethyl)-5-methoxy-3, 4-dihydro-3-oxo-2H-1, 4-benzothiazin-2-yl]acetate, Ethyl 2-[4-(3, 4-dichlorophenylmethyl)-6-methoxy-3, 4-dihydro-3-oxo-2H-1, 4-benzothiazin-2-yl]acetate, Ethyl 2-[4-(3, 4-dichlorophenylmethyl)-7-methoxy-3, 4-dihydro-3-oxo-2H-1, 4-benzothiazin-2-yl]acetate, Ethyl 2-[4-(3, 4-dichlorophenylmethyl)-8-methoxy-3, 4-dihydro-3-oxo-2H-1, 4-benzothiazin-2-yl]acetate, 2-[4-(3, 4-Dichlorophenylmethyl)-5-methoxy-3, 4-dihydro-3-oxo-2H-1, 4-benzothiazin-2-yl]acetic acid 2-[4-(3, 4-Dichlorophenylmethyl)-6-methoxy-3, 4-dihydro-3-oxo-2H-1, 4-benzothiazin-2-yl]acetic acid 2-[4-(3, 4-Dichlorophenylmethyl)-7-methoxy-3, 4-dihydro-3-oxo-2H-1, 4-benzothiazin-2-yl]acetic acid 2-[4-(3, 4-Dichlorophenylmethyl)-8-methoxy-3, 4-dihydro-3-oxo-2H-1, 4-benzothiazin-2-yl]acetic acid 2-[4-(3, 4-Dichlorophenylmethyl)-5-ethoxy-3, 4-dihydro-3-oxo-2H-1, 4-benzothiazin-2-yl]acetic acid 2-[4-(3, 4-Dichlorophenylmethyl)-6-ethoxy-3, 4-dihydro-3-oxo-2H-1, 4-benzothiazin-2-yl]acetic acid Butyl 2-[4-(3, 4-dichlorophenylmethyl)-7-ethoxy-3, 4-dihydro-3-oxo-2H-1, 4-benzothiazin-2-yl]acetate, 2-[4-(3, 4-Dichlorophenylmethyl)-7-ethoxy-3, 4-dihydro-3-oxo-2H-1, 4-benzothiazin-2-yl]acetic acid Isobutyl 2-[4-(3, 4-dichlorophenylmethyl)-8-ethoxy-3, 4-dihydro-3-oxo-2H-1, 4-benzothiazin-2-yl]acetate, 2-[4-(3, 4-Dichlorophenylmethyl)-8-ethoxy-3, 4-dihydro-3-oxo-2H-1, 4-benzothiazin-2-yl]acetic acid 2-[4-(3, 4-Dichlorophenylmethyl)-6-propoxy-3, 4-dihydro-3-oxo-2H-1, 4-benzothiazin-2-yl]acetic acid 2-[4-(3, 4-Dichlorophenylmethyl)-6-isopropoxy-3, 4-dihydro-3-oxo-2H-1, 4-benzothiazin-2-yl]acetic acid 2-[4-(3, 4-Dichlorophenylmethyl)-7-isopropoxy-3, 4-dihydro-3-oxo-2H-1, 4-benzothiazin-2-yl]acetic acid 2-[4-(3, 4-Dichlorophenylmethyl)-8-isopropoxy-3, 4-dihydro-3-oxo-2H-1, 4-benzothiazin-2-yl]acetic acid 2-[4-(3, 4-Dichlorophenylmethyl)-6-butoxy-3, 4-dihydro-3-oxo-2H-1, 4-benzothiazin-2-yl]acetic acid 2-[4-(3, 4-Dichlorophenylmethyl)-6-isobutoxy-3, 4-dihydro-3-oxo-2H-1, 4-benzothiazin-2-yl]acetic acid 2-[4-(3, 4-Dichlorophenylmethyl)-6-sec-butoxy-3, 4-dihydro-3-oxo-2H-1, 4-benzothiazin-2-yl]acetic acid 2-[4-(3, 4-Dichlorophenylmethyl)-6-tert-butoxy-3, 4-dihydro-3-oxo-2H-1, 4-benzothiazin-2-yl]acetic acid 2-[4-(3, 4-Dichlorophenylmethyl)-7-tert-butoxy-3, 4-dihydro-3-oxo-2H-1, 4-benzothiazin-2-yl]acetic acid 2-[4-(3, 4-Dichlorophenylmethyl)-8-tert-butoxy-3, 4-dihydro-3-oxo-2H-1, 4-benzothiazin-2-yl]acetic acid 2-[4-(3, 4-Dichlorophenylmethyl)-6-pentyloxy-3, 4-dihydro-3-oxo-2H-1, 4-benzothiazin-2-yl]acetic acid 2-[4-(3, 4-Dichlorophenylmethyl)-6-hexyloxy-3, 4-dihydro-3-oxo-2H-1, 4-benzothiazin-2-yl]acetic acid 2-[4-Benzyl-3, 4-dihydro-3-thioxo-2H-1, 4-benzothiazin-2-yl]acetic acid 2-[4-(4-Methylphenylmethyl)-3, 4-dihydro-3-thioxo-2H-1, 4-benzothiazin-2-yl]acetic acid 2-[4-(4-Methoxyphenylmethyl)-3, 4-dihydro-3-thioxo-2H-1, 4-benzothiazin-2-yl]acetic acid Ethyl 2-[4-(4-bromo-2-fluorophenylmethyl)-3, 4-dihydro-3-thioxo-2H-1, 4-benzothiazin-2-yl]acetate 2-[4-(4-Bromo-2-fluorophenylmethyl)-3, 4-dihydro-3-thioxo-2H-1, 4-benzothiazin-2-yl]acetic acid 2-[4-(4-Bromo-2-fluorophenylmethyl)-8-chloro-3, 4-dihydro-3-thioxo-2H-1, 4-benzothiazin-2-yl]acetic acid 2-[4-(4-Bromo-2-fluorophenylmethyl)-5-fluoro-3, 4-dihydro-3-thioxo-2H-1, 4-benzothiazin-2-yl]acetic acid 2-[4-(4-Bromo-2-fluorophenylmethyl)-6-methyl-3, 4-dihydro-3-thioxo-2H-1, 4-benzothiazin-2-yl]acetic acid 2-[4-(4-Bromo-2-fluorophenylmethyl)-6-ethyl-3, 4-dihydro-3-thioxo-2H-1, 4-benzothiazin-2-yl]acetic acid 2-[4-(4-Bromo-2-fluorophenylmethyl)-6-isopropyl-3, 4-dihydro-3-thioxo-2H-1, 4-benzothiazin-2-yl]acetic acid 2-[4-(4-Bromo-2-fluorophenylmethyl)-6-tert-butyl-3, 4-dihydro-3-thioxo-2H-1, 4-benzothiazin-2-yl]acetic acid 2-[4-(4-Bromo-2-fluorophenylmethyl)-7-methoxy-3, 4-dihydro-3-thioxo-2H-1, 4-benzothiazin-2-yl]acetic acid 2-[4-(4-Bromo-2-fluorophenylmethyl)-7-ethoxy-3, 4-dihydro-3-thioxo-2H-1, 4-benzothiazin-2-yl]acetic acid 2-[4-(4-Bromo-2-fluorophenylmethyl)-7-isopropoxy-3, 4-dihydro-3-thioxo-2H-1, 4-benzothiazin-2-yl]acetic acid 2-[4-(4-Bromo-2-fluorophenylmethyl)-7-tert-butoxy-3, 4-dihydro-3-thioxo-2H-1, 4-benzothiazin-2-yl]acetic acid 2-[4-(3, 4-Dichlorophenylmethyl)-3, 4-dihydro-3-thioxo-2 -1, 4-benzothiazin-2-yl]acetic acid 2-[8-Chloro-4-(3, 4-dichlorophenylmethyl)-3, 4-dihydro-3-thioxo-2H-1, 4-benzothiazin-2-yl]acetic acid 2-[4-(3, 4-Dichlorophenylmethyl)-5-fluoro-3, 4-dihydro-3-thioxo-2H-1, 4-benzothiazin-2-yl]acetic acid 2-[4-(3, 4-Dichlorophenylmethyl)-6-methyl-3, 4-dihydro-3-thioxo-2H-1, 4-benzothiazin-2-yl]acetic acid 2-[4-(3, 4-Dichlorophenylmethyl)-7-methoxy-3, 4-dihydro-3-thioxo-2H-1, 4-benzothiazin-2-yl]acetic acid 2-[4-Benzyl-3, 4-dihydro-3-oxo-2H-1, 4-benzothiazin-2-ylidene]acetic acid 2-[4-(4-Methylphenylmethyl)-3, 4-dihydro-3-oxo-2H-1, 4-benzothiazin-2-ylidene]acetic acid 2-[4-(4-Methoxyphenylmethyl)-3, 4-dihydro-3-oxo-2H-1, 4-benzothiazin-2-ylidene]acetic acid Methyl 2-[4-(4-bromo-2-fluorophenylmethyl)-3, 4-dihydro-3-oxo-2H-1, 4-benzothiazin-2-ylidene]acetate 2-[4-(4-Bromo-2-fluorophenylmethyl)-3, 4-dihydro-3-oxo-2H-1, 4-benzothiazin-2-ylidene]acetic acid 2-[4-(4-Bromo-2-fluorophenylmethyl)-8-chloro 4-dihydro-3-oxo-2H-1, 4-benzothiazin-2-ylidene]acetic acid 2-[4-(4-Bromo-2-fluorophenylmethyl)-5-fluoro-3, 4-dihydro-3-oxo-2H-1, 4-benzothiazin-2-ylidene]acetic acid 2-[4-(4-Bromo-2-fluorophenylmethyl)-6-methyl-3, 4-dihydro-3-oxo-2H-1, 4-benzothiazin-2-ylidene]acetic acid 2-[4-(4-Bromo-2-fluorophenylmethyl)-6-ethyl-3, 4-dihydro-3-oxo-2H-1, 4-benzothiazin-2-ylidene]acetic acid 2-[4-(4-Bromo-2-fluorophenylmethyl)-6-isopropyl-3, 4-dihydro-3-oxo-2H-1, 4-benzothiazin-2-ylidene]acetic acid 2-[4-(4-Bromo-2-fluorophenylmethyl)-6-tert-butyl-3, 4-dihydro-3-oxo-2H-1, 4-benzothiazin-2-ylidene]acetic acid tert-Butyl 2-[4-(4-bromo-2-fluorophenylmethyl)-7-methoxy-3, 4-dihydro-3-oxo-2H-1, 4-benzothiazin-2-ylidene]acetate 2-[4-(4-Bromo-2-fluorophenylmethyl)-7-methoxy-3, 4-dihydro-3-oxo-2H-1, 4-benzothiazin-2-ylidene]acetic acid 2-[4-(4-Bromo-2-fluorophenylmethyl)-7-ethoxy-3, 4-dihydro-3-oxo-2H-1, 4-benzothiazin-2-ylidene]acetic acid 2-[4-(4-Bromo-2-fluorophenylmethyl)-7-isopropoxy-3, 4-dihydro-3-oxo-2H-1, 4-benzothiazin-2-ylidene]acetic acid 2-[4-(4-Bromo-2-fluorophenylmethyl)-7-tert-butoxy-3, 4-dihydro-3-oxo-2H-1, 4-benzothiazin-2-ylidene]acetic acid 2-[4-(3, 4-Dichlorophenylmethyl)-3, 4-dihydro-3-oxo-2H-1, 4-benzothiazin-2-ylidene]acetic acid 2-[8-Chloro-4-(3, 4-dichlorophenylmethyl)-3, 4-dihydro-3-oxo-2H-1, 4-benzothiazin-2-ylidene]acetic acid 2-[4-(3, 4-Dichlorophenylmethyl)-5-fluoro-3, 4-dihydro-3-oxo-2H-1, 4-benzothiazin-2-ylidene]acetic acid 2-[4-(3, 4-Dichlorophenylmethyl)-6-methyl-3, 4-dihydro-3-oxo-2H-1, 4-benzothiazin-2-ylidene]acetic acid 2-[4-(3, 4-Dichlorophenylmethyl)-7-methoxy-3, 4-dihydro-3-oxo-2H-1, 4-benzothiazin-2-ylidene]acetic acid 2-[4-Benzyl-3, 4-dihydro-3-thioxo-2H-1, 4-benzothiazin-2-ylidene]acetic acid 2-[4-(4-Methylphenylmethyl)-3, 4-dihydro-3-thioxo-2H-1, 4-benzothiazin-2-ylidene]acetic acid 2-[4-(4-Methoxyphenylmethyl)-3, 4-dihydro-3-thioxo-2H-1, 4-benzothiazin-2-ylidene]acetic acid 2-[4-(4-Bromo-2-fluorophenylmethyl)-3, 4-dihydro-3-thioxo-2H-1, 4-benzothiazin-2-ylidene]acetic acid 2-[4-(4-Bromo-2-fluorophenylmethyl)-8-chloro-3, 4-dihydro-3-thioxo-2H-1, 4-benzothiazin-2-ylidene]acetic acid 2-[4-(4-Bromo-2-fluorophenylmethyl)-5-fluoro-3, 4-dihydro-3-thioxo-2H-1, 4-benzothiazin-2-ylidene]acetic acid 2-[4-(4-Bromo-2-fluorophenylmethyl)-6-methyl-3, 4-dihydro-3-thioxo-2H-1, 4-benzothiazin-2-ylidene]acetic acid 2-[4-(4-Bromo-2-fluorophenylmethyl)-6-ethyl-3, 4-dihydro-3-thioxo-2H-1, 4-benzothiazin-2-ylidene]acetic acid 2-[4-(4-Bromo-2-fluorophenylmethyl)-6-isopropyl-3, 4-dihydro-3-thioxo-2H-1, 4-benzothiazin-2-ylidene]acetic acid 2-[4-(4-Bromo-2-fluorophenylmethyl)-6-tert-butyl-3, 4-dihydro-3-thioxo-2H-1, 4-benzothiazin-2-ylidene]acetic acid 2-[4-(4-Bromo-2-fluorophenylmethyl)-7-methoxy-3, 4-dihydro-3-thioxo-2H-1, 4-benzothiazin-2-ylidene]acetic acid 2-[4-(4-Bromo-2-fluorophenylmethyl)-7-ethoxy-3, 4-dihydro-3-thioxo-2H-1, 4-benzothiazin-2-ylidene]acetic acid 2-[4-(4 -Bromo-2-fluorophenylmethyl)-7-isopropoxy-3, 4-dihydro-3-thioxo-2H-1, 4-benzothiazin-2-ylidene]acetic acid 2-[4-(4-Bromo-2-fluorophenylmethyl)-7-tert-butoxy-3, 4-dihydro-3-thioxo-2H-1, 4-benzothiazin-2-ylidene]acetic acid 2-[4-(3, 4-Dichlorophenylmethyl)-3, 4-dihydro-3-thioxo-2H-1, 4-benzothiazin-2-ylidene]acetic acid 2-[8-Chloro-4-(3, 4-dichlorophenylmethyl)-3, 4-dihydro-3-thioxo-2H-1, 4-benzothiazin-2-ylidene]acetic acid 2-[4-(3, 4-Dichlorophenylmethyl)-5-fluoro-3, 4-dihydro-3-thioxo-2H-1, 4-benzothiazin-2-ylidene]acetic acid 2-[4-(3, 4-Dichlorophenylmethyl)-6-methyl-3, 4-dihydro-3-thioxo-2H-1, 4-benzothiazin-2-ylidene]acetic acid 2-[4-(3, 4-Dichlorophenylmethyl)-7-methoxy-3, 4-dihydro-3-thioxo-2H-1, 4-benzothiazin-2-ylidene]acetic acid Ethyl 2-[4-(4-bromo-2-fluorophenylmethyl)-7-tert-butyl-3, 4-dihydro-3-oxo-2-H-1, 4-benzothiazin-2-yl]acetate 2-[4-(3, 4-Dichlorophenylmethyl)-7-tert-butyl-3, 4-dihydro-3-oxo-2-H-1, 4-benzothiazin-2-yl]acetic acid Ethyl 2-[4-(4-bromo-2-fluorophenylmethyl)-7-ethoxy-3, 4-dihydro-3-oxo-2-H-1, 4-benzothiazin-2-yl]acetate 2-[4-(4-Bromo-2-fluorophenylmethyl)-7-propoxy-3, 4-dihydro-3-oxo-2-H-1, 4-benzothiazin-2-yl]acetic acid 2-[4-(3, 4-Dichlorophenylmethyl)-7-ethoxy-3, 4-dihydro-3-oxo-2-H-1, 4-benzothiazin-2-yl]acetic acid Ethyl 2-[4-(4-bromo-2-fluorophenylmethyl)-7-propoxy-3, 4-dihydro-3-oxo-2-H-1, 4-benzothiazin-2-yl]acetate 2-[4-(3, 4-Dichlorophenylmethyl)-7-propoxy-3, 4-dihydro-3-oxo-2-H-1, 4-benzothiazin-2-yl]acetic acid Ethyl 2-[4-(4-bromo-2-fluorophenylmethyl)-7-isopropyl-3, 4-dihydro-3-oxo-2-H-1, 4-benzothiazin-2-yl]acetate 2-[4-(3, 4-Dichlorophenylmethyl)-7-isopropyl-3, 4-dihydro-3-oxo-2-H-1, 4-benzothiazin-2-yl]acetic acid Ethyl 2-[4-(4-bromo-2-fluorophenylmethyl)-7-ethyl-3, 4-dihydro-3-oxo-2-H-1, 4-benzothiazin-2-yl]acetate 2-[4-(3, 4-Dichlorophenylmethyl)-7-ethyl-3, 4-dihydro-3-oxo-2-H-1, 4-benzothiazin-2-yl]acetic acid 2-[4-(4-Bromo-2-fluorophenylmethyl)-6, 8-dimethyl-3, 4-dihydro-3-oxo-2-H-1, 4-benzothiazin-2-yl]acetic acid 2-[4-(3, 4-Dichlorophenylmethyl)-6, 8-dimethyl-3, 4-dihydro-3-oxo-2-H-1, 4-benzothiazin-2-yl]acetic acid Ethyl 2-[4-(4-bromo-2-fluorophenylmethyl)-6, 8-dimethyl-3, 4-dihydro-3-oxo-2-H-1, 4-benzothiazin-2-yl]acetate 2-[4-(4-Bromo-2-fluorophenylmethyl)-6, 7-dimethyl-3, 4-dihydro-3-oxo-2-H-1, 4-benzothiazin-2-yl]acetic acid Ethyl 2-[4-(4-bromo-2-fluorophenylmethyl)-6, 7-dimethyl-3, 4-dihydro-3-oxo-2-H-1, 4-benzothiazin-2-yl]acetate 2-[4-(3, 4-Dichlorophenylmethyl)-6, 7-dimethyl-3, 4-dihydro-3-oxo-2-H-1, 4-benzothiazin-2-yl]acetic acid 2-[4-(4-Bromo-2-fluorophenylmethyl)-6, 8-dimethoxy-3, 4-dihydro-3-oxo-2-H-1, 4-benzothiazin-2-yl]acetic acid Ethyl 2-[4-(4-bromo-2-fluorophenylmethyl)-6, 8-dimethoxy-3, 4-dihydro-3-oxo-2-H-1, 4-benzothiazin-2-yl]acetate 2-[4-(3, 4-Dichlorophenylmethyl)-6, 8-dimethoxy-3, 4-dihydro-3-oxo-2-H-1, 4-benzothiazin-2-yl]acetic acid 2-[4-(4-Bromo-2-fluorophenylmethyl)-7-methylthio-3, 4-dihydro-3-oxo-2-H-1, 4-benzothiazin-2-yl]acetic acid Ethyl 2-[4-(4-bromo-2-fluorophenylmethyl)-7-methylthio-3, 4-dihydro-3-oxo-2-H-1, 4-benzothiazin-2-yl]acetate 2-[4-(3, 4-Dichlorophenylmethyl)-7-methylthio-3, 4-dihydro-3-oxo-2-H-1, 4-benzothiazin-2-yl]acetic acid Processes for production of the compounds of the present invention represented by general formula (I) are described below in detail.

Process 1

Where X represents oxygen and $R^4$ represents an esterified carboxyl group in general formula (I), the compounds of the present invention can be prepared by reacting compounds represented by general formula (VI):

(VI)

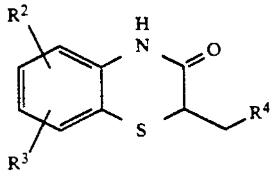

or

-continued

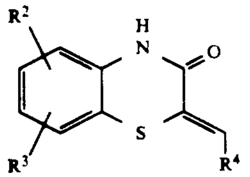

wherein $R^2$ and $R^3$ have the same significances as described above and $R^4$ represents an esterified carboxyl, or salts thereof with compounds represented by general formula (VII):

$$Y—R^1 \qquad (VII)$$

wherein $R^1$ represents general formula (II) or (III) and Y represents a halogen such as chlorine, bromine, iodine, etc., or $OSO_2R^{11}$ (wherein $R^{11}$ represents an alkyl group having 1 to 4 carbon atoms, trifluoromethyl, phenyl or a phenyl group substituted with methyl, chlorine, bromine or nitro), if necessary, under basic conditions and/or in an inert gaseous atmosphere.

Examples of the base under the basic conditions include inorganic salts or organic salts such as alkali metals such as lithium, sodium, potassium, etc.; alkaline earth metals such as calcium, etc.; alkali metal hydrides such as sodium hydride, etc., alkaline earth metal hydrides such as calcium hydride, etc., alkali metal hydroxides such as sodium hydroxide, potassium hydroxide, etc., alkali metal carbonates such as sodium carbonate, potassium carbonate, etc., alkali metal hydrogencarbonates such as sodium hydrogencarbonate, potassium hydrogencarbonate, etc., alkali metal alkoxides such as sodium methoxide, sodium ethoxide, potassium tert-butoxide, etc., alkanoic acid alkali metal salts such as sodium acetate, etc., trialkylamines such as triethylamine, etc., pyridine compounds such as pyridine, lutidine, picoline, 4-dimethylaminopyridine, etc., quinoline, etc. The inert gas refers to nitrogen and argon.

The reaction described above is carried out generally in an inert various solvent, for example, conventional solvents such as dichloromethane, methanol, ethanol, propanol, pyridine, N,N-dimethylformamide, tetrahydrofuran, dimethylsulfoxide, etc., or a mixture thereof.

Particularly preferred solvents are N,N-dimethylforniamide, tetrahydrofuran, dimethylsulfoxide, etc.

The reaction temperature is not particularly limited but the reaction is carried out generally in the range of under cooling to with heating. In the case of using, for example, sodium hydride as the base, it is preferred to set the reaction temperature in the range of −30° C. to room temperature.

The starting compounds represented by general formula (VI) are known compounds or may be readily prepared by known procedures [cf., French Patent No. 1,443,917 and Chem. Pharm. Bull., 20, 832-834, 1972].

The starting compounds represented by general formula (VII) are known compounds or may be readily prepared by known procedures [cf., Journal of Medicinal Chemistry, 34, 108-122, 1991 or Journal of Chemical Society, 3340, 1960].

Process 2

Where $R^1$ represents the group shown by general formula (III), X represents oxygen and $R^4$ represents an esterified carboxyl in general formula (I), the compounds of the present invention may also be prepared by reacting compounds represented by general formula (VIII):

(VIII)

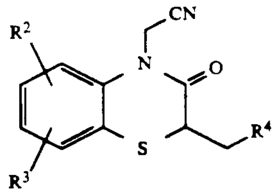

or

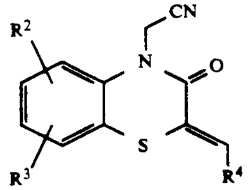

wherein $R^2$ and $R^3$ have the same significances as described above and $R^4$ represents an esterified carboxyl, with compounds represented by general formula (IX):

(IX)

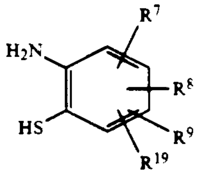

wherein $R^7$, $R^8$, $R^8$, $R^9$ and $R^{10}$ have the same significances as described above, or acid addition salts thereof.

Where the compounds represented by general formula (IX) are not acid addition salts, it is preferred to carry out the reaction in the presence of a strong acid (hydrochloric acid, etc.).

Particularly preferred solvents in the reaction described above are methanol, ethanol and propanol. In this case, it is preferred to set the reaction temperature in the range of 60° C. to reflux temperature.

Where no solvent is used, the compounds of general formula (VIII) may also be reacted with the acid addition salts (hydrochloride, etc.) of general formula (IX) by fusing them at a temperature of 130° to 180° C.

The starting compounds represented by general formula (VIII)can be prepared by reacting the compounds of general formula (VI) with general formula (X):

$$Z—CH_2CN \qquad (X)$$

wherein Z represents chlorine or bromine, in the presence of a suitable base and/or under inert gas atmosphere.

Examples of the base under the basic conditions include alkali metal hydrides such as sodium hydride, etc., alkaline earth metal hydrides such as calcium hydride, etc., alkali metal hydroxides such as sodium hydroxide, potassium hydroxide, etc., alkali metal carbonates such as sodium carbonate, potassium carbonate, etc., alkali metal hydrogencarbonates such as sodium hydrogencarbonate, potassium hydrogencarbonate, etc., alkali metal alkoxides such as sodium methoxide, sodium ethoxide, potassium tert-butoxide, etc., alkanoic acid alkali metal salts such as sodium acetate, etc. The inert gas refers to nitrogen and argon.

The reaction described above is carried out generally in an inert solvent, for example, conventional solvents such as dichloromethane, methanol, ethanol, propanol, pyridine, N,N-dimethylforamide, tetrahydrofuran, dimethylsulfoxide, etc., or a mixture thereof.

Particularly preferred solvents are N,N-dimethylformamide, tetrahydrofuran, dimethylsulfoxide, etc.

The reaction temperature is not particularly limited but preferably in the range of room temperature to 100° C.

The starting compounds represented by general formula (IX) are known compounds or may be readily prepared by known procedures [cf., Journal of Medicinal Chemistry, 34, 108-122, 1991].

Process 3

Next, where X represents sulfur and $R^4$ represents an esterified carboxyl in general formula (I), which can be prepared by reacting the compounds of the present invention prepared by Process 1 or 2 described above with thionating agents.

Preferred examples of the thionating agent is phosphorus pentasulfide or lawesson's reagent which are conventionally used to convert carbonyl group into thiocarbonyl group.

This reaction is carried out generally in an inert solvent, for example, conventional solvents such as dichloromethane, methanol, ethanol, propanol, pyridine, N,N-dimethylformamide, toluene, benzene, dioxane, etc., or a mixture thereof.

Particularly preferred solvents are aromatic hydrocarbons such as toluene, benzene, etc.

The reaction temperature is not particularly limited but the reaction is carried out generally under warming to heating preferably in the range of 80° to 120° C.

Process 4

Where $R^4$ represents carboxyl in general formula the compounds of the present invention can be prepared by hydrolyzing the compounds of the present invention prepared by Process 1, 2 or 3 described above, if necessary and desired, in the presence of a base or an acid.

Preferred examples of the base include alkali metal hydroxides such as sodium hydroxide, potassium hydroxide, etc., alkali metal carbonates such as sodium carbonate, potassium carbonate, etc. As preferred acids, there are organic acids such as formic acid, acetic acid, propionic acid, trifluoroacetic acid, benzenesulfonic acid, p-toluenesulfonic acid, etc., and inorganic acids such as hydrochloric acid, hydrobromic acid, sulfuric acid, phosphoric acid, etc.

This reaction is carried out generally in an inert conventional solvent such as water, acetone, dioxane, dichloromethane, methanol, ethanol, propanol, pyridine, N,N-dimethylformamide, etc., or a mixture thereof. Where the base or the acid is used in this reaction, it may be used as a solvent.

The reaction temperature is not particularly limited but the reaction is carried out generally in the range of under cooling to heating.

The compounds of the present invention prepared by the processes described above can be isolated and purified in a conventional manner, for example, extraction, precipitation, fractional chromatography, crystallization, recrystallization, etc.

The thus prepared compounds of the present invention may be converted into pharmaceutically suitable salts in a conventional manner, if necessary and desired.

Next, the results of pharmacological tests showing effectiveness of the compounds of the present invention represented by general formula (I) are described. Similar effects were noted also with the compounds of the present invention which are not specifically shown below.

1) Aldose reductase inhibitory activity

Preparation of enzyme standard

Aldose reductase enzyme standard was prepared from porcine crystalline lens by the method of Hayman et al. (cf., S. Hayman et al., Journal of Biological Chemistry, 240, 877-882, 1965). That is, porcine crystalline lens stored at −80° C. was homogenized in distilled water followed by centrifugation at 10,000 XG for 15 minutes. The supernatant was dissolved to make 40% ammonium sulfate solution. The supernatant centrifuged at 10,000 XG for further 10 minutes was dialyzed to 0.05 M sodium chloride solution overnight. The thus obtained dialysate was used as the enzyme standard.

Determination of activity

The activity of aldose reductase was determined by the method of Hayman et al. supra. That is, 25 μl of the enzyme solution described above and 25 ml of a drug solution in 1% DMSO having various concentrations were added to 200 μl of 40 mM phosphate buffer (pH 6.2) prepared to contain 0.4 m lithium sulfate and 0.1 MM NADPH (reduced nicotinamide adenine dinucleotide phosphate) in final concentrations and Containing 3 mM dl-glyceraldehyde as substrate, respectively. Thereafter, the mixture was reacted at 25° C. for 2 minutes and change in absorbance at 340 nm was determined using COBAS FARA II (Roche Co.). Change in absorbance was made 100% when 1% DMSO was added instead of the drug solution and the results are shown in Table 1 in terms of 50% inhibitory concentration of drug ($IC_{50}$).

The $IC_{50}$ value (M) indicates the concentration of the compounds of the present invention which inhibits the aldose reductase activity by 50%.

Compound A: 3,4-dihydro-2,8-diisopropyl-3-thioxo-2H-1,4-benzoxazine-4-acetic acid described in Japanese Patent Application Laid-Open No. 63-107970

TABLE 1

| Drug Tested | $IC_{50}$ (M) |
|---|---|
| Example | |
| 131 | $1.5 \times 10^{-8}$ |
| 187 | $9.8 \times 10^{-9}$ |
| 173 | $1.4 \times 10^{-8}$ |
| 155 | $1.4 \times 10^{-8}$ |
| 160 | $1.4 \times 10^{-8}$ |
| 166 | $9.1 \times 10^{-9}$ |
| 176 | $1.4 \times 10^{-8}$ |
| 177 | $1.6 \times 10^{-8}$ |
| 133 | $1.5 \times 10^{-8}$ |
| 139 | $1.4 \times 10^{-8}$ |
| 182 | $1.2 \times 10^{-8}$ |
| 183 | $9.5 \times 10^{-9}$ |
| 188 | $9.7 \times 10^{-9}$ |
| 189 | $9.9 \times 10^{-9}$ |
| 166 | $9.1 \times 10^{-9}$ |
| 206 | $6.8 \times 10^{-9}$ |
| 199 | $7.7 \times 10^{-9}$ |
| 202 | $8.7 \times 10^{-9}$ |
| Compound A | $2.1 \times 10^{-8}$ |

2) Activity for preventing accumulation of sorbitol in lens withdrawn from rat

The lens withdrawn from SD rats of 7 to 8 weeks age was incubated in 2.0 ml of Kreb's solution (pH 7. 4) containing 50 mM glucose and $10^{-6}$ M test drug for 4 hours. The sorbitol content formed in the tissue was assayed by the enzyme method of Bergmeyer et al. [cf., H. Y. Bergmeyer et al., Methods of Enzymatic Analysis, 3, 1323-1330, 19741 using SDH (Sorbitol dehydrogenase) and AND (β-nicotinamide adenine dinucleotide). The sorbitol content was made 100% when 1% DMSO as a solvent was added in place of the drug and the activity of the drug was determined. The results are shown in Table 2.

TABLE 2

| Drug Tested | Sorbitol Content (%) |
|---|---|
| Example | |
| 183 | 29 |
| 188 | 38 |
| 189 | 37 |
| Compound A | 56 |

3) Aldose-reductase of human origin inhibitory activity and specificity

Preparation of enzyme

The aldose reductase enzyme standard was prepared from human placenta by a partial modification of the method of VanderJagt et al. [cf., DL, VanderJagt et al., The Journal of Biological Chemistry, 265, 10912-10918, 19901.

That is, human placenta stored at −80° C. was homogenized in distilled water followed by centrifugation at 10,000 XG for 15 minutes. The supernatant was ammonium sulfate subjected to a 30%-75% fractionation and resulting pellets were resuspended in a minimum volume of 10 mM phosphate butter, and dialyzed overnight against the same. The dialysate was applied to DEAE-cellulose column. The fraction containing aldose reductase activity eluted by salt concentration gradient was dialyzed and used as aldose reductase enzyme standard. Furthermore, after fractionation with ammonium sulfate solution, the dialysate was applied to Red Sepharose CL-6B, the fraction containing aldehyde reductase activity eluted by salt concentration gradient was dialyzed and used as aldehyde reductase enzyme standard.

Determination of activity

The activity of aldose reductase was determined by the method of Hayman et al. [cf., Journal of Biological Chemistry, 240, 877-882, 1965]. That is, 25 μl of the enzyme solution described above and 25 μl of a drug solution in 1% DMSO having various concentrations were added to 200 μl of 40 Mm phosphate buffer (pH 6.2) prepared to contain 0.4 M lithium sulfate and 0.1 mM NADPH (reduced nicotinamide adenine dinucleotide phosphate) in final concentrations and containing 3 mM dl-glyceraldehyde as substrate, respectively. Thereafter, the mixture was reacted at 25° C. for 2 minutes and chance in absorbance at 340 nm was determined using COBAS FARA II (Roche co.). The change in absorbance was made 100% when 1% DMSO was added instead of the drug solution and the results are shown in Table 1 in terms of 50% inhibitory concentration of drug ($IC_{50}$).

The aldehyde reductase activity was determined by the method of Bhatnagar et al. [cf., A. Bhatnagar et al., Biochemical Pharmacology, 39, 1115-1124, 1990]. That is, the activity was determined in a manner similar to the case of determining aldose reductase activity, using 200 mM phosphate buffer (pH 7.0) prepared to contain 0.1 mM NADPH in a final concentration and 15 mM glucuronate as substrate. The result are shown in Table 3.

The test compounds show extremely potent activity also to aldose reductase of human origin but have a very weak inhibitory activity to aldehyde reductase which is very similar enzymologically. The test compounds are thus characterized by extremely high specificity to aldose reductase.

TABLE 3

| Test Compound | $IC_{50}$ (nM) HPAP | 10 μM inhibition % HPALR | Ratio HPALR/HPAR |
|---|---|---|---|
| Example | | | |
| 183 | 10 | 19.3 | >1000 |
| 188 | 14 | 19.1 | >714 |
| 165 | 12 | 32.9 | >833 |
| 189 | 9.3 | 18.5 | >1075 |
| 167 | 13 | 28.6 | >769 |
| Tolrestat | 21 | 95.7(0.55)* | 26 |

HPAR: human placenta aldose reductase
HPALR: human placenta aldehyde reductase
*$IC_{50}$: μM 4) Inhibitory activity of accumulation of tissue sorbitol in streptozatocini-induced diabetic rats.

Sprague-Dawley rats (male,6 weeks of age, one group composed of 5 to 6 rats), fasted overnight, were made diabetic by single intravenous injection of 60 mg/kg body weight of streptozotocin (SIGMA Co. ), which had been freshly dissolved in normal saline solution.

The compound was orally administered in the form of 0.5% carboxymethylcellulose suspension in a dose of 30 mg/kg 4, 8 and 24 hours after the injection of streptozotocin. During the test, rats were free access to feed and water. Three hours after the final administration, the sorbitol contens in tissues (red blood cell, sciatic nerve, lens) Were determined by the enzyme method of Bergmeyer et al. [cf., H. Y. Bergmeyer et al., Methods of Enzymatic Analysis, 3, 1323-1330, 1974], using SDH (sorbitol dehydrogenase) and AND (β-nicotinamide adenine dinucleotide). The results are shown by percentage (%) when the value obtained with control group administered with 0.5% carboxymethylcellulose solution as a solvent instead of the compound was made 100%. The results are shown in Table 4.

TABLE 4

| Test Compound | Accumulation of Tissue Sorbitol (%)[1] Red Blood Cell | Nerve | Lens |
|---|---|---|---|
| Example | | | |
| 158 | 39.2** | 33.1** | 58.4* |
| 155 | 0.0** | 7.0** | 36.8** |
| 154 | 3.3** | 18.6** | 59.0* |
| 183 | 25.8** | 3.1** | 39.1** |
| 188 | 15.7** | 0.0** | 32.5** |
| 209 | 24.7** | 3.1** | 25.2** |
| 189 | 16.6** | 1.1** | 30.7** |
| 208 | 22.9** | 0.0** | 31.5** |
| Compound A | 53.7* | 54.9** | 87.3 |

[1]Control was made 100%.
Tukey's Multiple Range Test:
*$p < 0.05$
**$p < 0.01$

Next, safety of the compounds of the present invention was verified by the following test.

After normal ICR strain mice (male, 7 weeks age, 5 mice being into one group) was fasted for 18 hours, each compound (300 mg/kg) of Examples 1311, 132, 134, 156, 173, 179, 183 and 188 was orally administered in the form of 0.5% carboxymethylcellulose suspension. In the control group, 0.5% carboxymethylcellulose solution alone was orally administered. The mice were observed for 14 days. During the observation, mice were free access to feed and water.

As the result, none of the mice administered with the compounds of Examples 131, 132, 134, 156, 173, 179, 183 and 188 was dead and the body weight was progressed as in the control group.

The compounds of the present invention possess an excellent aldose reductase inhibitory activity and are effective for the prevention and treatment of diabetic complications such as diabetic neuropathy, nephropathy, retinopathy, cataract, etc. Where the compounds of the present invention are administered for the purpose of treatment or prevention of the diseases described above, the compounds may be administered orally or non-orally.

The compounds of the present invention or salts thereof may be provided in the form of solid preparations, semi-solid preparations and liquid preparations together with organic or inorganic carriers and/or excipients suited for external, internal or topical application. The compounds of the present invention may be used to provide suitable dosage form such as a tablet, a pellet, a capsule, a suppository, liquid, an emulsion, a suspension, etc., together with non-toxic and pharmacologically acceptable auxiliary components. Examples of such auxiliary components include water, glucose, lactose, gelatin, mannitol, starch paste, magnesium trisilicate, corn starch, keratin, colloidal silica, potato starch, urea, etc., which can be effectively used to prepare solid, semi-solid or liquid preparations. The preparations may further contain such auxiliary agents as a stabilizer, a thickener, a coloring agent and an aromatic, etc. In order to preserve the activity of the compounds of the present invention, a preservative may also be contained. The compounds of the present invention should be contained in an amount sufficient to cause the desired therapeutic effect against the progress or condition of related diseases.

Where the compounds of the present invention are administered to human, they may be administered by way of injection or eye drop or, orally.

Dose of the compounds of the present invention may vary depending upon age, body weight, condition, desired therapeutic effect, route of administration, period for administration, etc. but in the case of oral administration, it is preferred to administer the compounds of the present invention generally in a dose of 1 to 2000 mg/day, preferably in the range of 10 to 600 mg/day, once to 3 times a day.

Hereafter the present invention is described in more detail with reference to the following examples, that by no means limit the scope of the invention.

REFERENCE EXAMPLE 1

Ethyl 2-(4-cyanomethyl-3,4-dihydro-3-oxo-2H-1,4-benzothiazin-2-yl)acetate

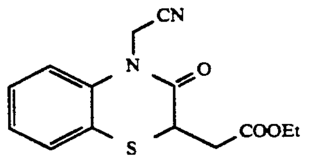

After 1.82 g of ethyl 2-(3,4-dihydro-3-oxo-2H-1,4-benzothiazin-2-yl)acetate, 1.31 g of bromoacetonitrile and 146 mg of potassium iodide were dissolved in dimethylsulfoxide (18 ml), 1.50 g of potassium carbonate was added to the solution. The mixture was stirred at room temperature for 40 hours. After saturated ammonium chloride aqueous solution was added to the reaction mixture, the mixture was extracted with ethyl acetate. After the organic phase was washed with saturated sodium chloride aqueous solution, the organic layer was dried over anhydrous magnesium sulfate and the solvent was distilled off. The resulting semicrystalline residue was dissolved in benzene. After insoluble matters were filtered off, the solvent was distilled off. Isopropyl ether was added to the residue for crystallization to give 1.74 g of the title compound. The structural formula and physical data of this compound are shown in Table 5.

REFERENCE EXAMPLES 2 THROUGH 14

In a manner substantially similar to Reference Example 1, the compounds shown in Table 5 and 6 were obtained.

Together with the compound obtained in Reference Example 1, the structural formulae and physical data of these compounds are shown in Table 5 and 6.

TABLE 5

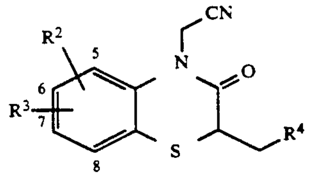

| Ref. Ex. | $R^2$, $R^3$ | $R^4$ | NMR ($CDCl_3$): δ | MS (EI) m/z |
|---|---|---|---|---|
| 1 | H | —COOEt | 1.27(3H, t), 2.58(1H, dd), 3.03(1H, dd), 3.94(1H, dd), 4.18(2H, q), 4.75(1H, d), 4.94(1H, d), 7.10~7.41(4H, m) | 290, 216 |
| 2 | 6-Me | —COOEt | 1.28(3H, t), 2.41(3H, s), 2.58(1H, dd), 3.05(1H, dd), 3.94(1H, dd), 4.20(2H, q), 4.74(1H, d), 4.92(1H, d), 6.94~7.30(3H, m) | 304, 230 |
| 3 | 5-F | —COOMe | 2.64(1H, dd), 3.14(1H, dd), 3.75(3H, s), 3.91(1H, dd), 4.76(1H, dd), 4.85(1H, dd), 7.11~7.25(3H, m) | 294, 234 |
| 4 | 7-F | —COOEt | 1.29(1H, t), 2.60(1H, dd), 3.07(1H, dd), 3.97(1H, dd), 4.21(2H, q), 4.73(1H, d), 4.93(1H, d), 7.08~7.21(3H, m) | 308, 234 |

TABLE 5-continued

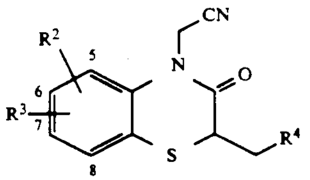

| Ref. Ex. | $R^2$, $R^3$ | $R^4$ | NMR ($CDCl_3$): δ | MS (EI) m/z |
|---|---|---|---|---|
| 5 | 7-Me | —COOEt | 1.28(3H, t), 2.33(3H, s), 2.59(1H, dd), 3.05(1H, dd), 3.95(1H, dd), 4.20(2H, q), 4.75(1H, d), 4.89(1H, d), 7.06~7.22(3H, m) | 304, 230 |
| 6 | 7-OMe | —COOEt | 1.28(3H, t), 2.59(1H, dd), 3.06(1H, dd), 3.81(3H, s), 3.96(1H, dd), 4.20(2H, q), 4.74(1H, d), 4.89(1H, d), 6.86~7.14(3H, m) | 320, 246 |
| 7 | 6,8-F | —COOEt | 1.29(3H, t), 2.63(1H, dd), 3.07(1H, dd), 3.94(1H, dd), 4.21(2H, q), 4.73(1H, d), 4.93(1H, d), 6.73~6.84(2H, m) | 326, 252 |
| 8 | 6-F | —COOEt | 1.28(3H, t), 2.59(1H, dd), 3.06(1H, dd), 3.95(1H, dd), 4.20(2H, q), 4.73(1H, d), 4.92(1H, d), 6.85~6.99(2H, m), 7.39(1H, dd) | 308, 234 |
| 9 | 8-F | —COOEt | 1.29(3H, t), 2.63(1H, dd), 3.07(1H, dd), 3.95(1H, dd), 4.21(2H, q), 4.76(1H, d), 4.96(1H, d), 6.94~7.39(3H, m) | 308, 234 |
| 10 | 6-$CF_3$ | —COOEt | 1.29(3H, t), 2.62(1H, dd), 3.09(1H, dd), 3.99(1H, dd), 4.21(2H, q), 4.80(1H, d), 4.97(1H, d), 7.39(1H, s), 7.40(1H, d), 7.56(1H, d) | 358, 284 |
| 11 | 6-OMe | —COOEt | 1.28(3H, t), 2.58(1H, dd), 3.04(1H, dd), 3.85(3H, s), 3.93(1H, dd), 4.20(2H, q), 4.74(1H, d), 4.91(1H, d), 6.70(1H, dd), 6.76(1H, d), 7.46(1H, d) | 320, 246 |

TABLE 6

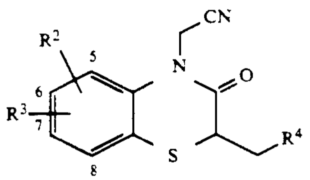

| Ref. Ex. | $R^2$, $R^3$ | $R^4$ | NMR ($CDCl_3$): δ | MS (EI) m/z |
|---|---|---|---|---|
| 12 | 7-Cl | —COOEt | 1.29(3H, t), 2.60(1H, dd), 3.06(1H, dd), 3.97(1H, dd), 4.21(2H, q), 4.74(1H, d), 4.91(1H, d), 7.11~7.43(3H, m) | 326, 324, 252, 250 |
| 13 | 7-$CF_3$ | —COOEt | 1.29(3H, t), 2.62(1H, dd), 3.09(1H, dd), 4.00(1H, dd), 4.21(2H, q), 4.78(1H, d), 4.97(1H, d), 7.26~7.70(3H, m) | 358, 284 |
| 14 | 7-Br | —COOEt | 1.29(3H, t), 2.60(1H, dd), 3.06(1H, d), 3.96(1H, dd), 4.20(2H, q), 4.74(1H, d), 4.91(1H, d), 7.05~7.57(3H, m) | 370, 368, 296, 294 |

EXAMPLE 1

Ethyl 2-[4-(5-fluorobenzothiazol-2-yl)methyl-3,4-dihydro-3-oxo-2H-1,4-benzothiazin-2-yl]acetate

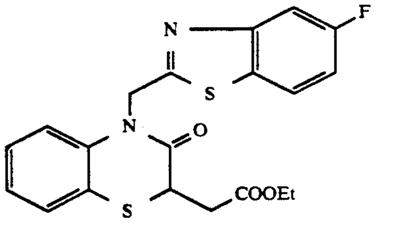

Under ice cooling, 1.01 g of ethyl 2-(3,4-dihydro-3-oxo-2H-1,4-benzothiazin-2-yl)acetate was added to a suspension of 176 mg of sodium hydride (60% in mineral oil) in 7 ml of N,N-dimethylformamide. The mixture was stirred for 30 minutes. After a solution of 1.08 g of 2-bromomethyl-5-fluorobenzothiazole in 3 ml of N,N-dimethylformamide was added dropwise to the mixture, the mixture was stirred at room temperature overnight. Thereafter the reaction mixture was poured onto ice water, and then extracted with ethyl acetate. The ethyl acetate layer was washed with water. After the drying of the organic layer over anhydrous magnesium sulfate, the solvent was distilled off. The resulting oily residue was purified by silica gel chromatography to give 1.11 g of the title compound. The structural formula and physical data of this compound are shown in Table 7.

EXAMPLES 2 THROUGH 19

In a manner substantially similar to Example 1, the compounds shown in Tables 7 and 8 were obtained.

Together with the compound obtained in Example 1, the structural formulae and physical data of these compounds are shown in Tables 7 and 8.

TABLE 7

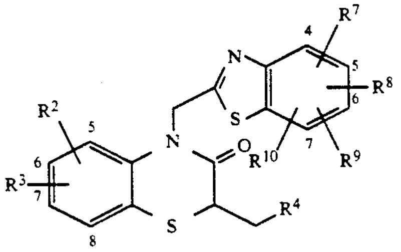

| Ex. | $R^7$, $R^8$, $R^9$, $R^{10}$ | $R^2$, $R^3$ | $R^4$ | NMR ($CDCl_3$): δ | MS (EI) m/z |
|---|---|---|---|---|---|
| 1 | 5-F | H | —COOEt | 1.28(3H, s), 2.64(1H, dd), 3.12(1H, dd), 4.05(1H, dd), 4.21(2H, q), 5.48(1H, d), 5.61(1H, d), 7.01～7.76(7H, m) | 416, 250 |
| 2 | 5-F | 6-Me | —COOEt | 1.20(3H, t), 2.22(3H, s), 2.55(1H, dd), 3.02(1H, dd), 3.94(1H, dd), 4.13(2H, q), 5.41(1H, d), 5.52(1H, d), 6.77～7.69(6H, m) | 430, 264 |
| 3 | 5-F | 7-OEt | —COOEt | 1.28(3H, t), 1.38(3H, t), 2.63(1H, dd), 3.11(1H, dd), 3.97(2H, q), 4.05(1H, dd), 4.21(2H, q), 5.46(1H, d), 5.56(1H, d), 6.73～7.76(6H, m) | 460, 294 |
| 4 | 5-F | 6,8-Me | —COOEt | 1.27(3H, t), 2.25(3H, s), 2.31(3H, s), 2.63(1H, dd), 3.12(1H, dd), 3.97(1H, dd), 4.20(2H, q), 5.46(1H, d), 5.60(1H, d), 6.78(1H, s), 6.99(1H, s), 7.08～7.74(3H, m) | 444, 278 |
| 5 | 5-F | 6-F | —COOMe | 2.65(1H, dd), 3.13(1H, dd), 3.74(3H, s), 4.02(1H, dd), 5.43(1H, d), 5.58(1H, d), 6.74～7.76(6H, m) | 420, 254 |
| 6 | 7-F | H | —COOEt | 1.25(3H, t), 2.64(1H, dd), 3.12(1H, dd), 4.05(1H, dd), 4.21(2H, q), 5.51(1H, d), 5.61(1H, d), 7.01～7.83(7H, m) | 416, 250 |
| 7 | 5-$CF_3$ | H | —COOEt | 1.28(3H, t), 2.65(1H, dd), 3.12(1H, dd), 4.06(1H, dd), 4.12(2H, q), 5.52(1H, d), 5.65(1H, d), 7.02～8.28(7H, m) | 466, 250 |
| 8 | 5-Cl | H | —COOEt | 1.28(3H, t), 2.64(1H, dd), 3.11(1H, dd), 4.05(1H, dd), 4.21(2H, q), 5.48(1H, d), 5.61(1H, d), 7.02～8.00(7H, m) | 434, 432, 250 |
| 9 | 5-Cl | 6-Me | —COOEt | 1.28(3H, t), 2.30(3H, s), 2.62(1H, dd), 3.09(1H, dd), 4.02(1H, dd), 4.21(2H, q), 5.49(1H, d), 5.59(1H, d), 6.86～8.00(6H, m) | 448, 446, 264 |

TABLE 8

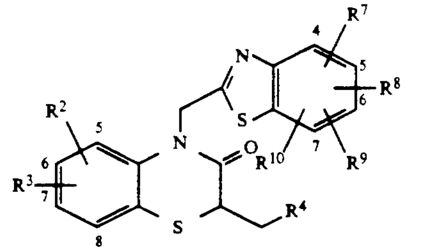

| Ex. | $R^7$, $R^8$, $R^9$, $R^{10}$ | $R^2$, $R^3$ | $R^4$ | NMR ($CDCl_3$): δ | MS (EI) m/z |
|---|---|---|---|---|---|
| 10 | 5-Cl | 7-Me | —COOEt | 1.28(3H, t), 2.27(3H, s), 2.63(1H, dd), 3.10(1H, dd), 4.03(1H, dd), 4.21(2H, q), 5.48(1H, d), 5.57(1H, d), 6.99~7.98(6H, m) | 448, 446, 264 |
| 11 | 5-Cl | 8-Me | —COOEt | 1.28(3H, t), 2.36(3H, s), 2.64(1H, dd), 3.13(1H, dd), 3.99(1H, dd), 4.21(2H, q), 5.46(1H, d), 5.61(1H, d), 6.50~7.98(6H, m) | 448, 446, 264 |
| 12 | 5-Cl | 6-OMe | —COOEt | 1.27(3H, t), 2.61(1H, dd), 3.08(1H, dd), 3.76(3H, s), 4.00(1H, dd), 4.20(2H, q), 5.47(1H, d), 5.58(1H, d), 6.59~7.99(6H, m) | 464, 462, 280 |
| 13 | 5-Cl | 7-OMe | —COOEt | 1.28(3H, t), 2.63(1H, dd), 3.11(1H, dd), 3.76(3H, s), 4.04(1H, dd), 4.21(2H, q), 5.47(1H, d), 5.56(1H, d), 6.74~7.99(6H, m) | 464, 462, 280 |
| 14 | 5-Cl | 7-OEt | —COOEt | 1.28(3H, t), 1.38(3H, t), 2.63(1H, dd), 3.11(1H, dd), 3.97(2H, q), 4.04(1H, dd), 4.21(2H, q), 5.47(1H, d), 5.56(1H, d), 6.73~8.00(6H, m) | 478, 476, 294 |
| 15 | 5-Cl | 8-Cl | —COOEt | 1.19(3H, t), 2.58(1H, dd), 3.04(1H, dd), 3.94(1H, dd), 4.13(2H, q), 5.33(1H, d), 5.52(1H, d), 7.05~7.89(6H, m) | 468, 466, 286, 284 |
| 16 | 6-OMe | H | —COOEt | 1.28(3H, t), 2.63(1H, dd), 3.12(1H, dd), 3.84(3H, s), 4.05(1H, dd), 4.21(2H, q), 5.46(1H, d), 5.58(1H, d), 7.00~7.99(7H, m) | 428, 250 |
| 17 | 4,6-F | H | —COOEt | 1.29(3H, t), 2.64(1H, dd), 3.11(1H, dd), 4.04(1H, dd), 4.22(2H, q), 5.50(1H, d), 5.62(1H, d), 6.94~7.39(6H, m) | 434, 250 |
| 18 | 6,7-F | 6-Me | —COOEt | 1.28(3H, t), 2.30(3H, s), 2.63(1H, dd), 3.10(1H, dd), 4.03(1H, dd), 4.21(2H, q), 5.48(1H, d), 5.57(1H, d), 6.86~7.77(5H, m) | 448, 264 |
| 19 | 5-F | 6,8-F | —COOEt | 1.20(3H, t), 2.57(1H, dd), 3.03(1H, dd), 4.93(1H, dd), 4.14(2H, q), 5.34(1H, d), 5.51(1H, d), 6.57~7.72(5H, m) | 452, 286 |

EXAMPLE 20

Ethyl 2-[4-(4-bromo-2-fluorophenylmethyl)-3,4-dihydro-3-oxo-2H-1,4-benzothiazin-2-yl]acetate

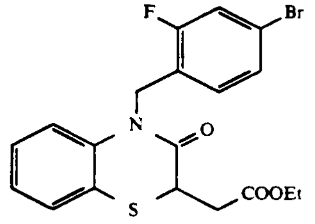

After 1.56 g of ethyl 2-(3,4-dihydro-3-oxo-2H-1,4-benzothiazin-2-yl)acetate was dissolved in 15 ml of N,N-dimethylformamide, the solution was stirred under ice cooling. To the solution was added sodium hydride (60% in oil, 220 mg). The mixture was stirred for 30 minutes. A solution of 1.48 g of 4-bromo-2-fluorobenzylbromide in 3 ml of N,N-dimethylformamide was added to the mixture. The stirring was continued for an hour under ice-cooling, the mixture was poured onto ice water, and extracted with ethyl acetate.

The ethyl acetate layer was washed with water. After the drying of the organic layer over anhydrous magnesium sulfate, the solvent was distilled off. The resulting oily residue was purified by silica gel chromatography to give 1.56 g of ethyl 2-[4-(4-bromo-2-fluorophenylmethyl)-3,4-dihydro-3-oxo-2H-1,4-benzothiazin-2-yl]acetate as colorless powders. The structural formula and physical data of this compound are shown in Table 9.

EXAMPLES 21 THROUGH 61

In a manner substantially similar to Example 20, the compounds shown in Table 9 through 13 were obtained.

Together with the compound obtained in Example 20, the structural formulae and physical data of these compounds are shown in Tables 9 through 13.

TABLE 9

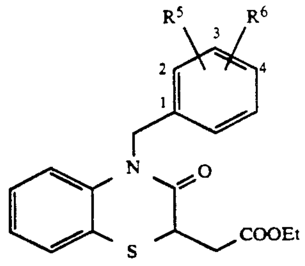

| Ex. | $R^5$ | $R^6$ | melting Point (°C.) | NMR ($CDCl_3$) δ | MS (EI) m/z |
|---|---|---|---|---|---|
| 20 | 2-F | 4-Br | 84~86 | 1.19(3H, t), 2.55(1H, dd), 3.01 (1H, dd), 3.93(1H, dd), 4.11(2H, q), 5.09(1H, d), 5.16(1H, d), 6.82~7.30(7H, m) | 437, 439, 250 |
| 21 | 3-Cl | 4-Cl | | 1.26(3H, t), 2.65(1H, dd), 3.11 (1H, dd), 4.04(1H, dd), 5.12(1H, d), 5.19(1H, d), 6.85~7.52(7H, m) | 411, 409, 250 |
| 22 | H | H | | 1.27(3H, t), 2.64(1H, dd), 3.12 (1H, dd), 4.04(1H, dd), 4.20 (1H, q), 5.16(1H, d), 5.28(1H, dd), 6.96~7.37(9H, m) | 341, 250 |
| 23 | 4-$OCH_3$ | H | | 1.26(3H, t), 2.61(1H, dd), 3.13 (1H, dd), 3.74(3H, s), 4.06(1H, dd), 4.22(2H, q), 5.14(1H, d) 5.23 (1H, d), 6.75~7.38(8H, m) | 371, 250, 121 |
| 24 | 4-tert-Bu | H | | 1.24(3H, t), 1.27(9H, s), 2.63 (1H, dd), 3.11(1H, dd), 4.03 (1H, dd), 4.19(2H, q), 5.09(1H, d), 5.25(1H, d), 6.96~7.36(8H, m) | 397, 250 |
| 25 | 4-$CH_3$ | H | | 1.28(3H, t), 2.30(3H, s), 2.62 (1H, dd), 3.11(1H, dd), 4.03 (1H, dd), 4.17(2H, q), 5.11(1H, d), 5.23(1H, d), 6.96~7.36(8H, m) | 355, 250 |
| 26 | 3-CN | H | 102~104 | 1.28(3H, t), 2.65(1H, dd), 3.10 (1H, dd), 4.03(1H, dd), 4.21 (2H, q), 5.21(1H, d), 5.29(1H, d), 6.83~7.54(8H, m) | 366, 250 |
| 27 | 3-$CF_3$ | H | | 1.26(3H, t), 2.64(1H, dd), 3.11 (1H, dd), 4.03(1H, dd), 4.19 (2H, q), 5.22(1H, d) 5.31(1H, d), 6.88~7.62(8H, m) | 409, 250 |
| 28 | 4-Br | H | | 1.27(3H, t), 2.63(1H, dd), 3.10(1H, dd), 4.01(1H, dd), 4.20(2H, q), 5.12(1H, d), 5.20(1H, d), 6.96~7.44(8H, m) | 421, 419, 250 |

TABLE 10

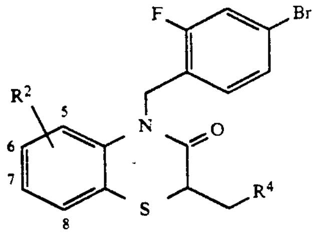

| Ex. | $R^2$ | $R^4$ | melting Point (°C.) | NMR ($CDCl_3$) δ | MS (EI) m/z |
|---|---|---|---|---|---|
| 29 | 5-Cl | —COOEt | | 1.27(3H, t), 2.59(1H, dd), 3.08(1H, dd), 3.80(1H, dd), 4.19(2H, q), 5.19(1H, d), 5.42(1H, d), 6.89~7.41(6H, m) | 473, 471, 284 |
| 30 | 5-F | —$COOCH_3$ | 71~73 | 2.63(1H, dd), 3.13(1H, dd), 3.74(3H, s), 3.90(1H, dd), 5.09(1H, d), 5.40(1H, d), 6.92~7.18(6H, m) | 443, 441, 254 |
| 31 | 5-$CH_3$ | —COOEt | | 1.27(3H, t), 2.39(3H, s), 2.58(1H, dd), 3.07(1H, dd), 3.79(1H, dd), 4.19(2H, q), 4.81(1H, d), 5.35(1H, d), 6.95~7.23(6H, m) | 453, 451, 264 |

TABLE 10-continued

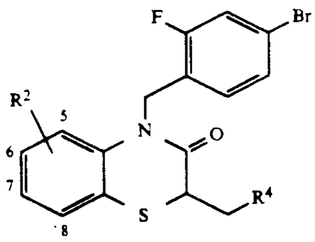

| Ex. | $R^2$ | $R^4$ | melting Point (°C.) | NMR ($CDCl_3$) δ | MS (EI) m/z |
|---|---|---|---|---|---|
| 32 | 5-$OCH_3$ | —COOEt | 116~118 | 1.27(3H, t), 2.59(3H, s), 3.10(1H, dd), 3.77(3H, s), 3.84(1H, dd), 4.18(2H, q), 5.20(1H, d) 5.30(1H, d), 6.73~7.12(6H, m) | 469, 467, 280 |
| 33 | 6-Cl | —$COOCH_3$ | | 2.63(1H, dd), 3.10(1H, dd), 3.74(3H, s), 3.98(1H, dd), 5.18(2H, s), 6.84~7.33(6H, m) | 459, 457, 270 |
| 34 | 6-F | —$COOCH_3$ | | 2.63(1H, dd), 3.10(1H, dd), 3.74(3H, s), 3.99(1H, dd), 5.18(2H, s), 6.72~7.35(6H, m) | 443, 441, 264 |
| 35 | 6-$CH_3$ | —COOEt | | 1.27(3H, t), 2.61(1H, dd), 2.61(1H, dd), 3.07(1H, dd), 3.98(1H, dd), 4.19(2H, q), 5.19(2H, s), 6.80~7.25(6H, m) | 453, 451, 264 |
| 36 | 6-$OCH_3$ | —COOEt | | 1.27(3H, t), 2.61(1H, dd), 3.06(1H, dd), 3.72(3H, s), 3.97(1H, dd), 4.19(2H, q), 5.20(2H, s), 6.56~7.27(6H, m) | 469, 467, 280 |

TABLE 11

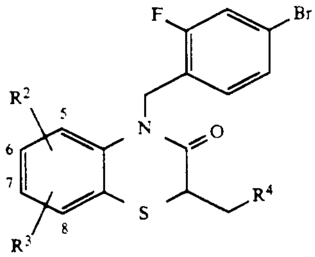

| Ex. | $R^2$ | $R^3$ | $R^4$ | melting Point (°C.) | NMR ($CDCl_3$) δ | MS (EI) m/z |
|---|---|---|---|---|---|---|
| 37 | 7-Cl | H | —COOEt | | 1.28(3H, t), 2.63(1H, dd), 3.08(1H, dd), 4.00(1H, dd), 4.20(2H, q), 5.19(2H, s), 6.89~7.35(6H, m) | 473, 471, 284 |
| 38 | 7-F | H | —COOEt | | 1.28(3H, t), 2.62(1H, dd), 3.09(1H, dd), 4.01(1H, dd), 4.21(2H, q), 5.19(2H, s), 6.88~7.25(6H, m) | 457, 455, 268 |
| 39 | 7-$CH_3$ | H | —COOEt | | 2.34(3H, s), 2.71(1H, dd), 3.18(1H, dd), 3.81(3H, s), 4.07(1H, dd), 5.26(2H, s), 6.90~7.34(6H, m) | 439, 437, 250 |
| 40 | 7-$OCH_3$ | H | —COOEt | | 1.28(3H, t), 2.62(1H, dd), 3.09(1H, dd), 3.76(3H, s), 4.01(1H, dd), 4.20(2H, q), 5.18(2H, s) 6.69~7.26(6H, m) | 469, 467, 280 |
| 41 | 7-Et | H | —COOEt | | 1.19(3H, t), 1.28(3H, t), 2.57(2H, q), 2.63(1H, dd), 3.09(1H, dd), 4.01(1H, dd), 4.20(2H, q), 5.16(1H, d), 5.22(1H, d), 6.86~7.26(6H, m) | 465, 463, 278 |
| 42 | 7-iso-Pr | H | —COOEt | | 1.20(6H, d), 1.27(3H, t), 2.63(1H, dd), 2.83(1H, Hep), 3.10(1H, dd), 4.02(1H, dd), 4.20(2H, q), 5.14(1H, d), 5.18(1H, d), 6.86~7.25(6H, m) | 481, 479, 292 |
| 43 | 7-tert-Bu | H | —COOEt | | 1.27(9H, s), 1.27(3H, t), 2.63(1H, dd), 3.11(1H, dd), 4.03(1H, dd), 4.20(2H, q), | 495, 493, 306, |

TABLE 11-continued

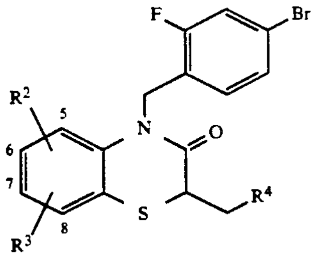

| Ex. | $R^2$ | $R^3$ | $R^4$ | melting Point (°C.) | NMR ($CDCl_3$) δ | MS (EI) m/z |
|---|---|---|---|---|---|---|
| | | | | | 5.13(1H, d), 5.23(1H, d), 6.87～7.35(6H, m) | |

TABLE 12

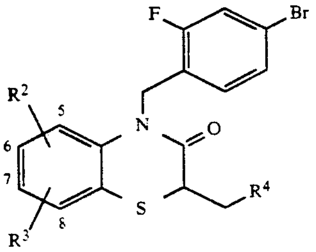

| Ex. | $R^2$ | $R^3$ | $R^4$ | melting Point (°C.) | NMR ($CDCl_3$) δ | MS (EI) m/z |
|---|---|---|---|---|---|---|
| 44 | 7-OEt | H | —COOEt | | 1.28(3H, t), 1.38(3H, t), 2.62 (1H, dd), 3.08(1H, dd), 3.95 (1H, dd), 4.00(2H, q), 4.20 (2H, q), 5.17(2H, s), 6.73～7.25(6H, m) | 483, 481, 294 |
| 45 | 7-OPr | H | —COOEt | 102～103 | 1.01(3H, t), 1.28(3H, t), 1.77(2H, m), 2.62(1H, dd), 3.08(1H, dd), 3.85(2H, t), 4.01(1H, dd), 4.20(2H, q), 5.18(2H, s), 6.67～7.26(6H, m) | 497, 495, 308 |
| 46 | 7-$SCH_3$ | H | —COOEt | | 1.28(3H, t), 2.44(3H, s), 2.62(1H, dd), 3.09(1H, dd), 4.01(1H, dd), 4.20(2H, q), 5.19(2H, s), 6.87～7.30(6H, m) | 485, 483 296 |
| 47 | 8-Cl | H | —COOEt | | 1.29(3H, t), 2.67(1H, dd), 3.12(1H, dd), 4.00(1H, dd), 4.21(2H, q), 5.16(1H, d), 5.24(1H, d), 6.89～7.26(6H, m) | 473, 471, 284 |
| 48 | 8-$CH_3$ | H | —COOEt | | 1.28(3H, t), 2.36(3H, s), 2.64(1H, dd), 3.11(1H, dd), 3.95(1H, dd), 4.20(2H, q), 5.16(1H, d), 5.25(1H, d), 6.83～7.24(6H, m) | 453, 451 264 |
| 49 | 6-$CH_3$ | 8-$CH_3$ | —COOEt | | 1.28(3H, t), 2.23(3H, s), 2.31(3H, s), 2.62(1H, dd), 3.09(1H, dd), 3.92(1H, dd), 4.20(2H, q), 5.16(1H, d), 5.21(1H, d), 6.67(1H, s), 6.76(1H, s), 6.91～7.26(6H, m) | 467, 465, 278 |
| 50 | 6-$CH_3$ | 7-$CH_3$ | —COOEt | | 1.27(3H, t), 2.17(6H, s), 3.06 (1H, dd), 3.98(1H, dd), 4.19 (2H, q), 5.18(1H, s), 6.76～7.26(6H, m) | 467, 465, 278 |
| 51 | 5-$OCH_3$ | 7-$OCH_3$ | —COOEt | | 1.27(3H, t), 2.64(1H, dd), 3.08 (1H, dd), 3.72(3H, s), 3.85 (3H, s), 3.92(1H, dd), 4.19 (2H, q), 5.18(1H, d), 5.21 (1H, d), 6.23(2H, s), 6.94～7.27(3H, m) | 499, 497, 310, 293 |

TABLE 13

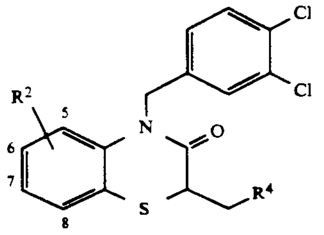

| Ex. | $R^2$ | $R^4$ | melting Point (°C.) | NMR ($CDCl_3$) δ | MS (EI) m/z |
|---|---|---|---|---|---|
| 52 | 5-Cl | $-COOCH_3$ | | 2.61(1H, dd), 3.12(1H, dd), 3.72(3H, s), 3.79(1H, dd), 5.07(1H, d), 5.51(1H, d), 6.93~7.32(6H, m) | 431, 429, 270 |
| 53 | 5-F | $-COOCH_3$ | 74~75 | 2.64(1H, dd), 3.14(1H, dd), 3.75(3H, s), 3.89(1H, dd), 4.92(1H, d), 5.47(1H, d), 6.91~7.29(6H, m) | 415, 413, 254 |
| 54 | $5-OCH_3$ | −COOEt | | 1.27(3H, t), 2.60(1H, dd), 3.10(1H, dd), 3.80(3H, s), 3.83(1H, dd), 5.03(1H, d), 5.34(1H, d), 6.73~7.27(6H, m) | 441, 439, 280 |
| 55 | 6-Cl | $-COOCH_3$ | | 2.64(1H, dd), 3.10(1H, dd), 3.73(3H, s), 3.99(1H, dd), 5.12(2H, s), 6.97~7.38 (6H, m) | 431, 429, 270 |
| 56 | 6-F | $-COOCH_3$ | | 2.65(1H, dd), 3.11(1H, dd), 3.74(3H, s), 3.99(1H, dd), 5.13(2H, s), 6.69~7.39 (6H, m) | 415, 413, 254 |
| 57 | $6-CH_3$ | −COOEt | | 1.25(3H, t), 2.25(3H, s), 2.62(1H, dd), 3.07(1H, dd), 3.97(1H, dd), 4.18(2H, q), 5.09(1H, d), 5.17(1H, d), 6.78~7.35 (6H, m) | 425, 423, 264 |
| 58 | $6-OCH_3$ | −COOEt | | 1.27(3H, t), 2.62(1H, dd), 3.07(1H, dd), 3.72(3H, s), 3.98(1H, dd), 4.20(2H, q), 5.10(1H, d), 5.17(1H, d), 6.52~7.38 (6H, m) | 441, 439, 280 |
| 59 | $7-CH_3$ | $-COOCH_3$ | | 2.27(3H, s), 2.63(1H, dd), 3.10(1H, dd), 3.74(3H, s), 4.02(1H, dd), 5.15(2H, s), 6.82~7.41(6H, m) | 411, 409, 250 |
| 60 | $7-OCH_3$ | −COOEt | | 1.28(3H, t), 2.63(1H, dd), 3.09(1H, dd), 3.76(3H, s), 4.01(1H, dd), 4.21(2H, q), 5.12(2H, s), 6.83~7.37(6H, m) | 441, 439, 280 |
| 61 | 8-Cl | −COOEt | | 1.29(3H, t), 2.68(1H, dd), 3.12(1H, dd), 4.01(1H, dd), 4.21(2H, q), 5.08(1H, d), 5.21(1H, d), 6.87~7.39(6H, m) | 445, 443, 284 |

EXAMPLE 62

Methyl (Z)-2-(4-benzyl-3,4-dihydro-3-oxo-2H-1,4-benzothiazin-2-ylidene)acetate

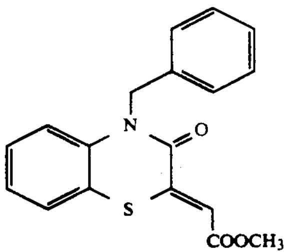

Methyl (Z)-2-(3,4-dihydro-3-oxo-2H-1,4-benzothiazin-2-ylidene)acetate (940 mg) was dissolved in 8 ml of N,N-dimethylformamide, and the solution was added dropwise to a suspension of sodium hydride (60% in oil, 192 mg) in 2 ml of N,N-dimethylformamide. The mixture was stirred for 30 minutes. To the mixture was added dropwise a solution of 752 mg of benzyl bromide in 2 ml of N,N-dimethylformamide. The stirring was continued for an hour under ice-cooling, the reaction mixture was poured onto ice water, and extracted with ethyl acetate. Then, the ethyl acetate layer was washed with water. After the drying of the organic layer over anhydrous magnesium sulfate, the solvent was distilled off. The resulting oily matter was solidified in isopropyl etherhexane to give 1.04 g of methyl (Z)-2-(4-benzyl-3,4-dihydro-3-oxo-2H-1,4-benzothiazin-2-ylidene)acetate as yellow powder. The structural formula and physical data of this compound are shown in Table 14.

EXAMPLES 63 AND 64

In a manner substantially similar to Example 62, the compounds shown in Table 14 were obtained.

Together with the compound obtained in Example 62, the structural formulae and physical data of these compounds are shown in Table 14.

TABLE 14

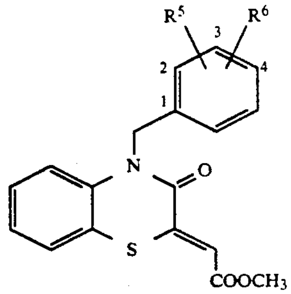

| Ex. | $R^5$ | $R^6$ | melting Point (°C.) | NMR ($CDCl_3$) δ | MS (EI) m/z |
|---|---|---|---|---|---|
| 62 | H | H | 140~142 | 3.83(3H, s), 5.42(2H, s), 7.01~7.36(10H, m) | 325, 282, 236 |
| 63 | 3-Cl | 4-Cl | 168 (dec.) | 3.84(3H, s), 5.35(2H, s), 6.91~7.44(8H, m) | 395, 393, 235 |
| 64 | 2-F | 4-Br | 183 (dec.) | 3.84(3H, s), 5.39(2H, s), 6.90~7.37(8H, m) | 423, 421, 187 |

EXAMPLE 65

Ethyl 2-[4-(benzothiazol-2-yl)methyl-3,4-dihydro-3-oxo-2H-1,4-benzothiazin-2-yl]acetate

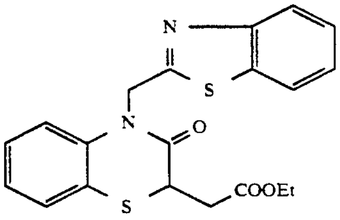

A mixture of 208 mg of ethyl 2-(4-cyanomethyl-3,4-dihydro-3-oxo-2H-1,4-benzothiazin-2-yl)acetate and 116 mg of 2-aminothiophenol hydrochloride was heated at 180° C. for 15 minutes to fuse them. After the mixture had been cooled, water was added, and then extracted with ethyl acetate. After the drying of the organic layer over anhydrous magnesium sulfate, the solvent was distilled off. The resulting oily matter was purified by silica gel chromatography to give 196 mg of the title compound. The structural formula and physical data of this compound are shown in Table 15.

EXAMPLES 66 THROUGH 95

In a manner substantially similar to Example 65, the compounds shown in Tables 15 through 18 were obtained.

Together with the compound obtained in Example 65, the structural formulae and physical data of these compounds are shown in Tables 15 through 18.

EXAMPLE 96

Ethyl 2-[4-(5,7-difluorobenzothiazol-2-yl)methyl-3,4-dihydro-3-oxo-2H-1,4-benzothiazin-2-yl]acetate

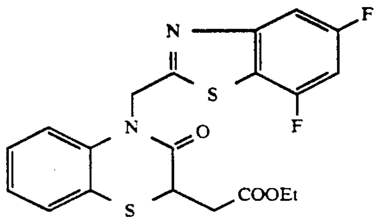

Ethyl 2-(4-cyanomethyl-3,4-dihydro-3-oxo-2H-1,4-benzothiazin-2-yl)acetate (580 mg) and 474 mg of 2-amino-4,6-difluorothiophenol hydrochloride were added to 4 ml of anhydrous ethanol, the mixture was heated to reflux under argon atmosphere. After 15 hours, the solvent was distilled off. Water was added to the mixture, and extracted with ethyl acetate. After the drying of the organic layer over anhydrous magnesium sulfate, the solvent was distilled off. The resulting oily matter was subjected to alumina column chromatography. Elution with hexane-ehtyl acetate gave 660 mg of the title compound. The structural formula and physical data of this compound are shown in Table 19.

EXAMPLES 97 THROUGH 128

In a manner substantially similar to Example 96, the compounds shown in Tables 19 through 22 were obtained.

Together with the compound obtained in Example 96, the structural formulae and physical data of these compounds are shown in Tables 19 through 22.

TABLE 15

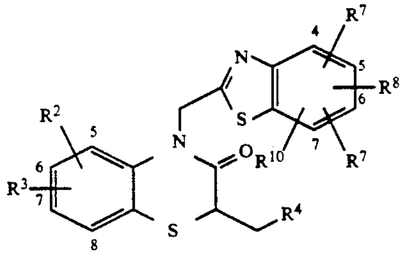

| Ex. | $R^7$, $R^8$, $R^9$, $R^{10}$ | $R^2$, $R^3$ | $R^4$ | NMR ($CDCl_3$) δ | MS (EI) m/z |
|---|---|---|---|---|---|
| 65 | H | H | —COOEt | 1.28(3H, t), 2.64(1H, dd) 3.13(1H, dd), 4.06(1H, dd), 4.21(2H, q), 5.50(1H, d), 5.62(1H, d), 7.00~8.03(8H, m) | 398, 250, |
| 66 | 5-Br | H | —COOEt | 1.28(3H, t), 2.63(1H, dd), 3.11(1H, dd), 4.05(1H, dd), | 478, 476, |

TABLE 15-continued

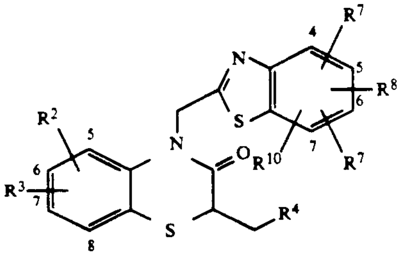

| Ex. | $R^7$, $R^8$, $R^9$, $R^{10}$ | $R^2$, $R^3$ | $R^4$ | NMR ($CDCl_3$) δ | MS (EI) m/z |
|---|---|---|---|---|---|
| | | | | 4.21(2H, q), 5.49(1H, d), 5.61(1H, d), 7.03~8.17(7H, m) | 250 |
| 67 | 6-Cl | H | —COOEt | 1.28(3H, t), 2.64(1H, dd), 3.12(1H, dd), 4.05(1H, dd), 4.21(2H, q), 5.47(1H, d), 5.60(1H, d), 7.02~7.93(7H, m) | 434, 432, 250 |
| 68 | 7-Cl | H | —COOEt | 1.29(3H, t), 2.65(1H, dd), 3.14(1H, dd), 4.07(1H, dd), 4.22(2H, q), 5.49(1H, d), 5.61(1H, d), 7.03~7.93(7H, m) | 434, 432, 250 |
| 69 | 4,5-Cl | H | —COOEt | 1.28(3H, t), 2.64(1H, dd), 3.11(1H, dd), 4.05(1H, dd), 4.21(2H, q), 5.56(1H, d), 5.66(1H, d), 7.02~7.64(6H, m) | 468, 466, 250 |
| 70 | 6,7-F | H | —COOEt | 1.29(3H, t), 2.65(1H, dd) 3.12(1H, dd), 4.06(1H, dd), 4.22(2H, q), 5.48(1H, d), 5.59(1H, d), 7.03~7.76(6H, m) | 434, 250 |
| 71 | 4,5-Cl | 6-Me | —COOEt | 1.28(3H, t), 2.31(3H, s), 2.63(1H, dd), 3.09(1H, dd), 4.01(1H, dd), 4.21(2H, q), 5.56(1H, d), 5.65(1H, d), 6.87~7.27(3H, m), 7.47(1H, d), 7.65(1H, d) | 452, 286 |

TABLE 16

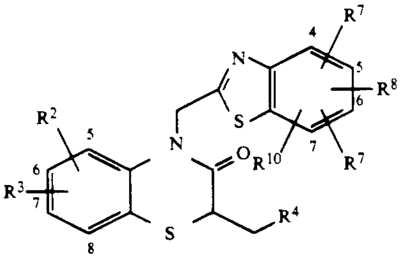

| Ex. | $R^7$, $R^8$, $R^9$, $R^{10}$ | $R^2$, $R^3$ | $R^4$ | NMR ($CDCl_3$) δ | MS (EI) m/z |
|---|---|---|---|---|---|
| 72 | 4,7-Cl | H | —COOEt | 1.28(3H, t), 2.65(1H, dd), 3.13(1H, dd), 4.07(1H, dd), 4.21(2H, q), 5.56(1H, d), 5.65(1H, d), 7.02~7.45(6H, m) | 468, 466, 250 |
| 73 | 4,7-F | H | —COOEt | 1.18(3H, t), 2.55(1H, dd), 3.02(1H, dd), 3.96(1H, dd), 4.11(2H, q), 5.44(1H, d), 5.54(1H, d), 6.89~7.29(6H, m) | 434, 250 |
| 74 | 5,6-F | H | —COOEt | 1.28(3H, t), 2.64(1H, dd), 3.11(1H, dd), 4.04(1H, dd), 4.21(2H, q), 5.45(1H, d), 5.59(1H, d), 7.01~7.81(6H, m) | 434, 250 |
| 75 | 6,7-Cl | H | —COOEt | 1.28(3H, t), 2.65(1H, dd), 3.13(1H, dd), 4.06(1H, dd), 4.21(2H, q), 5.46(1H, d), 5.58(1H, d), 7.02~7.39(4H, m) 7.52(1H, d), 7.81(1H, d) | 468, 466, 250 |
| 76 | 4,5,6-Cl | H | —COOEt | 1.29(3H, t), 2.64(1H, dd), 3.11(1H, dd), 4.05(1H, dd), 4.22(2H, q), 5.55(1H, d), 5.64(1H, d), 7.04~7.41(4H, m), 7.85 (1H, s) | 504, 502, 500, 250 |
| 77 | 4,5-Cl | 6-F | —COOEt | 1.28(3H, t), 2.63(1H, dd), 3.10(1H, dd), 4.02(1H, dd), 4.21(2H, q), 5.52(1H, d), 5.61(1H, d), 6.78~7.37(3H, m), 7.48 (1H, d), 7.65(1H, d) | 486, 484, 268 |
| 78 | 5-Br-7-F | H | —COOEt | 1.28(3H, t), 2.64(1H, dd), 3.12(1H, dd), 4.05(1H, dd), 4.21(2H, q), 5.49(1H, d), | 496, 494, |

TABLE 16-continued

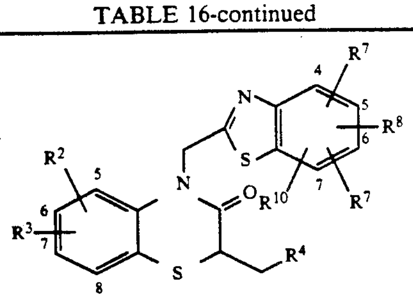

| Ex. | $R^7$, $R^8$, $R^9$, $R^{10}$ | $R^2$, $R^3$ | $R^4$ | NMR ($CDCl_3$) δ | MS (EI) m/z |
|---|---|---|---|---|---|
| | | | | 5.60(1H, d), 7.02~7.39(3H, m), 7.96 (1H, d) | 250 |
| 79 | 5,6,7-Cl | H | —COOEt | 1.28(3H, t), 2.64(1H, dd), 3.12(1H, dd), 4.05(1H, dd), 4.21(2H, q), 5.45(1H, d), 5.57(1H, d), 7.04~7.40(4H, m), 8.03 (1H, s) | 504, 502, 500, 250 |
| 80 | 4,5,7-F | 6-Me | —COOEt | 1.28(3H, t), 2.32(3H, s), 2.63(1H, dd), 3.09(1H, dd), 4.02(1H, dd), 4.21(2H, q), 5.54(1H, d), 5.61(1H, d), 6.88~7.29(4H, m) | 466, 264 |

TABLE 17

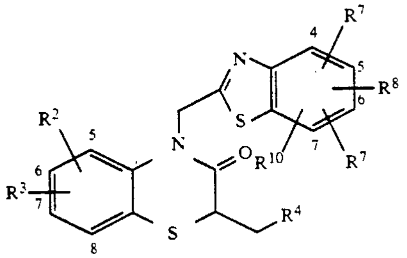

| Ex. | $R^7$, $R^8$, $R^9$, $R^{10}$ | $R^2$, $R^3$ | $R^4$ | NMR ($CDCl_3$) δ | MS (EI) m/z |
|---|---|---|---|---|---|
| 81 | 4,5,7-Cl | H | —COOEt | 1.29(3H, t), 2.62(1H, dd), 3.13(1H, dd), 4.06(1H, dd), 4.22(2H, q), 5.55(1H, d), 5.64(1H, d), 7.03~7.41(4H, m), 7.46(1H, s) | 504, 502, 500, 250 |
| 82 | 4,5-F | 8-F | —COOEt | 1.29(3H, t), 2.67(1H, dd), 3.13(1H, dd), 4.04(1H, dd), 4.22(2H, q), 5.56(1H, d), 5.66(1H, d), 6.86~7.24(3H, m), 7.47 (1H, d), 7.65(1H, d) | 486, 484, 268 |
| 83 | 4,5,7-F | 6-F | —COOEt | 1.29(3H, t), 2.63(1H, dd), 3.10(1H, dd), 4.02(1H, dd), 4.22(2H, q), 5.49(1H, d), 5.59(1H, d), 6.78~7.39(4H, m) | 470, 268 |
| 84 | 5,7-F | 6-F | —COOEt | 1.28(3H, t), 2.63(1H, dd), 3.11(1H, dd), 4.03(1H, dd), 4.21(2H, q), 5.44(1H, d), 5.57(1H, d), 6.77~7.57(5H, m) | 452, 268 |
| 85 | 4,5,7-F | 6-OMe | —COOEt | 1,28(3H, t), 2.61(1H, dd), 3.07(1H, dd), 3.80(3H, s), 4.00(1H, dd), 4.21(2H, q), 5.51(1H, d), 5.60(1H, d), 6.62~7.30(4H, m) | 482, 280 |
| 86 | 5,7-F | 6-$CF_3$ | —COOEt | 1.28(3H, t), 2.64(1H, dd), 3.13(1H, dd), 4.06(1H, dd), 4.21(2H, q), 5.50(1H, d), 5.62(1H, d), 6.89~7.58(5H, m) | 502, 318 |
| 87 | 5,7-F | 6-OMe | —COOEt | 1.27(3H, t), 2.63(1H, dd), 3.09(1H, dd), 3.76(3H, s), 4.02(1H, dd), 4.20(2H, q), 5.48(1H, d), 5.58(1H, d), 6.59~7.52(5H, m) | 464, 280 |
| 88 | 4,5-Cl | 6-OMe | —COOEt | 1.28(3H, t), 2.60(1H, dd), 3.07(1H, dd), 3.82(3H, s), 3.98(1H, dd), 4.20(2H, q), 5.52(1H, d), 5.63(1H, d), 6.63(1H, dd), 7.15(1H, d), 7.26(1H, d), 7.48(1H, d) | 498, 496, 280 |
| 89 | 6,7-F | 6-F | —COOEt | 1.28(3H, t), 2.62(1H, dd), 3.10(1H, dd), 4.02(1H, dd), 4.21(2H, q), 5.43(1H, d) 5.55(1H, d), 6.77~7.80(5H, m) | 452, 268 |

TABLE 18

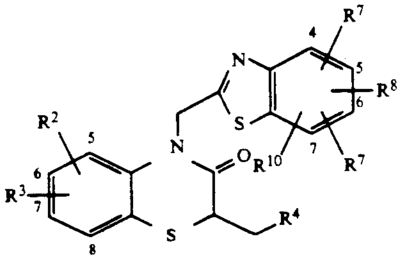

| Ex. | $R^7$, $R^8$, $R^9$, $R^{10}$ | $R^2$, $R^3$ | $R^4$ | NMR ($CDCl_3$) δ | MS (EI) m/z |
|---|---|---|---|---|---|
| 90 | 4,5,7-F | 8-F | —COOEt | 1.29(3H, t), 2.67(1H, dd), 3.12(1H, dd), 4.03(1H, dd), 4.23(2H, q), 5.52(1H, d), 5.63(1H, d), 6.87~7.26(4H, m), | 470, 268 |
| 91 | 4,5-F | 6-F | —COOEt | 1.29(3H, t), 2.63(1H, dd), 3.10(1H, dd), 4.02(1H, dd), 4.21(2H, q), 5.48(1H, d), 5.60(1H, d), 6.78~7.50(5H, m) | 452, 268 |
| 92 | 4,5-F | 6-Me | —COOEt | 1.28(3H, t), 2.30(3H, s), 2.64(1H, dd), 3.10(1H, dd), 4.03(1H, dd), 4.21(2H, q), 5.53(1H, d), 5.63(1H, d), 6.84~7.50(5H, m) | 448, 264 |
| 93 | 4,5-F | 6-OMe | —COOEt | 1.28(3H, t), 2.61(1H, dd), 3.07(1H, dd), 3.79(3H, s), 3.99(1H, dd), 4.21(2H, q), 5.50(1H, d), 5.62(1H, d), 6.61~7.53(5H, m) | 464, 280 |
| 94 | 6,7-F | 6-OMe | —COOEt | 1,28(3H, t), 2.61(1H, dd), 3.08(1H, dd), 3.78(3H, s), 4.01(1H, dd), 4.21(2H, q), 5.46(1H, d), 5.56(1H, d), 6.61~7.76(5H, m) | 464, 280 |
| 95 | 5,7-F | 8-F | —COOEt | 1.28(3H, t), 2.66(1H, dd), 3.13(1H, dd), 4.04(1H, dd), 4.22(2H, q), 5.48(1H, d), 5.61(1H, d), 6.87~7.55(5H, m) | 452, 268 |

TABLE 19

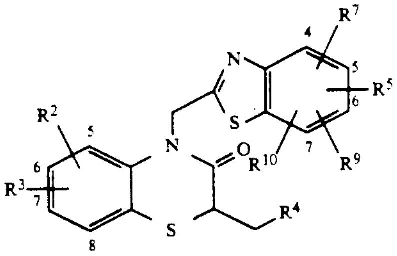

| Ex. | $R^7$, $R^8$, $R^9$, $R^{10}$ | $R^2$, $R^3$ | $R^4$ | NMR ($CDCl_3$) δ | MS (EI) m/z |
|---|---|---|---|---|---|
| 96 | 5,7-F | H | —COOEt | 1.28(3H, t), 2.64(1H, dd), 3.12(1H, dd), 4.06(1H, dd), 4.22(2H, q), 5.50(1H, d), 5.59(1H, d), 6.88~7.56(6H, m) | 434, 250 |
| 97 | 4-Cl | H | —COOEt | 1.29(3H, t), 2.65(1H, dd), 3.13(1H, dd), 4.06(1H, dd), 4.22(2H, q), 5.60(1H, d), 5.60(1H, d), 7.02~7.73(7H, m) | 434, 432, 250 |
| 98 | 4-F | H | —COOEt | 1.29(3H, t), 2.64(1H, dd), 3.12(1H, dd), 4.05(1H, dd), 4.22(2H, q), 5.56(1H, d), 5.64(1H, d), 7.02~7.61(7H, m) | 416, 250 |
| 99 | 4-F | 6-Me | —COOEt | 1.28(3H, t), 2.30(3H, s), 2.63(1H, dd), 3.10(1H, dd), 4.03(1H, dd), 4.21(2H, q), 5.56(1H, d), 5.62(1H, d), 6.86~7.61(6H, m) | 434, 432, 250 |
| 100 | 5-F | 5-F | —COOEt | 1.29(3H, t), 2.66(1H, dd), 3.17(1H, dd), 3.99(1H, dd), 4.21(2H, q), 5.51(1H, d), 5.65(1H, d), 7.00~7.23(5H, m), 7.61~7.74(2H, m) | 434, 268 |
| 101 | 5,7-Cl | H | —COOEt | 1.28(3H, t), 2.64(1H, dd), 3.13(1H, dd), 4.06(1H, dd), 4.22(2H, q), 5.47(1H, d), 5.58(1H, d), 7.03~7.41(5H, m), 7.91(1H, d) | 468, 466, 250 |
| 102 | 5,7-F | 6-Me | —COOEt | 1.28(3H, t), 2.31(3H, s), 2.63(1H, dd), 3.09(1H, dd), 4.02(1H, dd), 4.21(2H, q), 5.50(1H, d), 5.56(1H, d), 6.87~7.56(5H, m) | 448, 264 |
| 103 | 5,7-Me | H | —COOEt | 1.20(3H, t), 2.38(6H, s), 2.55(1H, dd), 3.06(1H, dd), 3.98(1H, dd), 4.13(2H, q), 5.41(1H, d), 5.52(1H, d), 6.92~7.30(5H, m), 7.57(1H, s) | 426 |

TABLE 19-continued

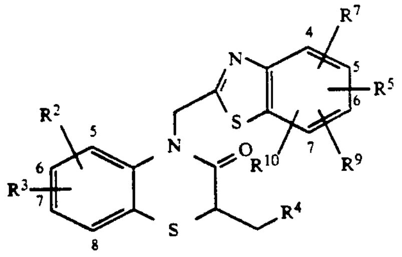

| Ex. | $R^7$, $R^8$, $R^9$, $R^{10}$ | $R^2$, $R^3$ | $R^4$ | NMR ($CDCl_3$) δ | MS (EI) m/z |
|---|---|---|---|---|---|
| 104 | 6-F | H | —COOEt | 1.28(3H, t), 2.63(1H, dd), 3.11(1H, dd), 4.05(1H, dd), 4.22(2H, q), 5.48(1H, d), 5.59(1H, d), 7.02~7.52(6H, m), 7.93~7.98 (1H, m) | 416, 250 |
| 105 | 5,7-F | 7-F | —COOEt | 1.29(3H, t), 2.63(1H, dd), 3.11(1H, dd), 4.05(1H, dd), 4.22(2H, q), 5.46(1H, d), 5.55(1H, d), 6.91~7.56(5H, m) | 452, 268 |

TABLE 20

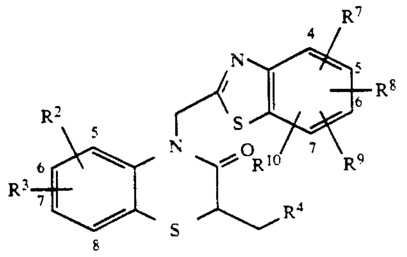

| Ex. | $R^7$, $R^8$, $R^9$, $R^{10}$ | $R^2$, $R^3$ | $R^4$ | NMR ($CDCl_3$) δ | MS (EI) m/z |
|---|---|---|---|---|---|
| 106 | 4,5,7-F | H | —COOEt | 1.29(3H, t), 2.65(1H, dd), 3.12(1H, dd), 4.06(1H, dd), 4.22(2H, q), 5.55(1H, d), 5.62(1H, d), 6.99~7.41(5H, m) | 452, 250 |
| 107 | 6,7-F | 7-F | —COOEt | 1.29(3H, t), 2.64(1H, dd), 3.12(1H, dd), 4.05(1H, t), 4.22(2H, q), 5.45(1H, d), 5.54(1H, d), 6.91~7.77(4H, m) | 452, 268 |
| 108 | 4,5-Cl | 7-F | —COOEt | 1.29(3H, t), 2.64(1H, dd), 3.11(1H, dd), 4.04(1H, t), 4.22(2H, q), 5.55(1H, d), 5.61(1H, d), 6.91~7.67(5H, m) | 486, 484, 268 |
| 109 | 4,5,6,7-F | H | —COOEt | 1.20(3H, t), 2.55(1H, dd), 3.01(1H, dd), 3.95(1H, t), 4.12(2H, q), 5.42(1H, d), 5.51(1H, d), 6.95~7.31(4H, m) | 470, 250 |
| 110 | 5,7-F | 7-$OCF_3$ | —COOEt | 1.29(3H, t), 2.65(1H, dd), 3.13(1H, dd), 4.07(1H, dd), 4.22(2H, q), 5.45(1H, d), 5.60(1H, d), 6.91~7.57(5H, m), | 518, 334 |
| 111 | 4,5,7-F | 7-F | —COOEt | 1.29(3H, t), 2.63(1H, dd), 3.11(1H, dd), 4.05(1H, t), 4.22(2H, q), 5.41(1H, d), 5.58(1H, d), 6.93~7.38(4H, m) | 470 |
| 112 | 4,5-F | H | —COOEt | 1.29(3H, t), 2.64(1H, dd), 3.11(1H, dd), 4.05(1H, dd), 4.22(2H, q), 5.54(1H, d), 5.63(1H, d), 7.03~7.53(6H, m) | 434, 250 |
| 113 | 4,5,7-F | 7-OMe | —COOEt | 1.29(3H, t), 2.64(1H, dd), 3.11(1H, dd), 3.78(3H, s), 4.05(1H, dd), 4.22(2H, q), 5.55(2H, s), 6.76~7.26(4H, m) | 482, 280 |
| 114 | 4,5-F | 7-F | —COOEt | 1.29(3H, t), 2.63(1H, dd), 3.11(1H, dd), 4.04(1H, dd), 4.22(2H, q), 5.50(1H, d), 5.60(1H, d), 6.92~7.54(5H, m) | 452, 268 |

TABLE 21

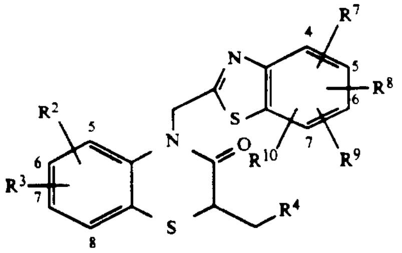

| Ex. | $R^7$, $R^8$, $R^9$, $R^{10}$ | $R^2$, $R^3$ | $R^4$ | NMR ($CDCl_3$) δ | MS (EI) m/z |
|---|---|---|---|---|---|
| 115 | 5,7-F | 7-OMe | —COOEt | 1.29(3H, t), 2.63(1H, dd), 3.11(1H, dd), 3.77(3H, s), 4.05(1H, dd), 4.22(2H, q), 5.48(1H, d), 5.53(1H, d), 6.75~7.56(5H, m) | 464, 280 |
| 116 | 5,7-F | 7-Me | —COOEt | 1.28(3H, t), 2.28(3H, s), 2.63(1H, dd), 3.11(1H, dd), 4.04(1H, dd), 4.21(2H, q), 5.51(1H, d), 5.55(1H, d), 6.87~7.55(5H, m) | 448, 264 |
| 117 | 4,5,7-F | 7-Me | —COOEt | 1.29(3H, t), 2.29(3H, s), 2.63(1H, dd), 3.10(1H, dd), 4.04(1H, dd), 4.22(2H, q), 5.57(2H, s), 7.01~7.27(4H, m) | 466, 264 |
| 118 | 4,5-Cl | 7-Me | —COOEt | 1.29(3H, t), 2.28(3H, s), 2.64(1H, dd), 3.10(1H, dd), 4.04(1H, dd), 4.21(2H, q), 5.58(1H, d), 5.62(1H, d), 7.00~7.65(5H, m) | 482, 480, 264 |
| 119 | 4,5-Cl | 7-OMe | —COOEt | 1.29(3H, t), 2.64(1H, dd), 3.11(1H, dd), 3.77(3H, s), 4.05(1H, dd), 4.21(2H, q), 5.55(1H, d), 5.59(1H, d), 6.74~7.66(5H, m) | 498, 496, 280 |
| 120 | 4,5-F | 7-Me | —COOEt | 1.29(3H, t), 2.28(3H, s), 2.63(1H, dd), 3.10(1H, dd), 4.03(1H, dd), 4.21(2H, q), 5.53(1H, d), 5.59(1H, d), 7.01~7.52(5H, m) | 448, 264 |
| 121 | 4,5-F | 7-OMe | —COOEt | 1.29(3H, t), 2.63(1H, dd), 3.11(1H, dd), 3.77(3H, s), 4.04(1H, dd), 4.22(2H, q), 5.52(1H, d), 5.58(1H, d), 6.76~7.53(5H, m) | 464, 280 |
| 122 | 6,7-F | 7-Me | —COOEt | 1.29(3H, t), 2.28(3H, s), 2.63(1H, dd), 3.11(1H, dd), 4.04(1H, dd), 4.21(2H, q), 5.49(1H, d), 5.54(1H, d), 7.01~7.76(5H, m) | 448, 264 |
| 123 | 6,7-F | 7-OMe | —COOEt | 1.29(3H, t), 2.63(1H, dd), 3.11(1H, dd), 3.77(3H, s), 4.05(1H, dd), 4.21(2H, q), 5.47(1H, d), 5.52(1H, d), 6.75~7.77(5H, m) | 464, 280 |

TABLE 22

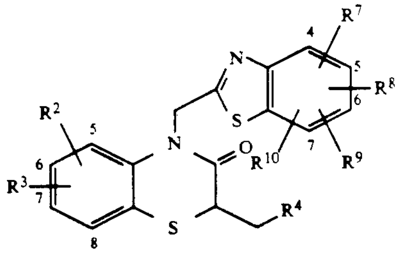

| Ex. | $R^7$, $R^8$, $R^9$, $R^{10}$ | $R^2$, $R^3$ | $R^4$ | NMR ($CDCl_3$) δ | MS (EI) m/z |
|---|---|---|---|---|---|
| 124 | 4,5-F | 7-$CF_3$ | —COOEt | 1.29(3H, t), 2.65(1H, dd), 3.12(1H, dd), 4.06(1H, dd), 4.22(2H, q), 5.54(1H, d), 5.64(1H, d), 7.24~7.66(5H, m) | 502, 318 |
| 125 | 4,5,7-F | 7-Cl | —COOEt | 1.29(3H, t), 2.64(1H, dd), 3.10(1H, dd), 4.04(1H, dd), 4.22(2H, q), 5.51(1H, d), 5.57(1H, d), 7.01~7.39(4H, m) | 488, 486, 284, 282 |
| 126 | 4,5,7-F | 7-$CF_3$ | —COOEt | 1.29(3H, t), 2.65(1H, dd), 3.12(1H, dd), 4.06(1H, dd), 4.22(2H, q), 5.54(1H, d), 5.64(1H, d), 6.92~7.66(4H, m) | 520, 318 |
| 127 | 4,5-F | 7-Cl | —COOEt | 1.29(3H, t), 2.63(1H, dd), 3.10(1H, dd), 4.03(1H, dd), 4.22(2H, q), 5.51(1H, d), 5.59(1H, d), 7.18~7.54(5H, m) | 470, 468, 284 |
| 128 | 4,5,7-F | 7-Br | —COOEt | 1.29(3H, t), 2.63(1H, dd), 3.10(1H, dd), 4.03(1H, dd), 4.22(2H, q), | 532, 530, |

TABLE 22-continued

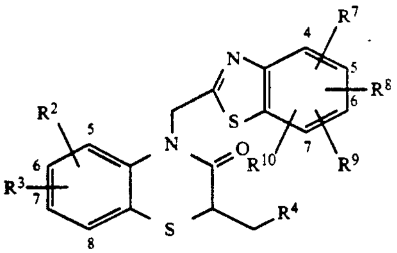

| Ex. | $R^7$, $R^8$, $R^9$, $R^{10}$ | $R^2$, $R^3$ | $R^4$ | NMR ($CDCl_3$) δ | MS (EI) m/z |
|---|---|---|---|---|---|
| | | | | 5.52(1H, d), 5.57(1H, d), 7.01~7.54(4H, m) | 330, 328 |

EXAMPLE 129

Ethyl 2-[4-(5-fluorobenzothiazol-2-yl)methyl-3,4-dihydro-3-thioxo-2H-1,4-benzothiazin-2-yl]acetate

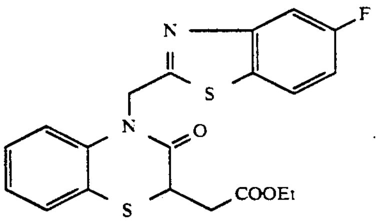

To 10 ml of toluene were added 720 mg of the compound of Example 1 and 770 mg of phosphorus pentasulfide. The mixture was heated to reflux for 4 hours. After the mixture has been cooled, the insoluble substance was filtered off and the solvent was distilled off. The residue was purified by silica gel chromatography to give 535 mg of the title compound. The structural formula and physical data of this compound are shown in Table 23.

TABLE 23

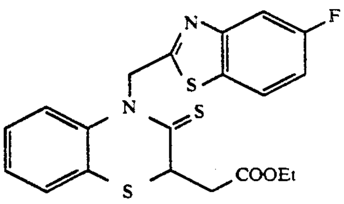

| Ex. | NMR ($CDCl_3$) δ | ME (EI) m/z |
|---|---|---|
| 129 | 1.26(3H, t), 2.61(1H, dd), 3.06(1H, dd), 4.18(2H, q), 4.61(1H, dd), 5.92(1H, d), 6.46(1H, d),. 7.09~7.79(7H, m) | 432 |

EXAMPLE 130

Ethyl-2-[4-(4-bromo-2-fluorophenylmethyl)-3,4-dihydro-3-thioxo-2H-1,4-benzothiazin-2-yl]acetate

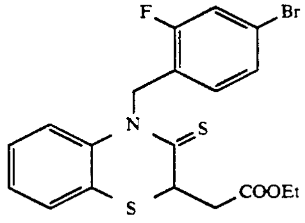

To 4 ml of toluene was added 440 mg of the compound of Example 20 and 310 mg of phosphorus pentasulfide. After the mixture was heated to reflux for 6 hours, the solvent was distilled off. Methylene chloride was added to the mixture, and the insoluble substance was filtered off and the solvent was distilled off. Then the residue was purified by silica gel chromatography to give 350 mg of ethyl 2-[4-(4-bromo-2-fluorophenylmethyl)-3,4-dihydro-3-thioxo-2H-1,4-benzothiazin-2-yl]acetate. The structural formula and physical data of this compound are shown in Table 24.

TABLE 24

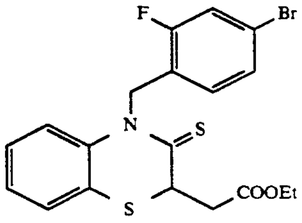

| Ex. | NMR ($CDCl_3$) δ | MS (EI) m/z |
|---|---|---|
| 130 | 1.27(3H, t), 2.65(H, dd), 3.07(1H, dd), 4.18 (2H, q), 4.58(1H, dd), 5.70(1H, d), 5.93(1H, d), 6.87~7.38(7H, m) | 455, 453, 266 |

EXAMPLE 131

2-[4-(5-fluorobenzothiazol-2-yl]methyl-3,4-dihydro-3-oxo-2H-1,4-benzothiazin-2-yl]acetic acid

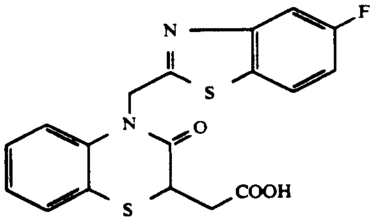

The compound of Example 1 (275 mg) was dissolved in methanol-dioxane (1:2, v/v, 3 ml), and 0.7 ml of 2N sodium hydroxide solution was added dropwise to the solution with stirring at room temperature. The mixture was stirred for further 90 minutes. The solvent was distilled off and the residue was diluted with water, then the aqueous mixture was acidified with 10% hydrochloric acid. The precipitated solid was crystallized from chloroform-hexane to give 196 mg of the title compound. The structural formula and physical data of this compound are shown in Table 25.

EXAMPLES 132 THROUGH 214

In a manner substantially similar to Example 131, the compounds shown in Tables 25 through 35 were obtained.

Together with the compound obtained in Example 131, the structural formulae and physical data of these compounds are shown in Tables 25 through 35.

TABLE 25

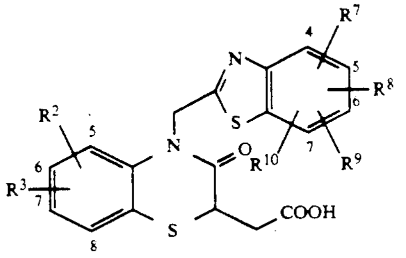

| Ex. | $R^7$, $R^8$, $R^9$, $R^{10}$ | $R^2$, $R^3$ | IR (KBr) $cm^{-1}$ | NMR: δ | MS (EI) m/z |
|---|---|---|---|---|---|
| 131 | 5-F | H | 2600~3450 1744, 1662 | 2.71(1H, dd), 3.18(1H, dd), 4.02(1H, dd), 5.50(1H, dd), 5.64(1H, d), 7.06~7.70(7H, m) [$CDCl_3$] | 388, 222 |
| 132 | 5-F | 6-Me | 2570~3450 1722, 1660 | 2.30(3H, s), 2.71(1H, dd), 3.17(1H, dd), 3.99(1H, dd), 5.49(1H, d), 5.62(1H, d), 6.87~7.78(6H, m) [$CDCl_3$] | 402, 236 |
| 133 | 5-F | 7-OEt | 2570~3480 1740, 1668 | 1.38(3H, t), 2.72(1H, dd), 3.17(1H, dd), 3.98(2H, q), 4.01(1H, dd), 5.46(1H, d), 5.58(1H, d), 6.74~7.77(6H, m) [$CDCl_3$] | 432, 266 |
| 134 | 5-F | 6,8-Me | 2560~3460 1722, 1688 | 2.25(3H, s), 2.32(3H, s), 2.60(1H, dd), 3.09(1H, dd), 3.96(1H, dd), 5.50(1H, d), 5.57(1H, d), 6.79(1H, s), 6.96(1H, s), 7.12~7.78(3H, m) [$CDCl_3$ − $DMSOd_6$] | 416, 250 |
| 135 | 5-F | 6-F | 2550~3460 1734, 1664 | 2.60(1H, dd), 3.10(1H, dd), 4.01(1H, dd), 5.47(1H, d), 5.55(1H, d), 6.75~7.79(6H, m) [$CDCl_3$ − $DMSOd_6$] | 406, 240 |
| 136 | 7-F | H | 2530~3440 1718, 1666 | 2.62(1H, dd), 3.10(1H, dd), 4.04(1H, dd), 5.51(1H, d), 5.61(1H, d), 7.03~7.84(7H, m), [$CDCl_3$ − $DMSOd_6$] | 388, 222 |
| 137 | 5-$CF_3$ | H | 2580~3460 1714, 1652 | 2.72(1H, dd), 3.19(1H, dd), 4.03(1H, dd), 5.52(1H, d), 5.67(1H, d), 7.04~8.28(7H, m) [$CDCl_3$] | 438, 222 |
| 138 | 5-Cl | H | 2550~3470 1726, 1670 | 2.72(1H, dd), 3.18(1H, dd), 4.02(1H, dd), 5.48(1H, d), 5.63(1H, d), 7.04~8.01(7H, m) [$CDCl_3$] | 406, 404, 222 |
| 139 | 5-Cl | 6-Me | 2550~3450 1722, 1660 | 2.30(3H, s), 2.70(1H, dd), 3.16(1H, dd), 3.99(1H, dd), 5.49(1H, d), 5.61(1H, d) 6.87~8.01(6H, m) [$CDCl_3$] | 421, 419, 236 |

TABLE 26

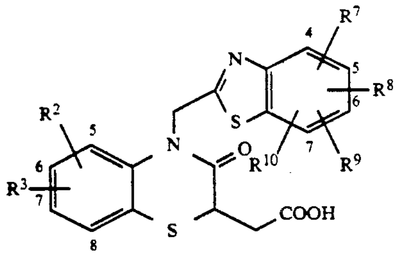

| Ex. | $R^7$, $R^8$, $R^9$, $R^{10}$ | $R^2$, $R^3$ | IR (KBr) $cm^{-1}$ | NMR: δ | MS (EI) m/z |
|---|---|---|---|---|---|
| 140 | 5-Cl | 7-Me | 2550~3460 1726, 1664 | 2.27(3H, s), 2.70(1H, dd), 3.17(1H, dd), 4.01(1H, dd), 5.52(1H, d), 5.60(1H, d), 7.00~7.99(6H, m) [$CDCl_3$] | 420, 418, 236 |
| 141 | 5-Cl | 8-Me | 2550~3450 1722, 1674 | 2.37(3H, s), 2.74(1H, dd), 3.21(1H, dd), 3.96(1H, dd), 5.46(1H, d), 5.60(1H, d), 6.96~8.00(6H, m) [$CDCl_3$] | 420, 418, 236 |
| 142 | 5-Cl | 6-OMe | 2600~3460 1720, 1670 | 2.69(1H, dd), 3.15(1H, dd), 3.77(3H, s), 3.97(1H, dd), 5.47(1H, d), 5.61(1H, d), 6.61~7.99(6H, m) [$CDCl_3$] | 436, 434, 252 |
| 143 | 5-Cl | 7-OMe | 2600~3480 1726, 1660 | 2.61(1H, dd), 3.10(1H, dd), 3.76(3H, s), 4.03(1H, dd), 5.52(1H, s), 6.73~7.99(6H, m) [$CDCl_3$ − $DMSOd_6$] | 436, 434, 252 |
| 144 | 5-Cl | 7-OEt | 2600~3460 1722, 1668 | 1.38(3H, t), 2.72(1H, dd), 3.18(1H, dd), 3.98(2H, q), 4.01(1H, dd), 5.47(1H, d), 5.58(1H, d), 6.74~8.00(6H, m) [$CDCl_3$] | 450, 448, 266 |
| 145 | 5-Cl | 8-Cl | 2560~3440 1724, 1674 | 2.76(1H, dd), 3.20(1H, dd), 3.97(1H, dd), 5.43(1H, d), 5.62(1H, d), 7.05~7.89(6H, m) [$CDCl_3$ − $DMSOd_6$] | 440, 438, 258, 256 |
| 146 | 6-OMe | H | 2550~3450 1722, 1672 | 2.54(1H, dd), 2.90(1H, dd), 3.78(3H, s), 3.91(1H, dd), 5.52(2H, s), 7.05~7.85(7H, m) [$CDCl_3$ − $DMSOd_6$] | 400 |
| 147 | 4,6-F | H | 2540~3450 1724, 1670 | 2.61(1H, dd), 3.10(1H, dd), 4.04(1H, dd), 5.57(2H, s), 6.96~7.39(6H, m) [$CDCl_3$ − $DMSOd_6$] | 406, 222 |
| 148 | 6,7-F | 6-Me | 2540~3460 1732, 1668 | 2.31(3H, s), 2.63(1H, dd), 3.10(1H, dd), 4.01(1H, dd), 5.48(1H, d), 5.57(1H, d) 6.86~7.78(5H, m) [$CDCl_3$ − $DMSOd_6$] | 420, 236 |
| 149 | 5-F | 6,8-F | 2550~3450 1734, 1682 | 2.73(1H, dd), 3.19(1H, dd), 3.98(1H, dd), 5.41(1H, d), 5.61(1H, d) 6.65~7.80(5H, m) [$CDCl_3$] | 424, 258 |

TABLE 27

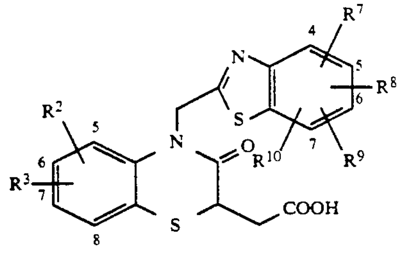

| Ex. | $R^7$, $R^8$, $R^9$, $R^{10}$ | $R^2$, $R^3$ | IR (KBr) $cm^{-1}$ | NMR: δ | MS (EI) m/z |
|---|---|---|---|---|---|
| 150 | H | H | 2580~3450 1718, 1660 | 2.72(1H, dd), 3.20(1H, dd), 4.03(1H, dd), 5.53(1H, d), 5.66(1H, d), 7.02~8.03(8H, m) [$CDCl_3$]. | 370, 222 |
| 151 | 5-Br | H | 2550~3450 1722, 1672 | 2.71(1H, dd), 3.18(1H, dd), 4.02(1H, dd), 5.49(1H, d), 5.63(1H, d), 7.03~8.17(7H, m) [$CDCl_3$] | 450, 448, 222 |
| 152 | 6-Cl | H | 2550~3470 1722, 1674 | 2.60(1H, dd), 3.09(1H, dd), 4.03(1H, dd), 5.50(1H, d), 5.59(1H, d), 7.02~7.94(7H, m) [$CDCl_3$ − $DMSOd_6$] | 406, 404, 222 |
| 153 | 7-Cl | H | 2530~3450 1722, 1688 | 2.62(1H, dd), 3.12(1H, dd), 4.05(1H, dd), 5.49(1H, d), 5.60(1H, d), 7.03~7.94(7H, m) [$CDCl_3$ − $DMSOd_6$] | 406, 404, 222 |
| 154 | 4,5-Cl | H | 2580~3450 1738, 1668 | 2.73(1H, dd), 3.19(1H, dd), 4.02(1H, dd), 5.56(1H, d), 5.68(1H, d), 7.05~7.66(6H, m) [$CDCl_3$] | 440, 438, 222 |

TABLE 27-continued

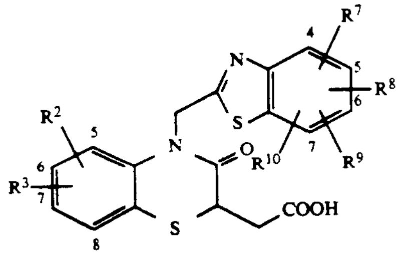

| Ex. | $R^7$, $R^8$, $R^9$, $R^{10}$ | $R^2$, $R^3$ | IR (KBr) $cm^{-1}$ | NMR: δ | MS (EI) m/z |
|---|---|---|---|---|---|
| 155 | 6,7-F | H | 2540~3450 1718, 1662 | 2.62(1H, dd), 3.10(1H, dd), 4.04(1H, dd), 5.48(1H, d), 5.58(1H, d), 7.03~7.78(6H, m) [$CDCl_3$ − $DMSOd_6$] | 406, 222 |
| 156 | 4,5-Cl | 6-Me | 2550~3450 1734, 1682 | 2.30(3H, s), 2.61(1H, dd), 3.08(1H, dd), 4.01(1H, dd), 5.61(2H, s), 6.85(1H, d), 7.17(1H, s), 7.26(1H, d), 7.46(1H, d), 7.65(1H, d) [$CDCl_3$ − $DMSOd_6$] | 454, 452, 236 |
| 157 | 4,7-Cl | H | 2550~3450 1745, 1675 | 2.74(1H, dd), 3.22(1H, dd), 4.04(1H, dd), 5.56(1H, d), 5.67(1H, d), 7.05~7.47(6H, m) [$CDCl_3$] | 440, 438, 231 |
| 158 | 4,7-F | H | 2530~3450 1730, 1670 | 2.73(1H, dd), 3.20(1H, dd), 4.03(1H, dd), 5.55(1H, d), 5.64(1H, d), 6.99~7.42(6H, m) [$CDCl_3$] | 406, 222 |
| 159 | 5,6-F | H | 2600~3450 1750, 1670 | 2.72(1H, dd), 3.18(1H, dd), 4.01(1H, dd), 5.45(1H, d), 5.62(1H, d), 7.05~7.83(6H, m) [$CDCl_3$] | 406, 231 |

TABLE 28

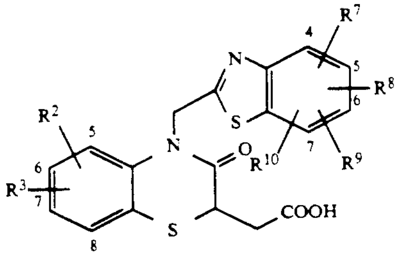

| Ex. | $R^7$, $R^8$, $R^9$, $R^{10}$ | $R^2$, $R^3$ | IR (KBr) $cm^{-1}$ | NMR: δ | MS (EI) m/z |
|---|---|---|---|---|---|
| 160 | 6,7-Cl | H | 2550~3460 1725, 1670 | 2.72(1H, dd), 3.20(1H, dd), 4.03(1H, dd), 5.46(1H, d), 5.62(1H, d), 7.55(1H, d), 7.83(1H, d), 7.05~7.42(4H, m) [$CDCl_3$] | 440, 438, 222 |
| 161 | 4,5,6-Cl | H | 2550~3450 1740, 1670 | 2.73(1H, dd), 3.18(1H, dd), 4.02(1H, dd), 5.54(1H, d), 5.66(1H, d), 7.84(1H, s), 7.05~7.42(4H, m) [$CDCl_3$] | 476, 474, 472, 222 |
| 162 | 4,5-Cl | 6-F | 2550~3450 1730, 1670 | 2.59(1H, dd), 3.06(1H, dd), 4.01(1H, dd), 5.57(2H, s), 6.74~7.35(3H, m), 7.45 (1H, d), 7.63(1H, d) [$CDCl_3$ + $DMSOd_6$] | 458, 456, 240 |
| 163 | 5-Br-7-F | H | 2560~3450 1725, 1670 | 2.72(1H, dd), 3.19(1H, dd), 4.02(1H, dd), 5.48(1H, d), 5.63(1H, d), 7.05~7.42 (5H, m), 7.98(1H, d), [$CDCl_3$] | 468, 466, 222 |
| 164 | 5,6,7-Cl | H | 2570~3460 1720, 1660 | 2.61(1H, dd), 3.10(1H, dd), 4.04(1H, dd), 5.47(1H, d), 5.57(1H, d), 7.04~7.41(4H, m) 8.05(1H, s) [$CDCl_3$ + $DMSOd_6$] | 476, 474, 472, 222 |
| 165 | 4,5,7-F | 6-Me | 2560~3500 1715, 1645 | 2.31(3H, s), 2.68(1H, dd), 3.11(1H, dd), 4.00(1H, dd), 5.53(1H, d), 5.63(1H, d), 6.87~7.26(4H, m) [$CDCl_3$] | 438, 236 |
| 166 | 4,5,7-Cl | H | 2590~3460 1715, 1685 | 2.73(1H, dd), 3.20(1H, dd), 4.03(1H, dd), 5.54(1H, d), 5.66(1H, d), 7.49(1H, s), 7.05~7.43(4H, m) [$CDCl_3$] | 476, 474, 472, 222 |
| 167 | 4,5-Cl | 8-F | 2550~3450 1730, 1675 | 2.65(1H, dd), 3.13(1H, dd), 4.03(1H, dd), 5.62(2H, s), 6.85~7.21(3H, m), 7.47(1H, d), 7.65(1H, m), | 458 456, 240 |

TABLE 28-continued

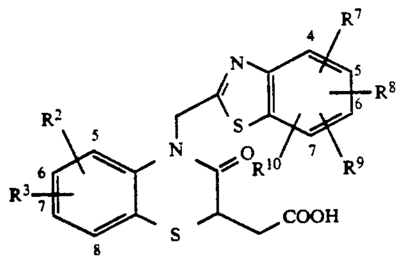

| Ex. | $R^7$, $R^8$, $R^9$, $R^{10}$ | $R^2$, $R^3$ | IR (KBr) $cm^{-1}$ | NMR: δ | MS (EI) m/z |
|---|---|---|---|---|---|
| | | | | [$CDCl_3$ + $DMSOd_6$] | |
| 168 | 4,5,7-F | 6-F | 2550~3470 1740, 1670 | 2.71(1H, dd), 3.17(1H, dd), 3.99(1H, dd), 5.49(1H, d), 5.61(1H, d), 6.79~7.39(4H, m) [$CDCl_3$] | 442, 240, |

TABLE 29

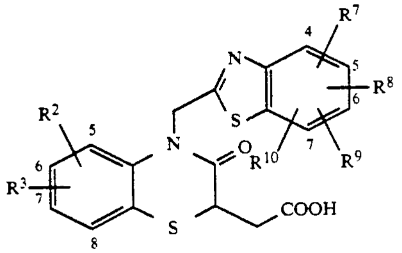

| Ex. | $R^7$, $R^8$, $R^9$, $R^{10}$ | $R^2$, $R^3$ | IR (KBr) $cm^{-1}$ | NMR: δ | MS (EI) m/z |
|---|---|---|---|---|---|
| 169 | 5,7-F | 6-F | 2550~3450 1730, 1675 | 2.71(1H, dd), 3.18(1H, dd), 3.99(1H, dd), 5.43(1H, d), 5.59(1H, d), 6.79~7.58(5H, m) [$CDCl_3$] | 424, 240 |
| 170 | 4,5,7-F | 6-OMe | 2580~3460 1710, 1665 | 2.69(1H, dd), 3.15(1H, dd), 3.80(3H, s), 3.96(1H, dd), 5.50(1H, d), 5.62(1H, d), 6.63~7.30(4H, m) [$CDCl_3$] | 454, 240 |
| 171 | 5,7-F | 6-$CF_3$ | 2550~3450 1700, 1675 | 2.72(1H, dd), 3.20(1H, dd), 4.02(1H, dd), 5.47(1H, d), 5.64(1H, d), 6.89~7.57 (4H, m), 7.76(1H, s) [$CDCl_3$] | 474, 290 |
| 172 | 5,7-F | 6-OMe | 2580~3480 1735, 1665 | 2.70(1H, dd), 3.16(1H, dd), 3.78(3H, s), 3.98(1H, dd), 5.47(1H, d), 5.60(1H, d), 6.62~7.55(5H, m) [$CDCl_3$] | 436, 252 |
| 173 | 5,7-F | H | 2550~3460 1730, 1670 | 2.71(1H, dd), 3.19(1H, dd), 4.03(1H, dd), 5.51(1H, d), 5.62(1H, d), 6.87~7.56(6H, m) [$CDCl_3$] | 406, 222 |
| 174 | 4-Cl | H | 2600~3450 1720, 1660 | 2.72(1H, dd), 3.19(1H, dd), 4.03(1H, dd), 5.60(1H, d), 5.67(1H, d), 7.01~7.72(7H, m) [$CDCl_3$] | 406, 404, 222 |
| 175 | 4-F | H | 2570~3480 1720, 1670 | 2.59(1H, dd), 3.05(1H, dd), 4.01(1H, dd), 5.59(1H, s), 7.03~7.65(7H, m) [$CDCl_3$ – $DMSOd_6$] | 388, 222 |
| 176 | 4-F | 6-Me | 2530~3450 1725, 1670 | 2.30(3H, s), 2.71(1H, dd), 3.17(1H, dd), 4.00(1H, dd), 5.57(1H, d), 5.64(1H, d), 6.85~7.60(6H, m) [$CDCl_3$] | 402, 236 |

TABLE 30

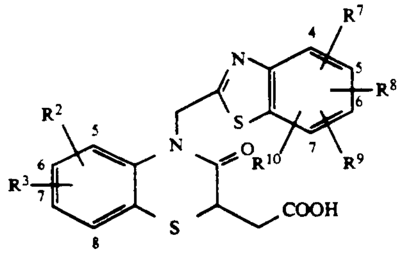

| Ex. | $R^7$, $R^8$, $R^9$, $R^{10}$ | $R^2$, $R^3$ | IR (KBr) $cm^{-1}$ | NMR: δ | MS (EI) m/z |
|---|---|---|---|---|---|
| 177 | 5-F | 5-F | 2540~3540 1720, 1670 | 2.72(1H, dd), 3.22(1H, dd), 3.96(1H, dd), 5.53(1H, d), 5.65(1H, d), 7.01~7.22(4H, m) 7.62~7.74(2H, m) [$CDCl_3$] | 406 |
| 178 | 5,7-Cl | H | 2570~3460 1720, 1675 | 2.61(1H, dd), 3.10(1H, dd), 4.03(1H, dd), 5.49(1H, d), 5.57(1H, d), 7.03~7.41(5H, m) 7.90(1H, d) [$CDCl_3$ − $DMSOd_6$] | 440, 438, 222 |
| 179 | 5,7-F | 6-Me | 2600~3450 1740, 1670 | 2.31(3H, s), 2.70(1H, dd), 3.16(1H, dd), 4.00(1H, dd), 5.51(1H, d), 5.60(1H, d), 6.87~7.56(1H, m) [$CDCl_3$] | 420, 236 |
| 180 | 5,7-Me | H | 2530~3450 1730, 1660 | 2.40(3H, s), 2.42(3H, s), 2.56(1H, dd), 2.93(1H, dd), 3.94(1H, dd), 5.57(1H, d), 5.61(1H, d), 7.08~7.48(5H, m), 7.62(1H, s) [$DMSOd_6$] | 398 |
| 181 | 6-F | H | 2550~3450 1715, 1660 | 2.60(1H, dd), 3.09(1H, dd), 4.03(1H, dd), 5.52(1H, d), 5.56(1H, d), 7.03~7.53(6H, m) 7.92~7.98(1H, m) [$CDCl_3$ − $DMSOd_6$] | 388, 222 |
| 182 | 5,7-F | 7-F | 2600~3440 1720, 1660 | 2.60(1H, dd), 3.09(1H, dd), 4.03(1H, dd), 5.47(1H, d), 5.56(1H, d), 6.91~7.56(5H, m) [$CDCl_3$ − $DMSOd_6$] | 424, 240 |
| 183 | 4,5,7-F | H | 2560~3500 1720, 1660 | 2.71(1H, dd), 3.17(1H, dd), 4.02(1H, dd), 5.54(1H, d), 5.63(1H, d), 6.98~7.41(5H, m) [$CDCl_3$] | 424, 222 |
| 184 | 6,7-F | 7-F | 2550~3420 1720, 1670 | 2.64(1H, dd), 3.11(1H, d), 4.03(1H, t), 5.47(1H, d), 5.55(1H, dd), 6.92~7.78(5H, m) [$CDCl_3$ − $CD_3OD$] | 424, 240 |
| 185 | 4,5-Cl | 7-F | 2550~3480 1710, 1670 | 2.64(1H, dd), 3.11(1H, dd), 4.03(1H, dd), 5.59(2H, s), 6.93~7.67(5H, m) [$CDCl_3$ − $DMSOd_6$] | 458, 456, 240 |

TABLE 31

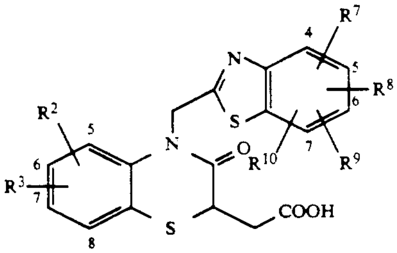

| Ex. | $R^7$, $R^8$, $R^9$, $R^{10}$ | $R^2$, $R^3$ | IR (KBr) $cm^{-1}$ | NMR: δ | MS (EI) m/z |
|---|---|---|---|---|---|
| 186 | 4,5,6,7-F | H | 2570~3550 1720, 1660 | 2.70(1H, dd), 3.16(1H, dd), 4.01(1H, dd), 5.51(1H, d), 5.61(1H, d), 7.04~7.41(4H, m) [$CDCl_3$] | 442, 222 |
| 187 | 5,7-F | 7-$OCF_3$ | 2550~3440 1725, 1675 | 2.72(1H, dd), 3.21(1H, dd), 4.03(1H, dd), 5.43(1H, d), 5.63(1H, d), 6.89~7.56(5H, m) [$CDCl_3$] | 490, 306 |
| 188 | 4,5,7-F | 7-F | 2560~3460 1740, 1670 | 2.71(1H, dd), 3.18(1H, dd), 4.62(1H, dd), 5.50(1H, d), 5.61(1H, d), 6.95~7.41(4H, m) [$CDCl_3$] | 442, 240 |
| 189 | 4,5-F | H | 2550~3450 1730, 1670 | 2.72(1H, dd), 3.18(1H, dd), 4.02(1H, dd), 5.55(1H, d), 5.65(1H, d), 7.04~7.51(6H, m) [$CDCl_3$] | 406, 222 |
| 190 | 4,5,7-F | 7-OMe | 2600~3450 1730, 1670 | 2.71(1H, dd), 3.17(1H, dd), 3.78(3H, s), 4.02(1H, dd), 5.52(1H, d), 5.58(1H, d), | 454, 252 |

TABLE 31-continued

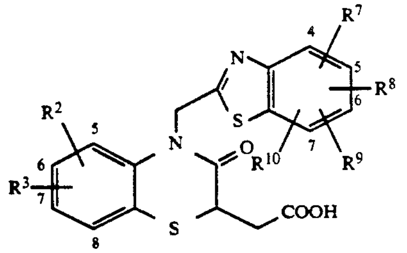

| Ex. | $R^7$, $R^8$, $R^9$, $R^{10}$ | $R^2$, $R^3$ | IR (KBr) $cm^{-1}$ | NMR: δ | MS (EI) m/z |
|---|---|---|---|---|---|
| | | | | 6.77~7.29(4H, m), [$CDCl_3$] | |
| 191 | 4,5-F | 7-F | 2550~3450 1735, 1670 | 2.71(1H, dd), 3.18(1H, dd), 4.01(1H, dd), 5.50(1H, dd), 5.61(1H, d), 6.94~7.54(5H, m) [$CDCl_3$] | 424, 240 |
| 192 | 5,7-F | 7-OMe | 2600~3460 1730, 1660 | 2.61(1H, dd), 3.08(1H, dd), 3.77(3H, s), 4.03(1H, dd), 5.49(1H, d), 5.52(1H, d), 6.75~7.56(5H, m) [$CDCl_3$ − $DMSOd_6$] | 436, 252 |
| 193 | 5,7-F | 7-Me | 2600~3470 1730, 1660 | 2.28(3H, s), 2.71(1H, dd), 3.17(1H, dd), 4.01(1H, dd), 5.51(1H, d), 5.57(1H, dd), 6.87~7.55(5H, m) [$CDCl_3$] | 420, 236 |

TABLE 32

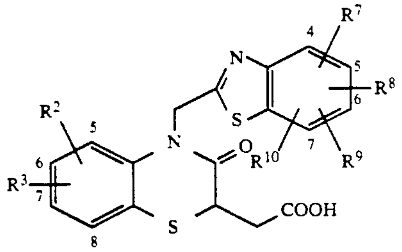

| Ex. | $R^7$, $R^8$, $R^9$, $R^{10}$ | $R^2$, $R^3$ | IR (KBr) $cm^{-1}$ | NMR: δ | MS (EI) m/z |
|---|---|---|---|---|---|
| 194 | 4,5,7-F | 7-Me | 2600~3450 1720, 1670 | 2.28(3H, s), 2.69(1H, dd), 3.15(1H, dd), 4.01(1H, dd), 5.54(1H, d), 5.59(1H, d), 6.96~7.26(4H, m) [$CDCl_3$] | 438, 236 |
| 195 | 4,5-Cl | 7-Me | 2600~3450 1705, 1660 | 2.28(3H, s), 2.71(1H, dd), 3.16(1H, dd), 4.00(1H, dd), 5.58(1H, d), 5.62(1H, d), 7.01~7.64(5H, m) [$CDCl_3$] | 454, 452, 236 |
| 196 | 4,5-Cl | 7-OMe | 2550~3470 1720, 1655 | 2.72(1H, dd), 3.17(1H, dd), 3.77(3H, s), 4.02(1H, dd), 5.56(1H, d), 5.60(1H, d), 6.75~7.65(5H, m) [$CDCl_3$] | 470, 468, 252 |
| 197 | 4,5-F | 7-Me | 2550~3450 1730, 1675 | 2.28(3H, s), 2.70(1H, dd), 3.17(1H, dd), 4.00(1H, dd), 5.55(1H, d), 5,61(1H, d), 7.02~7.52(5H, m) [$CDCl_3$] | 420, 236 |
| 198 | 4,5-F | 7-OMe | 2540~3450 1745, 1660 | 2.61(1H, dd), 3.09(1H, dd), 3.77(3H, s), 4.03(1H, dd), 5.56(2H, s), 6.74~7.54(5H, m) [$CDCl_3$ + $DMSOd_6$] | 436 |
| 199 | 6,7-F | 7-Me | 2530~3450 1730, 1665 | 2.28(3H, s), 2.71(1H, dd), 3.18(1H, dd), 4.01(1H, dd), 5.50(1H, d), 5.57(1H, d), 7.02~7.76(5H, m) [$CDCl_3$] | 420 |
| 200 | 6,7-F | 7-OMe | 2540~3430 1730, 1660 | 2.71(1H, dd), 3.19(1H, dd), 3.77(3H, s), 4.02(1H, dd), 5.48(1H, d), 5.54(1H, d), 6.76~7.76(5H, m) [$CDCl_3$] | 436 |
| 201 | 4,5-F | 7-$CF_3$ | 2600~3450 1750, 1660 | 2.73(1H, dd), 3.19(1H, dd), 4.03(1H, dd), 5.54(1H, d), 5.66(1H, d), 7.21~7.68(5H, m) | 474 |
| 202 | 4,5,7-F | 7-Cl | 2600~3450 1730, 1680 | 2.71(1H, dd), 3.18(1H, dd), 4.01(1H, dd), 5.51(1H, d) | 460, 458, |

TABLE 32-continued

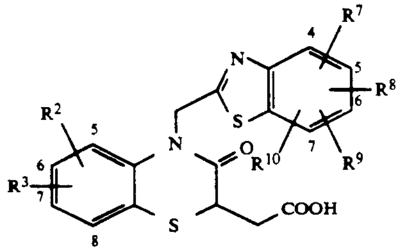

| Ex. | $R^7$, $R^8$, $R^9$, $R^{10}$ | $R^2$, $R^3$ | IR (KBr) $cm^{-1}$ | NMR: δ | MS (EI) m/z |
|---|---|---|---|---|---|
| | | | | 5.60(1H, d), 7.03～7.40(4H, m) [$CDCl_3$] | 256 |

TABLE 33

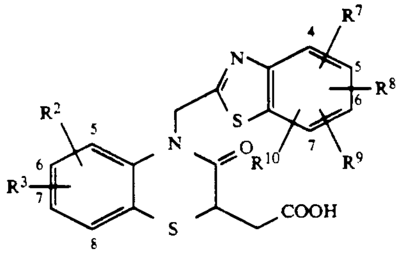

| Ex. | $R^7$, $R^8$, $R^9$, $R^{10}$ | $R^2$, $R^3$ | IR (KBr) $cm^{-1}$ | NMR: δ | MS (EI) m/z |
|---|---|---|---|---|---|
| 203 | 4,5,7-F | 7-$CF_3$ | 2600～3450 1750, 1660 | 2.73(1H, dd), 3.17(1H, dd), 4.04(1H, dd), 5.53(1H, d), 5.65(1H, d), 6.99～7.66(4H, m) [$CDCl_3$] | 492, 290 |
| 204 | 4,5-F | 7-Cl | 2550～3480 1730, 1680 | 2.72(1H, dd), 3.18(1H, dd), 4.01(1H, dd), 5.53(1H, d), 5.63(1H, d), 7.20～7.54(5H, m) [$CDCl_3$] | 442, 440, 256 |
| 205 | 4,5,7-F | 7-Br | 2550～3450 1725, 1680 | 2.71(1H, dd), 3.18(1H, dd), 4.00(1H, dd), 5.51(1H, d), 5.59(1H, d), 6.99～7.54(4H, m) [$CDCl_3$] | 504, 502, 302, 300 |
| 206 | 4,5-Cl | 6-OMe | 2500～3440 1715, 1670 | 2.69(1H, dd), 3.14(1H, dd), 3.82(3H, s), 3.95(1H, t), 5.51(1H, d), 5.65(1H, d), 6.65(1H, dd), 7.18(1H, d), 7.27(1H, d), 7.46(1H, d), 7.65(1H, d) [$CDCl_3$] | 470, 468, 252 |
| 207 | 6,7-F | 6-F | 2550～3450 1720, 1670 | 2.60(1H, dd), 3.08(1H, dd), 4.00(1H, dd), 5.43(1H, d), 5.55(1H, d), 6.77～7.80(5H, m) [$CDCl_3$ + $DMSOd_6$] | 424, 240 |
| 208 | 4,5,7-F | 8-F | 2580～3450 1700, 1655 | 2.76(1H, dd), 3.21(1H, dd), 4.00(1H, dd), 5.52(1H, d), 5.66(1H, d), 6.89～7.26(4H, m) [$CDCl_3$] | 442, 240 |
| 209 | 4,5-F | 6-F | 2550～3450 1735, 1680 | 2.71(1H, dd), 3.18(1H, dd), 3.99(1H, dd), 5.49(1H, d), 5.62(1H, d), 6.79～7.54(5H, m) [$CDCl_3$] | 424, 240 |
| 210 | 4,5-F | 6-Me | 2560～3450 1700, 1680 | 2.31(3H, s), 2.71(1H, dd), 3.17(1H, dd), 3.99(1H, dd), 5.53(1H, d), 5.64(1H, d), 6.88～7.53(5H, m) [$CDCl_3$] | 420, 236 |
| 211 | 4,5-F | 6-OMe | 2560～3450 1725, 1660 | 2.52(1H, dd), 2.93(1H, dd), 3.78(3H, s), 3.95(1H, dd), 5.58(1H, d), 5.65(1H, d), 6.67～7.72(5H, m) [$CD_3OD$] | 436, 252 |

TABLE 34

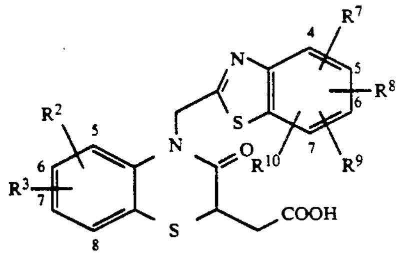

| Ex. | $R^7$, $R^8$, $R^9$, $R^{10}$ | $R^2$, $R^3$ | IR (KBr) $cm^{-1}$ | NMR: δ | MS (EI) m/z |
|---|---|---|---|---|---|
| 212 | 6,7-F | 6-OMe | 2600~3450 1710, 1675 | 2.70(1H, dd), 3.17(1H, dd), 3.78 (3H, s), 3.98(1H, dd), 5.46(1H, d), 5.59(1H, d), 6.22~7.76 (5H, m) [$CDCl_3$] | 436, 252 |
| 213 | 5,7-F | 8-F | 2530~3450 1730, 1665 | 2.75(1H, dd), 3.21(1H, dd), 4.01(1H, dd), 5.47(1H, d), 5.64(1H, d), 6.87~7.56(5H, m) [$CDCl_3$] | 424, 240 |

TABLE 35

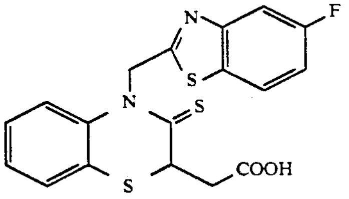

| Ex. | IR (KBr) $cm^{-1}$ | NMR ($CDCl_3$-$DMSOd_6$): δ | MS (EI) m/z |
|---|---|---|---|
| 214 | 2550~3470 1712 | 2.57(1H, dd), 3.01(1H, dd), 4.61 (1H, dd), 5.90(1H, d), 6.49(1H, d), 7.10~7.82(7H, m) | 404 |

EXAMPLE 215

2-[4-(4-Bromo-2-fluorophenylmethyl)-3,4-dihydro-3-oxo-2H-1,4-benzothiazin-2-yl]acetic acid

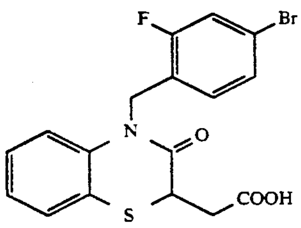

To 8 ml of 1 N sodium hydroxide-dioxane (1:1) mixture was added 700 mg of the compound of Example 20. After the mixture had been stirred at room temperature for 2 hours, it was acidified with 1 N hydrochloric acid. The mixture was extracted with ethyl acetate. The ethyl acetate layer was washed with water dried, and concentrated. The resulting crude product was recrystallized from ethyl acetate-isopropyl ether to give 620 mg of 2-[4-(4-bromo-2-fluorophenylmethyl)-3,4-dihydro-3-oxo-2H-1,4-benzothiazin-2-yl]acetic acid. The structural formula and physical data of this compound are shown in Table 36.

EXAMPLES 216 THROUGH 257

In a manner substantially similar to Example 215, the compounds shown in Tables 36 through 41 were obtained.

Together with the compound obtained in Example 215, the structural formulae and physical data of these compounds are shown in Tables 36 through 41.

TABLE 36

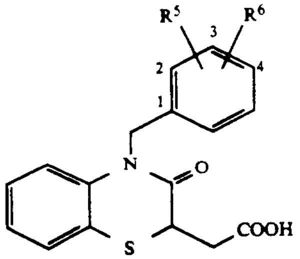

| Ex. | $R^5$ | $R^6$ | melting Point (°C.) | IR (KBr) ($cm^{-1}$) | NMR ($CDCl_3$) δ | MS (EI) m/z |
|---|---|---|---|---|---|---|
| 215 | 2-F | 4-Br | 138~139 | 2580~3460 1705, 1670 | 2.69(1H, dd), 3.15 (1H, dd), 3.99(1H, dd), 5.18(1H, d), 5.26(1H, d), 6.90~7.39(7H, m) | 411, 409, 222 |
| 216 | 3-Cl | 4-Cl | | 2940~3540 1720, 1660 | 2.67(1H, dd), 3.11 (1H, dd), 3.98(1H, dd), 5.09(1H, d), 5.19(1H, d), 6.84~7.38(7H, m) | 383, 381, 222 |
| 217 | H | H | 141~142 | 2600~3460 1714, 1662 | 2.70(1H, dd), 3.18 (1H, dd), 4.00(1H, dd), 5.15(1H, d), 5.29(1H,. d) 6.97~7.38(9H, m) | 313, 222 |
| 218 | 4-$OCH_3$ | H | | 2550~3450 1715, 1665 | 2.80(1H, dd), 3.26 (1H, dd), 3.89(3H, s), 5.26(1H, d), 5.34(1H, d) 6.95~7.80(9H, m) | 343, 121 |
| 219 | 4-tert-Bu | H | 148~150 | 2580~3450 1720, 1675 | 1.28(9H, s), 2.68(1H, dd) 3.17(1H, dd), 4.00(1H, dd), 5.09(1H, d), 5.26 (1H, d)6.96~7.37(8H, m) | 369, 222 |
| 220 | 4-$CH_3$ | H | 134~136 | 2580~3450 1720, 1675 | 2.29(3H, s), 2.68(1H, dd) 3.16(1H, dd), 3.99(1H, dd), 5.11(1H, d), 5.23 (1H, d), 6.95~7.36(8H, m) | 327, 222 |
| 221 | 3-CN | H | 132~135 | 2850~3650 2230, 1665 | 2.56(1H, dd), 2.94(1H, dd), 3.97(1H, dd), 5.21 (2H, s), 6.90~7.55(8H, m) | 338, 222 |
| 222 | 3-$CF_3$ | H | | 2550~3520 1730, 1660 | 2.70(1H, dd), 3.15(1H, dd), 4.10(1H, dd), 5.21 (1H, d), 5.33(1H, d), 6.95~ 7.51(8H, m) | 381, 222 |
| 223 | 4-Br | H | 134~136 | 2600~3450 1710, 1685 | 2.69(1H, dd), 3.16(1H, dd), 3.99(1H, dd), 5.21 (1H, d), 5.21(1H, d), 6.93~ 7.43(8H, m) | 421, 419, 250 |

TABLE 37

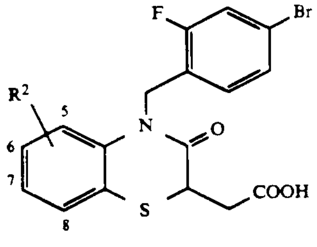

| Ex. | $R^2$ | melting Point (°C.) | IR (KBr) ($cm^{-1}$) | NMR ($CDCl_3$) δ | MS (EI) m/z |
|---|---|---|---|---|---|
| 224 | 5-Cl | 147~149 | 2900~3300 1725, 1670 | 2.64(1H, dd), 3.15 (1H, dd), 3.76(1H, dd), 5.20(1H, d), 5.43(1H, d), 6.93~7.33(6H, m) | 445, 443, 256 |
| 225 | 5-F | | 2550~3400 1730, 1680 | 2.68(1H, dd), 3.18 (1H, dd), 3.86(1H, dd), 5.09(1H, d), 5.40(1H, d), 6.58~7.36(6H, m) | 429, 427, 240 |

TABLE 37-continued

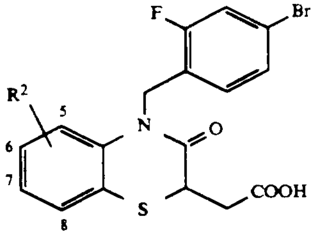

| Ex. | $R^2$ | melting Point (°C.) | IR (KBr) ($cm^{-1}$) | NMR ($CDCl_3$) δ | MS (EI) m/z |
|---|---|---|---|---|---|
| 226 | 5-$CH_3$ | 192~194 | 2580~3460 1705, 1680 | 2.39(3H, s), 2.65 (1H, dd), 3.12(1H, dd), 3.71(1H, dd), 4.78(1H, d), 5.36 (1H, d), 6.95~ 7.25(6H, m) | 425, 423, 236 |
| 227 | 5-$OCH_3$ | | 2570~3530 1715, 1665 | 2.66(1H, dd), 3.14 (1H, dd) 3.78(3H, s), 3.83(1H, dd), 5.21(1H, d), 5.31 | 441, 439, 252 |

TABLE 37-continued

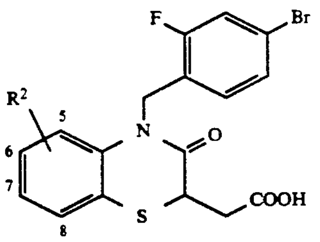

| Ex. | $R^2$ | melting Point (°C.) | IR (KBr) ($cm^{-1}$) | NMR ($CDCl_3$) δ | MS (EI) m/z |
|---|---|---|---|---|---|
| | | | | (1H, d), 6.74~7.12(6H, m) | |
| 228 | 6-Cl | 163~165 | 2600~3450 1714, 1680 | 2.70(1H, dd), 3.15 (1H, dd), 3.95(1H, dd), 5.19(2H, s), 6.90~7.32(6H, m) | 445, 443, 256 |
| 229 | 6-F | 147~148 | 2600~3460 1714, 1666 | 2.69(1H, dd), 3.15 (1H, dd), 3.96(1H, dd), 5.19(2H, s), 6.70~7.36(6H, m) | 429, 427, 240 |
| 230 | 6-$CH_3$ | 134~135 | 2550~3450 | 2.27(3H, s), 2.68 | 425, |

TABLE 37-continued

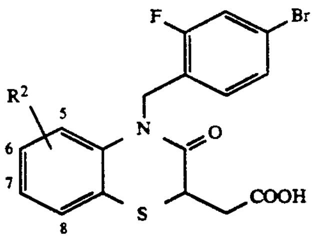

| Ex. | $R^2$ | melting Point (°C.) | IR (KBr) ($cm^{-1}$) | NMR ($CDCl_3$) δ | MS (EI) m/z |
|---|---|---|---|---|---|
| | | | 1702, 1668 | (1H, dd), 3.13(1H, dd), 3.95(1H, dd), 5.17(1H, d), 5.23 (1H, d), 6.81~7.23(6H, m) | 423, 236 |
| 231 | 6-$OCH_3$ | | 2570~3450 1720, 1668 | 2.51(1H, dd), 3.12 (1H, dd), 3.73(3H, s), 3.95(1H, dd), 5.20(2H, s), 6.58~7.28(6H, m) | 441, 439, 252 |

TABLE 38

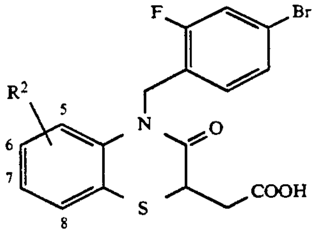

| Ex. | $R^2$ | $R^3$ | melting Point (°C.) | IR (KBr) ($cm^{-1}$) | NMR ($CDCl_3$) δ | MS (EI) m/z |
|---|---|---|---|---|---|---|
| 232 | 7-Cl | H | 164~166 | 2580~3460 1718, 1670 | 2.70(1H, dd), 3.16(1H, dd), 3.97(1H, dd), 5.20(2H, s), 6.89~7.37(6H, m) | 445, 443, 256 |
| 233 | 7-F | H | 136~138 | 2600~3490 1720, 1680 | 2.69(1H, dd), 3.15(1H, dd), 3.98(1H, dd), 5.20(2H, s), 6.80~7.26(6H, m) | 429, 427, 240 |
| 234 | 7-$CH_3$ | H | 152~154 | 2600~3460 1710, 1670 | 2.27(3H, s), 2.68(1H, dd), 3.14(1H, dd), 3.97(1H, dd), 5.20(2H, s), 6.85~7.26(6H, m) | 425, 423, 236 |
| 235 | 7-$OCH_3$ | H | 168~170 | 2570~3460 1705, 1660 | 2.70(1H, dd), 3.15(1H, dd), 3.76(3H, s), 3.99(1H, dd), 5.19(2H, s), 6.69~7.25(6H, m) | 441, 439, 252 |
| 236 | 7-Et | H | | 2550~3450 1710, 1670 | 1.20(3H, t), 2.57(2H, q), 2.69(1H, dd), 3.15(1H, dd), 3.98(1H, dd), 5.16(1H, d), 5.22(1H, d), 6.88~7.26(6H, m) | 439, 437, 250 |
| 237 | 7-iso-Pr | H | | 2600~3450 1710, 1670 | 1.21(6H, d), 2.69(1H, dd), 2.83(1H, Hep), 3.16(1H, dd), 3.99(1H, dd), 5.13(1H, d), 5.24(1H, d), 6.88~7.26(6H, m) | 453, 451, 264 |
| 238 | 7-tert-Bu | H | 157~159 | 2590~3330 1710, 1665 | 1.27(9H, s), 2.70(1H, dd), 3.17(1H, dd), 4.00(1H, dd), 5.13(1H, d), 5.24(1H, d), 6.89~7.37(6H, m) | 467, 465, 278 |

TABLE 39

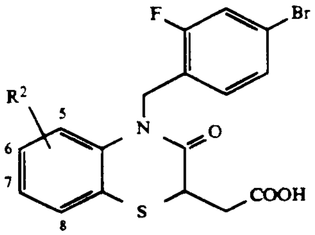

| Ex. | $R^2$ | $R^3$ | melting Point (°C.) | IR (KBr) ($cm^{-1}$) | NMR ($CDCl_3$) δ | MS (EI) m/z |
|---|---|---|---|---|---|---|
| 239 | 7-EtO | H | | 2580～3460 1718, 1670 | 1.38(3H, t), 2.69(1H, dd), 3.14(1H, dd), 3.97(2H, q), 3.98(1H, dd), 5.18(2H, s), 6.68～7.24(6H, m) | 455, 453, 266 |
| 240 | 7-PrO | H | | 2600～3490 1720, 1680 | 1.01(3H, t), 1.77(2H, m), 2.69(1H, dd), 3.15(1H, dd), 3.86(2H, t), 3.98(1H, dd), 5.18(2H, s), 6.69～7.26(6H, m) | 469, 467, 280 |
| 241 | 7-$SCH_3$ | H | | 2600～3460 1710, 1670 | 2.45(3H, s), 2.70(1H, dd), 3.16(1H, dd), 3.98(1H, dd), 5.20(2H, s), 6.89～7.27(6H, m) | 457, 455, 268 |
| 242 | 8-Cl | H | 158～159 | 2550～3450 1702, 1686 | 2.76(1H, dd), 3.20(1H, dd), 3.97(1H, dd), 5.17(1H, d), 5.25(1H, d), 6.91～7.26(6H, m) | 445, 443, 256 |
| 243 | 8-$CH_3$ | H | | 2580～3450 1716, 1674 | 2.36(3H, s), 2.71(1H, dd), 3.92(1H, dd), 5.17(1H, d), 5.25(1H, d), 6.84～7.24(6H, m) | 425, 423, 236 |
| 244 | 6-$CH_3$ | 8-$CH_3$ | | 2580～3450 1716, 1674 | 2.23(3H, s), 2.32(3H, s), 2.69(1H, dd), 3.15(1H, dd), 3.89(1H, dd), 5.16(1H, d), 5.22(1H, d), 6.68(1H, s), 6.77(1H, s), 6.91～7.26(3H, m) | 439, 437, 250 |
| 245 | 6-$CH_3$ | 7-$CH_3$ | | 2570～3460 1705, 1660 | 2.17(9H, s), 2.66(1H, dd), 3.11(1H, dd), 3.94(1H, dd), 5.19(2H, s), 6.78～7.25(5H, m) | 439, 437, 250 |
| 246 | 6-$OCH_3$ | 8-$OCH_3$ | 143～144 | 2550～3450 1702, 1686 | 2.71(1H, dd), 3.15(1H, dd), 3.72(3H, s), 3.86(3H, s), 3.88(1H, dd), 5.18(1H, d), 5.23(1H, d), 6.24(2H, s), 6.94～7.26(3H, m) | 471, 469, 282 |

TABLE 40

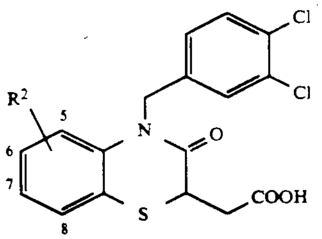

| Ex. | $R^2$ | melting Point (°C.) | IR (KBr) ($cm^{-1}$) | NMR ($CDCl_3$) δ | MS (EI) m/z |
|---|---|---|---|---|---|
| 247 | 5-Cl | 146～147 | 2600～3400 1715, 1680 | 2.71(1H, dd), 3.13 (1H, dd), 3.81(1H, dd), 5.07(1H, d), 5.53(1H, d), 6.92～7.35(6H, m) | 417, 415, 256 |
| 248 | 5-F | 160～161 | 2570～3400 1715, 1680 | 2.70(1H, dd), 3.18 (1H, dd), 3.86(1H, dd), 4.93(1H, d), 5.47(1H, d), 6.91～7.29(6H, m) | 401, 399, 240 |
| 249 | 5-$OCH_3$ | 141～143 | 2550～3430 1702, 1658 | 2.63(1H, dd), 3.07 (1H, dd), 3.70～3.92(4H, m), 5.04 (1H, d), 5.34(1H, d), 6.73～7.24 (6H, m) | 413, 411, 252 |
| 250 | 6-Cl | | 2580～3470 | 2.61(1H, dd), 3.08 | 417, |

TABLE 40-continued

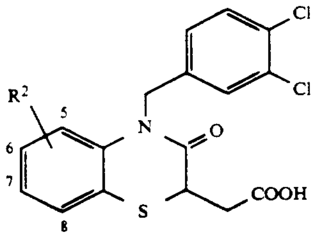

| Ex. | $R^2$ | melting Point (°C.) | IR (KBr) ($cm^{-1}$) | NMR ($CDCl_3$) δ | MS (EI) m/z |
|---|---|---|---|---|---|
| | | | 1700, 1678 | (1H, dd), 3.99(1H, dd), 5.14(2H, s), 6.94～7.41(6H, m) | 415, 256 |
| 251 | 6-F | 146～148 | 2600～3460 1716, 1664 | 2.71(1H, dd), 3.16 (1H, dd), 3.97(1H, dd), 5.10(1H, d), 5.18(1H, d), 6.69～7.41(6H, m) | 401, 399, 240 |
| 252 | 6-$CH_3$ | 188～190 | 2580～3400 1708, 1658 | 2.26(3H, s), 2.62 (1H, dd), 3.97(1H, dd), 5.10(1H, d), 5.18(1H, d), 6.76～7.39(6H, m) | 397, 395, 236 |
| 253 | 6-$OCH_3$ | 183～184 | 2570～3500 1698, 1672 | 2.69(1H, dd), 3.14 (1H, dd), 3.73(3H, s), 3.95(1H, dd), 5.10(1H, d), 5.19 | 413, 411, 252 |

TABLE 40-continued

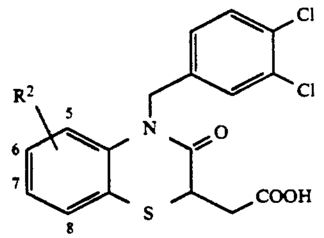

| Ex. | $R^2$ | melting Point (°C.) | IR (KBr) ($cm^{-1}$) | NMR ($CDCl_3$) δ | MS (EI) m/z |
|---|---|---|---|---|---|
| | | | | (1H, d), 6.54~7.39(6H, m) | |
| 254 | 7-$CH_3$ | | 2550~3530 1720, 1660 | 2.27(3H, s), 2.68 (1H, dd), 3.13(1H, dd), 3.97(1H, dd), 5.14(2H, s), 6.84~7.37(6H, m) | 397, 395, 236 |
| 255 | 7-$OCH_3$ | | 2600~3480 1716, 1666 | 2.69(1H, dd), 3.14 (1H, dd), 3.76(3H, s), 3.99(1H, dd), 5.12(2H, s), 6.70~7.37(6H, m) | 413, 411, 252 |
| 256 | 8-Cl | 153~154 | 2570~3440 1706, 1682 | 2.76(1H, dd), 3.19 (1H, dd), 3.97(1H, dd), 5.07(1H, d), 5.23(1H, d), 6.89~7.39(6H, m) | 417, 415, 256 |

TABLE 41

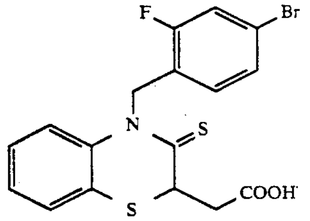

| Ex. | melting Point (°C.) | IR (KBr) ($cm^{-1}$) | NMR (DMSO-$d_6$) δ | MS (EI) m/z |
|---|---|---|---|---|
| 257 | 193~194 | 2560~3430 1700 | 2.58(1H, dd), 2.99(1H, dd), 4.54(1H, dd), 5.68(1H, d), 5.95(1H, d) 6.88~7.61(7H, m) | 427, 425, 392 |

EXAMPLE 258

(Z)-2-(4-Phenylmethyl-3,4-dihydro-3-oxo-2H-1,4-benzothiazin-2-ylidene)acetic acid

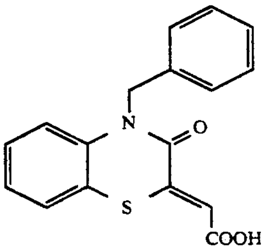

To 15 ml of ethanol were added 460 mg of the compound of Example 62 and 212 mg of potassium hydroxide. The mixture was refluxed for 30 minutes, then the solvent was distilled off. Diluted hydrochloric acid was added to the residue, and the aqueous mixture was extracted with ethyl acetate and dried.

After concentration, isopropyl ether was added to the residue to solidify. Thus, 390 mg of (Z)-2-(4-phenylmethyl-3,4-dihydro-3-oxo-2H-1,4-benzothiazin-2-ylidene)acetic acid was obtained as yellow powder. The structural formula and physical data of this compound are shown in Table 42.

EXAMPLES 259 AND 260

In a manner substantially similar to Example 258, the compounds shown in Table 42 were obtained.

Together with the compound obtained in Example 258, the structural formulae and physical data of these compounds are shown in Table 42.

TABLE 42

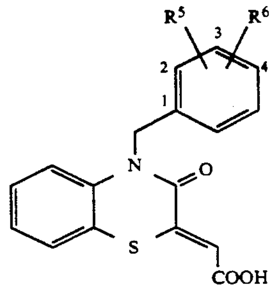

| Ex. | $R^5$ | $R^6$ | melting Point (°C.) | IR (KBr) $cm^{-1}$ | NMR ($CDCl_3$-DMSO$d_6$) δ | MS (EI) m/z |
|---|---|---|---|---|---|---|
| 258 | H | H | 211~213 | 2590~3430 1670, 1642 | 5.42(2H, s), 7.01~7.42 (10H, m) | 311, 154 |
| 259 | 3-Cl | 4-Cl | 227~230 (dec,) | 2590~3450 1670, 1645 | 5.34(2H, s), 6.87~7.52 (8H, m) | 381, 379, 159 |
| 260 | 2-F | 4-Br | 235~237 (dec.) | 2600~3300 1680, 1660 | 5.38(2H, s), 6.89~7.36 (8H, m) | 409, 407, 187 |

Hereafter examples of pharmaceutical preparations are shown.

PREPARATION EXAMPLE 1

By a routine method, granule was prepared according to the following formula.

| | |
|---|---|
| Compound of Example 183 | 20 g |
| Lactose | 315 g |
| Corn starch | 125 g |
| Crystalline cellulose | 25 g |

The above components were blended to obtain a homogeneous mixture. After the addition of 200 ml of 7.5% hydroxypropyl cellulose, the mixture was made into granule by means of an extruding granulator using a screen with a 0.5 Mm diameter. The granule was rounded and dried to produce a granulous preparation. The dried granule was coated with 1.9 kg of a film-coating liquid having the following composition using a fluid-type granulator to produce enteric coated granule.

| | |
|---|---|
| Hydroxypropylmethyl cellulose phthalate | 5.0 (W/W) % |
| Stearig acid | 0.25 (W/W) % |
| Methylene chloride | 50.0 (W/W) % |

-continued

| | |
|---|---|
| Ethanol | 44.75 (W/W) % |

PREPARATION EXAMPLE 2

By a routine method, tablets were prepared according to the following formula.

| | |
|---|---|
| Compound of Example 188 | 20 g |
| Lactose | 100 g |
| Corn starch | 36 g |
| Crystalline cellulose | 30 g |
| Calcium carboxymethyl cellulose | 10 g |
| Magnesium stearate | 4 g |

The components described above were homogeniously mixed and the mixture was prepared into tablets each weighing 200 mg with a pestle having a diameter of 7.5 mm using a sigle tabletting machine. Then, a coating solution having the following composition was sprayed to coat the tablets, whereby the tablets are covered with the coating solution in 10 mg/tablet. Thus enteral film coating tablets were obtained.

| Composition of coating solution: | |
|---|---|
| Hydroxypropylmethyl cellulose phthalate | 8.0 (W/W) % |
| Glycerol fatty acid ester | 0.4 (W/W) % |
| Methylene chloride | 50.0 (W/W) % |
| Breached bees wax | 0.1 (W/W) % |
| Isopropanol | 41.5 (W/W) % |

PREPARATION EXAMPLE 3

By a routine method, capsules were prepared according to the following formula.

| | |
|---|---|
| Compound of Example 189 | 200 g |
| Polysorbate 80 | 20 g |
| PANASETO ® 810 | 1780 g |

The components described above were mixed to completely dissolve. Then, soft capsules each containing 200 mg/capsule of the drug solution were prepared by the rotary method, by use of a coating solution for soft capsules comprising 100 parts of gelatin, 30 parts of conc. glycerine, 0.4 part of ethyl paraben and 0.2 part of propyl paraben.

PREPARATION EXAMPLE 4

By a routine method, an injection was prepared according to the following formula.

| | |
|---|---|
| Compound of Example 191 | 100 mg |
| Sodium acetate | 2 mg |
| Acetic acid (for adjusting pH to 5.8) | suitable quantity |
| Distilled water | balance |
| | 10 ml in total/vial |

By a routine method, eyedrop was prepared according to the following formula.

| | |
|---|---|
| Compound of Example 168 | 0.05 g |
| Polysorbate 80 | 0.2 g |
| Monosodium phosphate dihydrate | 0.2 g |

-continued

| | |
|---|---|
| Disodium phosphate 12 hydrate | 0.5 g |
| Sodium chloride | 0.75 g |
| Methyl p-oxybenzoate | 0.026 g |
| Propyl p-oxybenzoate | 0.014 g |
| Sterile purified water | to make 100 ml |

The novel compounds of the present invention, 1,4-benzothiazine derivatives (I) and their salts possess an aldose reductase inhibitory activity and excellent safety and are thus effective as drugs for therapeutic treatment of diabetic complications such as corneal wound healing defect, cataract, neuropathy, retinopathy or nephropathy, especially cataract and neuropathy.

What is claimed is:

1. A 1,4-benzothiazine-2-acetic acid derivative represented by formula (I) below:

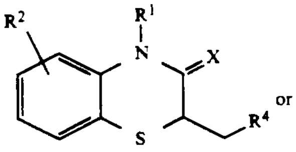

or

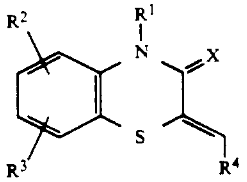

(I)

wherein $R^1$ represents a group shown by formula (II) or (III):

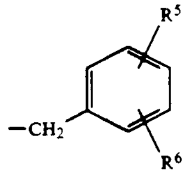

(II)

wherein $R^5$ and $R^6$, which may be the same or different, each represents hydrogen or halogen or an alkyl having 1-6 carbon atoms, an alkoxy having 1-6 carbon atoms, trifluoromethyl or cyano; and wherein $R^7$, $R^8$, $R^9$ and $R^{10}$, which may be the same or different, each represents hydrogen, a halogen, alkyl having 1 to 6 carbon atoms, alkoxy having 1 to 6 carbon atoms or trifluoromethyl; $R^2$ and $R^3$, which may be the same or different, each represents hydrogen, a halogen, an alkyl having 1 to 6 carbon atoms, alkoxy having 1 to 6 carbon atoms, alkylthio having 1 to 6 carbon atoms, trifluoromethyl or trifluoromethoxy; $R^4$ represents carboxyl, or alkoxy carbonyl having 2 to 7 carbon atoms; and X represents oxygen or sulfur, or its pharmaceutically suitable salt.

2. A 1,4-benzothiazine-2-acetic acid derivative represented by the formula (IV):

(IV)

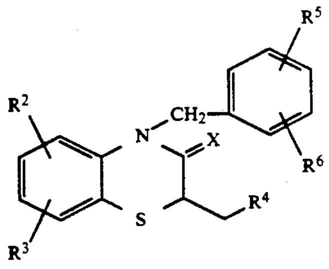

or

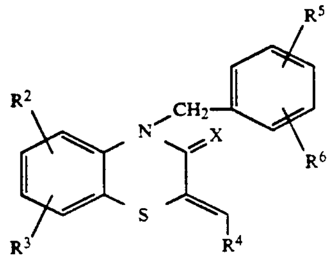

or wherein $R^2$, $R^3$, $R^4$, $R^5$ and $R^6$ have the same significances as defined in claim 1, or its pharmaceutically suitable salt.

3. A 1,4-benzothiazine-2-acetic acid derivative represented by the formula (V):

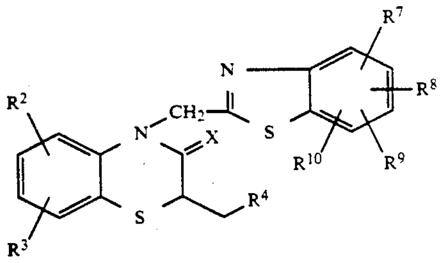

or

-continued

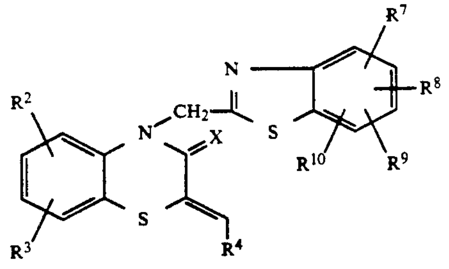

wherein $R^2$, $R^3$, $R^4$, $R^7$, $R^8$, $R^9$ and $R^{10}$ and have the same significances as defined in claim 1, or its pharmaceutically suitable salt.

4. A 1,4-benzothiazine-2-acetic acid derivative represented by the formula (IV) or its pharmaceutically suitable salt as claimed in claim 2, wherein $R^4$ is carboxyl.

5. A 1,4-benzothiazine-2-acetic acid derivative represented by the formula (V) or its pharmaceutically suitable salt as claimed in claim 3, wherein $R^4$ is carboxyl.

6. A 1,4-benzothiazine-2-acetic acid derivative represented by the formula (IV) or its pharmaceutically suitable salt as claimed in claim 2, wherein $R^4$ is an alkoxy carbonyl having 2 to 7 carbon atoms.

7. A 1,4-benzothiazine-2-acetic acid derivative represented by formula (V) or its pharmaceutically suitable salt as claimed in claim 3, wherein $R^4$ is an alkoxy carbonyl having 2 to 7 carbon atoms.

8. A 1,4-benzothiazine-2-acetic acid derivative represented by the formula (V) or its pharmaceutically suitable salt as claimed in claim 3, wherein $R^7$, $R^8$, $R^9$ and $R^{10}$, which may be the same or different, each represents hydrogen, fluorine or chlorine.

9. A composition for the treatment of diabetes comprising as an effective ingredient a 1,4-benzothiazine-2-acetic acid derivative or its pharmaceutically suitable salt as defined in claim 1 in a pharmaceutically acceptable carrier.

10. A method of prevention and treatment of diabetes comprising administering to a person in need thereof an effective amount of 1,4-benzothiazine-2-acetic acid derivative or its pharmaceutically suitable salt as claimed in claim 1.

11. A method of prevention and treatment of diabetic cataracts, diabetic retinopathy, diabetic nephropathy, and diabetic neuropathy, comprising administering to a person in need thereof an effective amount of a 1,4-benzothiazine-2-acetic acid derivative or its pharmaceutically suitable salt as claimed in claim 1.

* * * * *